(12) United States Patent
Ren et al.

(10) Patent No.: US 7,745,437 B2
(45) Date of Patent: Jun. 29, 2010

(54) COMPOUNDS AND COMPOSITIONS AS PROTEIN KINASE INHIBITORS

(75) Inventors: Pingda Ren, San Diego, CA (US); Xia Wang, San Diego, CA (US); Guobao Zhang, San Diego, CA (US); Qiang Ding, San Diego, CA (US); Shuli You, Shanghai (CN); Qiong Zhang, San Diego, CA (US); Greg Chopiuk, San Diego, CA (US); Pamela A. Albaugh, Carlsbad, CA (US); Taebo Sim, San Diego, CA (US); Nathanael Schiander Gray, Boston, MA (US)

(73) Assignee: IRM LLC, Hamilton (BM)

( * ) Notice: Subject to any disclaimer, the term of this patent is extended or adjusted under 35 U.S.C. 154(b) by 746 days.

(21) Appl. No.: 11/628,881

(22) PCT Filed: Jun. 9, 2005

(86) PCT No.: PCT/US2005/020371

§ 371 (c)(1),
(2), (4) Date: Mar. 9, 2007

(87) PCT Pub. No.: WO2005/123719

PCT Pub. Date: Dec. 29, 2005

(65) Prior Publication Data

US 2007/0225286 A1    Sep. 27, 2007

Related U.S. Application Data

(60) Provisional application No. 60/578,491, filed on Jun. 10, 2004.

(51) Int. Cl.
*C07D 403/04*     (2006.01)
*A61K 31/4178*    (2006.01)

(52) U.S. Cl. .............. 514/235.8; 514/249; 514/252.02; 514/254.05; 514/256; 544/122; 544/238; 544/295; 544/328

(58) Field of Classification Search ................ 544/122, 544/238, 295, 328; 514/235.8, 249, 252.02, 514/254.05, 256
See application file for complete search history.

(56) References Cited

U.S. PATENT DOCUMENTS 6,747,031 B2 *    6/2004    Arnaiz et al. ............... 514/256

OTHER PUBLICATIONS

Ulrich, Chapter 4:Crystallization, Kirk-Othmer Encyclopedia of Chemical Technology, Aug. 2002.*
Vippagunta et al., Crystalline Solids, Advanced Drug Deliversy Reviews, 48, pp. 3-26, 2001.*
Simone, Oncology: Introduction, Cecil Textbook of Medicine, 20th Edition, vol. 1, pp. 1004-1010, 1996.*
Traxler, Protein Tyrosine Kinase Inhibitors in cancer treatment, Expert Opinion on Therapeutic Patents, 7(6):571-588, 1997.*
West, Solid Solutions, Solid State Chemistry and its applications, pp. 358 & 365, 1988.*

* cited by examiner

*Primary Examiner*—Deepak Rao
(74) *Attorney, Agent, or Firm*—Scott W. Reid; Genomics Institute of the Novartis Research Foundation

(57) ABSTRACT

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Abl, BCR-Abl, PDGF-R, trkB, c-SRC, BMX, FGFR3, b-RAF, $\Sigma\Gamma K$, $T\iota\epsilon2$, $\Lambda\chi\kappa$, $\theta NK2\alpha2$, MKK4, c-RAF, MKK6, SAPK2α and SAPK2β kinases.

8 Claims, No Drawings

COMPOUNDS AND COMPOSITIONS AS PROTEIN KINASE INHIBITORS

CROSS-REFERENCE TO RELATED APPLICATIONS

This application is the National Stage of Application No. PCT/US2005020371, filed on Jun. 9, 2005, which claims benefit under 35 U.S.C. 119(e) of U.S. Provisional Application No. 60/578,491 filed Jun. 10, 2004. The contents of both are incorporated herein by reference in their entirety.

BACKGROUND OF THE INVENTION

1. Field of the Invention

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Abl, BCR-Abl, PDGF-R, trkB, c-SRC, BMX, FGFR3, b-RAF, SGK, Tie2, Lck, JNK2α2, MKK4, c-RAF, MKK6, SAPK2α and SAPK2β kinases.

2. Background

The protein kinases represent a large family of proteins, which play a central role in the regulation of a wide variety of cellular processes and maintaining control over cellular function. A partial, non-limiting, list of these kinases include: receptor tyrosine kinases such as platelet-derived growth factor receptor kinase (PDGF-R), the nerve growth factor receptor, trkB, and the fibroblast growth factor receptor, FGFR3, B-RAF; non-receptor tyrosine kinases such Abl and the fusion kinase BCR-Abl, Lck, Bmx and c-src; and serine/threonine kinases such as c-RAF, sgk, MAP kinases (e.g., MKK4, MKK6, etc.) and SAPK2α and SAPK2β. Aberrant kinase activity has been observed in many disease states including benign and malignant proliferative disorders as well as diseases resulting from inappropriate activation of the immune and nervous systems.

The novel compounds of this invention inhibit the activity of one or more protein kinases and are, therefore, expected to be useful in the treatment of kinase-associated diseases.

SUMMARY OF THE INVENTION

In one aspect, the present invention provides compounds of Formula I:

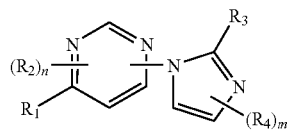

in which:

m and n are independently selected from 0, 1 and 2;

$R_1$ is selected from —$XNR_5R_6$, —$XOR_5$, —$XC(O)R_5$, —$XR_5$ and —$XS(O)_{0-2}R_5$; wherein X is a bond or $C_{1-4}$alkylene optionally substituted by 1 to 2 $C_{1-6}$alkyl radicals; $R_5$ is selected from hydrogen, $C_{1-6}$alkyl, $C_{6-10}$aryl-$C_{0-4}$alkyl, $C_{5-10}$heteroaryl-$C_{0-4}$alkyl, $C_{3-10}$ cycloalkyl-$C_{0-4}$alkyl and $C_{3-10}$heterocycloalkyl-$C_{0-4}$alkyl; and $R_6$ is selected from hydrogen and $C_{1-6}$alkyl; or $R_5$ and $R_6$ together with the nitrogen to which $R_5$ and $R_6$ are both attached form heteroaryl or heterocycloalkyl;

wherein any aryl, heteroaryl, cycloalkyl and heterocycloalkyl of $R_5$ or the combination of $R_5$ and $R_6$ can be optionally substituted with 1 to 3 radicals independently selected from halo, nitro, cyano, hydroxy, $C_{1-6}$alkyl, $C_{1-6}$alkoxy, halo-substituted-alkyl, halo-substituted-alkoxy, —$XNR_7R_8$, —$XOR_7$, —$XNR_7S(O)_2R_8$, —$XNR_7S(O)R_8$, —$XNR_7SR_8$, —$XC(O)NR_7R_8$, —$XC(O)NR_7XNR_7R_8$, —$XNR_7C(O)NR_7R_8$, —$XNR_7XNR_7R_8$, —$XNR_7OR_7$, —$XNR_7C(=NR_7)NR_7R_8$, —$XS(O)_2R_9$, —$XNR_7C(O)R_8$, —$XNR_7C(O)R_9$, —$XR_9$, —$XC(O)OR_8$, —$XS(O)_2NR_7R_8$, —$XS(O)NR_7R_8$ and —$XSNR_7R_8$; wherein X is a bond or $C_{1-4}$alkylene; $R_7$ and $R_8$ are independently selected from the group consisting of hydrogen and $C_{1-4}$alkyl; and $R_9$ is selected from $C_{3-10}$heterocycloalkyl and $C_{5-10}$heteroaryl; wherein said heterocycloalkyl or heteroaryl of $R_9$ is optionally substituted with a radical selected from the group consisting of $C_{1-4}$alkyl, —$XNR_7XNR_7R_7$, $XNR_7XOR_7$ and —$XOR_7$;

$R_2$ and $R_4$ are independently selected from halo, hydroxy, $C_{1-4}$alkyl, $C_{1-4}$alkoxy, halo-substituted-$C_{1-4}$alkyl and halo-substituted-$C_{1-4}$alkoxy;

$R_3$ is selected from —$NR_{10}R_{11}$, —$NR_{10}C(O)R_{11}$, —$NR_{10}S(O)_{0-2}R_{11}$, and —$NR_{10}C(O)NR_{10}R_{11}$; wherein $R_{10}$ is selected from hydrogen and $C_{1-6}$alkyl; $R_{11}$ is selected from $C_{6-10}$aryl, $C_{5-10}$heteroaryl, $C_{3-10}$cycloalkyl and $C_{3-10}$heterocycloalkyl; wherein any aryl, heteroaryl, cycloalkyl or heterocycloalkyl of $R_{11}$, is optionally substituted by 1 to 3 radicals selected from halo, nitro, cyano, hydroxy, $C_{1-6}$alkyl, $C_{1-6}$alkoxy, halo-substituted-alkyl, halo-substituted-alkoxy, —$NR_{12}C(O)R_{13}$, —$NR_{12}C(O)NR_{12}R_{13}$, —$C(O)NR_{12}R_{13}$, —$NR_{12}S(O)_{0-2}R_{13}$ and —$S(O)_{0-2}NR_{12}R_{13}$; wherein $R_{12}$ is selected from hydrogen and $C_{1-6}$alkyl; $R_{13}$ is selected from $C_{6-10}$aryl, $C_{5-10}$heteroaryl, $C_{3-10}$cycloalkyl and $C_{3-10}$heterocycloalkyl; wherein any aryl, heteroaryl, cycloalkyl or heterocycloalkyl of $R_{13}$ is optionally substituted with 1 to 3 radicals independently selected from halo, $C_{1-6}$alkyl, halo-substituted-$C_{1-6}$alkyl, $C_{1-6}$alkoxy, halo-substituted-$C_{1-6}$alkoxy, —$XNR_7R_8$, $C_{6-10}$aryl-$C_{0-4}$alkyl, $C_{5-10}$heteroaryl-$C_{0-4}$alkyl, $C_{3-10}$ cycloalkyl-$C_{0-4}$alkyl, $C_{3-10}$heterocycloalkyl-$C_{0-4}$alkoxy and $C_{3-10}$heterocycloalkyl-$C_{0-4}$alkyl; wherein X, $R_7$ and $R_8$ are as described above and wherein any aryl, heteroaryl, cycloalkyl or heterocycloalkyl substituent of $R_{13}$ is further optionally substituted by 1 to 3 radicals independently selected from halo, $C_{1-6}$alkyl, halo-substituted-$C_{1-6}$alkyl, hydroxy-substituted-$C_{1-6}$alkyl, $C_{1-6}$alkoxy, $C_{3-10}$heterocycloalkyl and halo-substituted-$C_{1-6}$alkoxy; and the N-oxide derivatives, prodrug derivatives, protected derivatives, individual isomers and mixture of isomers thereof, and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof, or a pharmaceutically acceptable salt thereof, in admixture with one or more suitable excipients.

In a third aspect, the present invention provides a method of treating a disease in an animal in which inhibition of kinase activity, particularly Abl, BCR-Abl, PDGF-R, trkB, c-SRC, BMX, FGFR3, B-RAF, SGK, Tie2, Lck, JNK2α2, MKK4, c-RAF, MKK6, SAPK2α and/or SAPK2β activity, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which kinase activity, particularly Abl, BCR-Abl, PDGF-R, trkB, c-SRC, BMX, FGFR3, B-RAF, SGK, Tie2, Lck, JNK2α2, MKK4, c-RAF, MKK6, SAPK2α and/or SAPK2β activity, contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl above where one or more of the ring members is a heteroatom. For example heteroaryl includes pyridyl, indolyl, indazolyl, quinoxalinyl, quinolinyl, benzofuranyl, benzopyranyl, benzothiopyranyl, benzo[1,3] dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$ alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, etc.

"Halogen" (or halo) preferably represents chloro or fluoro, but may also be bromo or iodo.

"Mutant forms of BCR-Abl" means single or multiple amino acid changes from the wild-type sequence. Over 22 mutations have been reported to date with the most common being G250E, E255V, T315I, F317L and M351T.

"Treat", "treating" and "treatment" refer to a method of alleviating or abating a disease and/or its attendant symptoms.

DESCRIPTION OF THE PREFERRED EMBODIMENTS

The fusion protein BCR-Abl is a result of a reciprocal translocation that fuses the Abl proto-oncogene with the Bcr gene. BCR-Abl is then capable of transforming B-cells through the increase of mitogenic activity. This increase results in a reduction of sensitivity to apoptosis, as well as altering the adhesion and homing of CML progenitor cells. The present invention provides compounds, compositions and methods for the treatment of kinase related disease, particularly Abl, BCR-Abl, PDGF-R, trkB, c-SRC, BMX, FGFR3, B-RAF, b-RAF, SGK, Tie2, Lck, JNK2α2, MKK4, c-RAF, MKK6, SAPK2α and SAPK2β kinase related diseases. For example, leukemia and other proliferation disorders related to BCR-Abl can be treated through the inhibition of wild type and mutant forms of Bcr-Abl.

In one embodiment, with reference to compounds of Formula I, are compounds of Formula Ia:

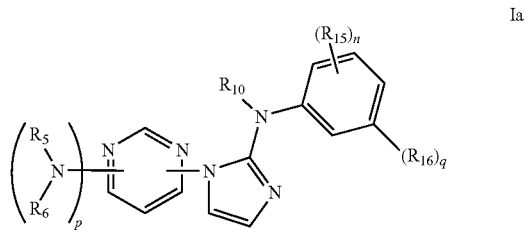

Ia in which:
p is selected from 0 and 1;
n is selected from 0, 1, 2 and 3;
q is selected from 0 and 1;
$R_5$ is selected from hydrogen, $C_{1-6}$alkyl, $C_{6-10}$aryl-$C_{0-4}$alkyl, $C_{5-10}$heteroaryl-$C_{0-4}$alkyl, $C_{3-10}$cycloalkyl-$C_{0-4}$alkyl and $C_{3-10}$heterocycloalkyl-$C_{0-4}$alkyl; and $R_6$ is selected hydrogen and $C_{1-6}$alkyl; or $R_5$ and $R_6$ together with the nitrogen to which $R_5$ and $R_6$ are both attached form heteroaryl or heterocycloalkyl;

wherein any aryl, heteroaryl, cycloalkyl and heterocycloalkyl of $R_5$ or the combination of $R_5$ and $R_6$ can be optionally substituted with 1 to 3 radicals independently selected from halo, nitro, cyano, hydroxy, $C_{1-6}$alkyl, $C_{1-6}$alkoxy, halo-substituted-alkyl, halo-substituted-alkoxy, —XNR$_7$R$_8$, —XOR$_7$, —XNR$_7$S(O)$_2$R$_8$, —XNR$_7$S(O)R$_8$, —XNR$_7$SR$_8$, —XC(O)NR$_7$R$_8$, —XC(O)NR$_7$XNR$_7$R$_8$, —XNR$_7$C(O) NR$_7$R$_8$, —XNR$_7$XNR$_7$R$_8$, —XNR$_7$XOR$_7$, —XNR$_7$C (═NR$_7$)NR$_7$R$_8$, —XS(O)$_2$R$_9$, —XNR$_7$C(O)R$_8$, —XNR$_7$C(O)R$_9$, —XR$_9$, —XC(O)OR$_8$, —XS(O)$_2$NR$_7$R$_8$, —XS(O) NR$_7$R$_8$ and —XSNR$_7$R$_8$; wherein X is a bond or $C_{1-4}$alkylene; $R_7$ and $R_8$ are independently selected from the group consisting of hydrogen and $C_{1-4}$alkyl; and $R_9$ is selected from $C_{3-10}$heterocycloalkyl and $C_{5-10}$heteroaryl; wherein said heterocycloalkyl or heteroaryl of $R_9$ is optionally substituted with a radical selected from the group consisting of $C_{1-4}$alkyl, —XNR$_7$XNR$_7$R$_7$, XNR$_7$XOR$_7$ and —XOR$_7$; wherein X and $R_7$ are as described above;

$R_{10}$ is selected from hydrogen and $C_{1-6}$alkyl;
$R_{15}$ is selected from halo, nitro, cyano, hydroxy, $C_{1-6}$alkyl, $C_{1-6}$alkoxy, halo-substituted-alkyl and halo-substituted-alkoxy; and $R_{16}$ is selected from —NR$_{12}$C(O)R$_{13}$, —NR$_{12}$C(O) NR$_{12}$R$_{13}$, —C(O)NR$_{12}$R$_{13}$, —NR$_{12}$S(O)$_{0-2}$R$_{13}$ and —S (O)$_{0-2}$NR$_{12}$R$_{13}$; wherein $R_{12}$ is selected from hydrogen and $C_{1-6}$ alkyl; $R_{13}$ is selected from $C_{6-10}$aryl, $C_{5-10}$heteroaryl, $C_{3-10}$cycloalkyl and $C_{3-10}$heterocycloalkyl; wherein any aryl, heteroaryl, cycloalkyl or heterocycloalkyl of $R_{13}$ is optionally substituted with 1 to 3 radicals independently selected from halo, $C_{1-6}$alkyl, halo-substituted-$C_{1-6}$alkyl, $C_{1-6}$alkoxy, halo-substituted-$C_{1-6}$alkoxy, —XNR$_7$R$_8$, $C_{6-10}$aryl-$C_{0-4}$alkyl, $C_{5-10}$ heteroaryl-$C_{0-4}$alkyl, $C_{3-10}$cycloalkyl-$C_{0-4}$alkyl, $C_{3-10}$heterocycloalkyl-$C_{0-4}$alkoxy and $C_{3-10}$heterocycloalkyl-$C_{0-4}$alkyl; wherein X, $R_7$ and $R_8$ are as described above and wherein any aryl, heteroaryl, cycloalkyl or heterocycloalkyl substituent of $R_{13}$ is further optionally substituted by 1 to 3 radicals independently selected from halo, $C_{1-6}$alkyl, halo-substituted-$C_{1-6}$alkyl, hydroxy-substituted-$C_{1-6}$alkyl, $C_{1-6}$alkoxy, $C_{3-10}$heterocycloalkyl and halo-substituted-$C_{1-6}$ alkoxy.

In another embodiment, $R_5$ is selected from hydrogen, morpholino-ethyl, cyclopropyl, methyl, 3-(2-oxo-pyrrolidin-1-yl)-propyl, benzo[1,3]dioxol-5-yl, 3-(4-methyl-piperazin-1-yl)-propyl, hydroxymethyl-phenyl, (1-hydroxyethyl)-phenyl, morpholino, pyridinyl, methyl-carbonyl, methyl-sulfonyl, methyl-pyridinyl, amino-cyclohexyl, piperidinyl, methyl-piperazinyl-ethyl, dimethyl-pyrazolyl, methyl-pyrazolyl, dimethyl-pyridinyl, methyl-pyridinyl, ethyl-piperazinyl-pyridinyl, amino-carbonyl-pyridinyl, cyano-pyridinyl, dimethyl-amino-ethyl, methoxy-ethyl, methyl-pyrrolidinyl-ethyl, ethyl-pyrazolyl, dimethyl-amino-propyl, isopropyl, furanyl-methyl, methyl-piperazinyl-propyl, benzo[1,3]dioxol-5-ylmethyl, 2-methyl-6-morpholin-4-yl-pyridin-3-yl, methyl-pyrimidinyl, methoxy-pyridinyl, fluoro-phenyl, dimethyl-amino-ethyl-aminocarbonyl, pyridinyl-methyl, thiazolyl-methyl, methyl-pyrazinyl-methyl, imidazolyl-propyl, amino-carbonyl-phenyl, or $R_5$ and $R_6$ together with the nitrogen atom to which they are both attached form a group selected from morpholino, piperidinyl and piperazinyl optionally substituted with a group selected from ethyl, pyridinyl and morpholino.

In a further embodiment, $R_{16}$ is selected from —NHC(O)$R_{13}$, —NHC(O)NH$R_{13}$, —C(O)NH$R_{13}$, —NHS(O)$_2R_{13}$ and —S(O)$_2$NH$R_{13}$; wherein $R_{13}$ is selected from phenyl, pyridazinyl, pyridinyl, furanyl, pyrrolyl, imidazolyl, pyrazolyl, quinoxalinyl, thienyl and thiazolyl; wherein $R_{13}$ is optionally substituted with 1 to 3 radicals independently selected from methyl, t-butyl, halo, trifluoromethyl, diethyl-amino, dimethyl-amino, benzyl, piperidinyl-amino, pyrrolidinyl-methoxy, ethyl-piperazinyl-methyl, morpholino, methyl-piperazinyl, methyl-piperazinyl-methyl, ethyl-piperazinyl, methyl-imidazolyl, morpholino-methyl, pyrrolidinyl-piperidinyl, piperazinyl-methyl, hydroxy-piperidinyl, 1-methyl-piperidin-4-yloxy, piperidinyl-oxy, methyl-pyrazinyl, pyrazinyl and hydroxyethyl-piperazinyl.

Preferred compounds of the invention are selected from N-[4-methyl-3-(1-{6-[4-(2-morpholin-4-yl-ethyl)-phenylamino]-pyrimidin-4-yl}-1H-imidazol-2-ylamino)-phenyl]-3-trifluoromethyl-benzamide, N-{3-[1-(6-cyclopropylamino-pyrimidin-4-yl)-1H-imidazol-2-ylamino]-4-methyl-phenyl}-3-(4-ethyl-piperazin-1-yl)-5-trifluoromethyl-benzamide, N-(4-methyl-3-{1-[6-(2-morpholin-4-yl-ethylamino)-pyrimidin-4-yl]-1H-imidazol-2-ylamino}-phenyl)-3-trifluoromethyl-benzamide, N-{3-[1-(6-cyclopropylamino-pyrimidin-4-yl)-1H-imidazol-2-ylamino]-4-methyl-phenyl}-3-trifluoromethyl-benzamide, N-{4-methyl-3-[1-(6-methylamino-pyrimidin-4-yl)-1H-imidazol-2-ylamino]-phenyl}-3-trifluoromethyl-benzamide, N-[4-methyl-3-(1-{6-[3-(2-oxo-pyrrolidin-1-yl)-propylamino]-pyrimidin-4-yl}-1H-imidazol-2-ylamino)-phenyl]-3-trifluoromethyl-benzamide, N-(3-{1-[6-(benzo[1,3]dioxol-5-ylamino)-pyrimidin-4-yl]-1H-imidazol-2-ylamino}-4-methyl-phenyl)-3-trifluoromethyl-benzamide, N-[4-methyl-3-(1-{6-[3-(4-methyl-piperazin-1-yl)-propylamino]-pyrimidin-4-yl}-1H-imidazol-2-ylamino)-phenyl]-3-trifluoromethyl-benzamide, {6-[2-(2-chloro-phenylamino)-imidazol-1-yl]-pyrimidin-4-yl}-cyclopropyl-amine, (3-{6-[2-(2-chloro-phenylamino)-imidazol-1-yl]-pyrimidin-4-yl}-phenyl)-methanol, 1-(3-{6-[2-(2-chloro-phenylamino)-imidazol-1-yl]-pyrimidin-4-ylamino}-phenyl)-ethanol, {6-[2-(2-chloro-phenylamino)-imidazol-1-yl]-pyrimidin-4-yl}-[4-(2-morpholin-4-yl-ethyl)-phenyl]-amine, {6-[2-(2-chloro-phenylamino)-imidazol-1-yl]-pyrimidin-4-yl}-(4-morpholin-4-yl-phenyl)-amine, N-(3-{6-[2-(2-chloro-phenylamino)-imidazol-1-yl]-pyrimidin-4-ylamino}-phenyl)-acetamide, 1-(3-{6-[2-(2-chloro-phenylamino)-imidazol-1-yl]-pyrimidin-4-ylamino}-propyl)-pyrrolidin-2-one, benzo[1,3]dioxol-5-yl-{6-[2-(2-chloro-phenylamino)-imidazol-1-yl]-pyrimidin-4-yl}-amine, {6-[2-(2-chloro-phenylamino)-imidazol-1-yl]-pyrimidin-4-yl}-pyridin-3-yl-amine, N-(4-methyl-3-{1-[6-(pyridin-3-ylamino)-pyrimidin-4-yl]-1H-imidazol-2-ylamino}-phenyl)-3-trifluoromethyl-benzamide, {6-[2-(2-chloro-phenylamino)-imidazol-1-yl]-pyrimidin-4-yl}-(6-methyl-pyridin-3-yl)-amine, N-(4-methyl-3-{1-[6-(6-methyl-pyridin-3-ylamino)-pyrimidin-4-yl]-1H-imidazol-2-ylamino}-phenyl)-3-trifluoromethyl-benzamide, N-{3-[1-(6-cyclopropylamino-pyrimidin-4-yl)-1H-imidazol-2-ylamino]-4-methyl-phenyl}-3-morpholin-4-yl-5-trifluoromethyl-benzamide, N-{3-[1-(6-cyclopropylamino-pyrimidin-4-yl)-1H-imidazol-2-ylamino]-4-methyl-phenyl}-3-(4-methyl-piperazin-1-yl)-5-trifluoromethyl-benzamide, N-{3-[1-(6-cyclopropylamino-pyrimidin-4-yl)-1H-imidazol-2-ylamino]-4-methyl-phenyl}-3-(4-ethyl-piperazin-1-yl)-5-trifluoromethyl-benzamide, N-{3-[1-(6-cyclopropylamino-pyrimidin-4-yl)-1H-imidazol-2-ylamino]-4-methyl-phenyl}-morpholin-4-yl-3-trifluoromethyl-benzamide, N-{3-[1-(6-cyclopropylamino-pyrimidin-4-yl)-1H-imidazol-2-ylamino]-4-methyl-phenyl}-4-(4-ethyl-piperazin-1-ylmethyl)-3-trifluoromethyl-benzamide, N-{3-[1-(6-cyclopropylamino-pyrimidin-4-yl)-1H-imidazol-2-ylamino]-4-methyl-phenyl}-4-(4-methyl-piperazin-1-ylmethyl)-3-trifluoromethyl-benzamide, N-{3-[1-(6-cyclopropylamino-pyrimidin-4-yl)-1H-imidazol-2-ylamino]-4-methyl-phenyl}-3-(4-methyl-imidazol-1-yl)-5-trifluoromethyl-benzamide, 3-(4-methyl-imidazol-1-yl)-N-{4-methyl-3-[1-(6-methylamino-pyrimidin-4-yl)-1H-imidazol-2-ylamino]-phenyl}-5-trifluoromethyl-benzamide, N-{4-methyl-3-[1-(6-methylamino-pyrimidin-4-yl)-1H-imidazol-2-ylamino]-phenyl}-4-morpholin-4-yl-3-trifluoromethyl-benzamide, 3-(4-ethyl-piperazin-1-yl)-N-{4-methyl-3-[1-(6-methylamino-pyrimidin-4-yl)-1H-imidazol-2-ylamino]-phenyl}-5-trifluoromethyl-benzamide, N-{4-methyl-3-[1-(6-methylamino-pyrimidin-4-yl)-1H-imidazol-2-ylamino]-phenyl}-3-(4-methyl-piperazin-1-yl)-5-trifluoromethyl-benzamide, N-{3-[1-(6-methylamino-pyrimidin-4-yl)-1H-imidazol-2-ylamino]-phenyl}-4-(4-methyl-piperazin-1-ylmethyl)-3-trifluoromethyl-benzamide, 3-(4-ethyl-piperazin-1-ylmethyl)-N-{4-methyl-3-[1-(6-methylamino-pyrimidin-4-yl)-1H-imidazol-2-ylamino]-phenyl}-5-trifluoromethyl-benzamide, N-{3-[1-(6-cyclopropylamino-pyrimidin-4-yl)-1H-imidazol-2-ylamino]-4-methyl-phenyl}-4-morpholin-4-ylmethyl-3-trifluoromethyl-benzamide, N-{4-methyl-3-[1-(6-methylamino-pyrimidin-4-yl)-1H-imidazol-2-ylamino]-phenyl}-4-morpholin-4-ylmethyl-3-trifluoromethyl-benzamide, N-{3-[1-(6-amino-pyrimidin-4-yl)-1H-imidazol-2-ylamino]-4-methyl-phenyl}-4-(4-ethyl-piperazin-1-ylmethyl)-3-trifluoromethyl-benzamide, N-{3-[1-(6-amino-pyrimidin-4-yl)-1H-imidazol-2-ylamino]-4-methyl-phenyl}-4-(4-methyl-piperazin-1-ylmethyl)-3-trifluoromethyl-benzamide, N-{3-[1-(6-amino-pyrimidin-4-yl)-1H-imidazol-2-ylamino]-phenyl}-3-(4-methyl-imidazol-1-yl)-5-trifluoromethyl-benzamide, N-{3-[1-(6-amino-pyrimidin-4-yl)-1H-imidazol-2-ylamino]-4-methyl-phenyl}-4-morpholin-4-yl-3-trifluoromethyl-benzamide, N-{3-[1-(6-amino-pyrimidin-4-yl)-1H-imidazol-2-ylamino]-4-methylphenyl}-3-(4-ethyl-piperazin-1-yl)-5-trifluoromethyl-benzamide, N-{3-[1-(6-amino-pyrimidin-4-yl)-1H-imidazol-2-ylamino]-4-methyl-phenyl}-3-(4-methyl-piperazin-1-yl)-5-trifluoromethyl-benzamide, N-{3-[1-(6-amino-pyrimidin-4-yl)-1H-imidazol-2-ylamino]-4-methyl-phenyl}-3-morpholin-4-ylmethyl-5-trifluoromethyl-benzamide, 3-[1-(6-cyclopropylamino-pyrimidin-4-yl)-1H-imidazol-2-ylamino]-5-methoxy-N-[4-(2-methyl-imidazol-1-yl)-3-trifluoromethyl-phenyl]-benzamide, N-{3-[1-(6-acetylamino-pyrimidin-4-yl)-1H-imidazol-2-ylamino]-4-methyl-phenyl}-3-trifluoromethyl-benzamide, N-{3-[1-(6-methanesulfonylamino-pyrimidin-4-yl)-1H-imidazol-2-ylamino]-4-methyl-phenyl}-3-trifluoromethyl-benzamide, N-{3-[1-(2-cyclopropylamino-pyrimidin-4-yl)-1H-imidazol-2-ylamino]-4-methyl-phenyl}-3-trifluoromethyl-benzamide, 3-[1-(2-cyclopropylamino-pyrimidin-4-yl)-1H-imidazol-2-ylamino]-4-methyl-N-[4-(2-methyl-imidazol-1-yl)-3-trifluoromethyl-phenyl]-benzamide, N-{3-[1-(6-cyclopropylamino-pyrimidin-4-yl)-1H-imidazol-2-ylamino]-4-methyl-phenyl}-3-piperazin-1-ylmethyl-5-trifluoromethyl-benzamide, N-{3-[1-(6-amino-pyrimidin-4-yl)-1H-imidazol-2-ylamino]-4-methyl-phenyl}-3-piperazin-1-ylmethyl-5-trifluoromethyl-benzamide, N-{3-[1-(6-cyclopropylamino-pyrimidin-4-yl)-1H-imidazol-2-ylamino]-5-methoxy-phenyl}-4-(4-methyl-piperazin-1-ylmethyl)-3-trifluoromethyl-benzamide, N-{3-[1-(6-cyclopropylamino-pyrimidin-4-yl)-1H-imidazol-2-ylamino]-5-methoxy-phenyl}-3-(4-ethyl-piperazin-1-ylmethyl)-5-trifluoromethyl-benzamide, N-{3-[1-(6-cyclopropylamino-pyrimidin-4-yl)-1H-imidazol-2-ylamino]-4-methyl-phenyl}-3-(piperidin-4-yloxy)-5-trifluoromethyl-benzamide, N-{3-[1-(6-amino-pyrimidin-4-yl)-1H-imidazol-2-ylamino]-4-methyl-phenyl}-3-(piperidin-4-yloxy)-5-trifluoromethyl-benzamide, N-{3-[1-(6-cyclopropylamino-pyrimidin-4-yl)-1H-imidazol-2-ylamino]-5-methoxy-phenyl}-3-(4-pyrrolidin-1-yl-piperidin-1-yl)-5-trifluoromethyl-benzamide, 1-{3-[1-(6-cyclopropylamino-pyrimidin-4-yl)-1H-imidazol-2-ylamino]-4-methyl-phenyl}-3-[4-(2-methyl-imidazol-1-yl)-3-trifluoromethyl-phenyl]-urea, 1-{3-[1-(6-cyclopropylamino-pyrimidin-4-yl)-1H-imidazol-2-ylamino]-4-methyl-phenyl}-3-[4-(4-ethyl-piperazin-1-ylmethyl)-3-trifluoromethyl-phenyl]-urea, pyridazine-4-carboxylic acid {3-[1-(6-cyclopropylamino-pyrimidin-4-yl)-1H-imidazol-2-ylamino]-4-methyl-phenyl}-amide, 2-chloro-N-{3-[1-(6-cyclopropylamino-pyrimidin-4-yl)-1H-imidazol-2-ylamino]-4-methyl-phenyl}-isonicotinamide, furan-2-carboxylic acid {3-[1-(6-cyclopropylamino-pyrimidin-4-yl)-1H-imidazol-2-ylamino]-4-methyl-phenyl}-amide, 1-methyl-1H-pyrrole-2-carboxylic acid {3-[1-(6-cyclopropylamino-pyrimidin-4-yl)-1H-imidazol-2-ylamino]-4-methyl-phenyl}-amide, 1H-imidazole-2-carboxylic acid {3-[1-(6-cyclopropylamino-pyrimidin-4-yl)-1H-imidazol-2-ylamino]-4-methyl-phenyl}-amide, N-{3-[1-(6-cyclopropylamino-pyrimidin-4-yl)-1H-imidazol-2-ylamino]-4-methyl-phenyl}-4-trifluoromethyl-benzamide, N-{3-[1-(6-cyclopropylamino-pyrimidin-4-yl)-1H-imidazol-2-ylamino]-4-methyl-phenyl}-6-methyl-nicotinamide, 1-tert-butyl-5-methyl-1H-pyrazole-3-carboxylic acid {3-[1-(6-cyclopropylamino-pyrimidin-4-yl)-1H-imidazol-2-ylamino]-4-methyl-phenyl}-amide, N-[4-(4-ethyl-piperazin-1-ylmethyl)-3-trifluoromethyl-phenyl]-4-methyl-3-{1-[6-(2-morpholin-4-yl-ethylamino)-pyrimidin-4-yl]-1H-imidazol-2-ylamino}-benzamide, 3-(4-methyl-imidazol-1-yl)-N-(4-methyl-3-{1-[6-(2-morpholin-4-yl-ethylamino)-pyrimidin-4-yl]-1H-imidazol-2-ylamino}-phenyl)-5-trifluoromethyl-benzamide, 4-methyl-N-[4-(2-methyl-imidazol-1-yl)-3-trifluoromethyl-phenyl]-3-{1-[6-(2-morpholin-4-yl-ethylamino)-pyrimidin-4-yl]-1H-imidazol-2-ylamino}-benzamide, N-(4-methyl-3-{1-[6-(2-morpholin-4-yl-ethylamino)-pyrimidin-4-yl]-1H-imidazol-2-ylamino}-phenyl)-3-(1-methyl-piperidin-4-yloxy)-5-trifluoromethyl-benzamide, pyrazine-2-carboxylic acid {3-[1-(6-cyclopropylamino-pyrimidin-4-yl)-1H-imidazol-2-ylamino]-4-methyl-phenyl}-amide, 5-methyl-pyrazine-2-carboxylic acid {3-[1-(6-cyclopropylamino-pyrimidin-4-yl)-1H-imidazol-2-ylamino]-4-methyl-phenyl}-amide, quinoxaline-6-carboxylic acid {3-[1-(6-cyclopropylamino-pyrimidin-4-yl)-1H-imidazol-2-ylamino]-4-methyl-phenyl}-amide, 5-tert-butyl-2-methyl-4-morpholin-4-ylmethyl-furan-3-carboxylic acid {3-[1-(6-cyclopropylamino-pyrimidin-4-yl)-1H-imidazol-2-ylamino]-4-methyl-phenyl}-amide, 5-tert-butyl-2-methyl-2H-pyrazole-3-carboxylic acid {3-[1-(6-cyclopropylamino-pyrimidin-4-yl)-1H-imidazol-2-ylamino]-4-methyl-phenyl}-amide, 2-benzyl-5-tert-butyl-2H-pyrazole-3-carboxylic acid {3-[1-(6-cyclopropylamino-pyrimidin-4-yl)-1H-imidazol-2-ylamino]-4-methyl-phenyl}-amide, N-{3-[1-(6-cyclopropylamino-pyrimidin-4-yl)-1H-imidazol-2-ylamino]-4-methyl-phenyl}-3-(piperidin-4-ylamino)-5-trifluoromethyl-benzamide, N-{3-[1-(6-cyclopropylamino-pyrimidin-4-yl)-1H-imidazol-2-ylamino]-4-methyl-phenyl}-3-(pyrrolidin-2-ylmethoxy)-5-trifluoromethyl-benzamide, 5-tert-butyl-2-methyl-furan-3-carboxylic acid {3-[1-(6-cyclopropylamino-pyrimidin-4-yl)-1H-imidazol-2-ylamino]-4-methyl-phenyl}-amide, 5-tert-butyl-3-methyl-furan-2-carboxylic acid {3-[1-(6-cyclopropylamino-pyrimidin-4-yl)-1H-imidazol-2-ylamino]-4-methyl-phenyl}-amide, 5-tert-butyl-2-diethylamino-furan-3-carboxylic acid {3-[1-(6-cyclopropylamino-pyrimidin-4-yl)-1H-imidazol-2-ylamino]-4-methyl-phenyl}-amide, 5-tert-butyl-4-diethylamino-2-methyl-furan-3-carboxylic acid {3-[1-(6-cyclopropylamino-pyrimidin-4-yl)-1H-imidazol-2-ylamino]-4-methyl-phenyl}-amide, 5-tert-butyl-thiophene-2-carboxylic acid {3-[1-(6-cyclopropylamino-pyrimidin-4-yl)-1H-imidazol-2-ylamino]-4-methyl-phenyl}-amide, 5-tert-butyl-3-methyl-furan-2-carboxylic acid (4-methyl-3-{1-[6-(2-morpholin-4-yl-ethylamino)-pyrimidin-4-yl]-1H-imidazol-2-ylamino}-phenyl)-amide, 5-tert-butyl-thiophene-2-carboxylic acid (4-methyl-3-{1-[6-(2-morpholin-4-yl-ethylamino)-pyrimidin-4-yl]-1H-imidazol-2-ylamino}-phenyl)-amide, 5-tert-butyl-2-methyl-furan-3-carboxylic acid (4-methyl-3-{1-[6-(2-morpholin-4-yl-ethylamino)-pyrimidin-4-yl]-1H-imidazol-2-ylamino}-phenyl)-amide, N-(3-{1-[6-(4-amino-cyclohexylamino)-pyrimidin-4-yl]-1H-imidazol-2-ylamino}-4-methyl-phenyl)-3-trifluoromethyl-benzamide, N-(4-methyl-3-{1-[6-(piperidin-4-ylamino)-pyrimidin-4-yl]-1H-imidazol-2-ylamino}-phenyl)-3-trifluoromethyl-benzamide, N-[4-methyl-3-(1-{6-[2-(4-methyl-piperazin-1-yl)-ethylamino]-pyrimidin-4-yl}-1H-imidazol-2-ylamino)-phenyl]-3-trifluoromethyl-benzamide, N-(3-{1-[6-(2,5-dimethyl-2H-pyrazol-3-ylamino)-pyrimidin-4-yl]-1H-imidazol-2-ylamino}-4-methyl-phenyl)-3-trifluoromethyl-benzamide, N-(4-methyl-3-{1-[6-(4-methyl-piperazin-1-ylamino)-pyrimidin-4-yl]-1H-imidazol-2-ylamino}-phenyl)-3-trifluoromethyl-benzamide, N-(4-methyl-3-{1-[6-(2-methyl-2H-pyrazol-3-ylamino)-pyrimidin-4-yl]-1H-imidazol-2-ylamino}-phenyl)-3-trifluoromethyl-benzamide, N-(3-{1-[6-(2,6-dimethyl-pyridin-3-ylamino)-pyrimidin-4-yl]-1H-imidazol-2-ylamino}-4-methyl-phenyl)-3-trifluoromethyl-benzamide, N-(4-methyl-3-{1-[6-(2-methyl-pyridin-3-ylamino)-pyrimidin-4-yl]-1H-imidazol-2-ylamino}-phenyl)-3-trifluoromethyl-benzamide, N-{3-[1-(6-cyclopropylamino-pyrimidin-4-yl)-1H-imidazol-2- ylamino]-4-methyl-phenyl}-3-(4-methyl-piperazin-1-yl)-5-trifluoromethyl-benzamide, N-{3-[1-(6-cyclopropylamino-pyrimidin-4-yl)-1H-imidazol-2-ylamino]-4-methyl-phenyl}-3-[4-(2-hydroxy-ethyl)-piperazin-1-yl]-5-trifluoromethyl-benzamide, N-{3-[1-(6-cyclopropylamino-pyrimidin-4-yl)-1H-imidazol-2-ylamino]-4-methyl-phenyl}-3-piperazin-1-yl-5-trifluoromethyl-benzamide, N-{4-chloro-3-[1-(6-cyclopropylamino-pyrimidin-4-yl)-1H-imidazol-2-ylamino]-phenyl}-benzamide, N-{3-[1-(6-cyclopropylamino-pyrimidin-4-yl)-1H-imidazol-2-ylamino]-4-fluoro-phenyl}-benzamide, N-{3-[1-(6-cyclopropylamino-pyrimidin-4-yl)-1H-imidazol-2-ylamino]-2-methyl-phenyl}-benzamide, N-{5-[1-(6-cyclopropylamino-pyrimidin-4-yl)-1H-imidazol-2-ylamino]-2-fluoro-phenyl}-benzamide, N-{5-[1-(6-cyclopropylamino-pyrimidin-4-yl)-1H-imidazol-2-ylamino]-2-methyl-phenyl}-benzamide, N-{4-chloro-3-[1-(6-cyclopropylamino-pyrimidin-4-yl)-1H-imidazol-2-ylamino]-phenyl}-4-morpholin-4-ylmethyl-3-trifluoromethyl-benzamide, N-{3-[1-(6-cyclopropylamino-pyrimidin-4-yl)-1H-imidazol-2-ylamino]-4-fluoro-phenyl}-4-morpholin-4-ylmethyl-3-trifluoromethyl-benzamide, N-{3-[1-(6-cyclopropylamino-pyrimidin-4-yl)-1H-imidazol-2-ylamino]-2-methyl-phenyl}-4-morpholin-4-ylmethyl-3-trifluoromethyl-benzamide, N-{4-chloro-3-[1-(6-cyclopropylamino-pyrimidin-4-yl)-1H-imidazol-2-ylamino]-phenyl}-3-(4-methyl-imidazol-1-yl)-5-trifluoromethyl-benzamide, N-{3-[1-(6-cyclopropylamino-pyrimidin-4-yl)-1H-imidazol-2-ylamino]-4-fluoro-phenyl}-3-(4-methyl-imidazol-1-yl)-5-trifluoromethyl-benzamide, N-{3-[1-(6-cyclopropylamino-pyrimidin-4-yl)-1H-imidazol-2-ylamino]-2-methyl-phenyl}-3-(4-methyl-imidazol-1-yl)-5-trifluoromethyl-benzamide, N-{5-[1-(6-cyclopropylamino-pyrimidin-4-yl)-1H-imidazol-2-ylamino]-2-fluoro-phenyl}-3-(4-methyl-imidazol-1-yl)-5-trifluoromethyl-benzamide, N-{5-[1-(6-cyclopropylamino-pyrimidin-4-yl)-1H-imidazol-2-ylamino]-2-methyl-phenyl}-3-(4-methyl-imidazol-1-yl)-5-trifluoromethyl-benzamide, N-{3-[1-(6-cyclopropylamino-pyrimidin-4-yl)-1H-imidazol-2-ylamino]4-methoxy-phenyl}-benzamide, N-{3-[1-(6-cyclopropylamino-pyrimidin-4-yl)-1H-imidazol-2-ylamino]-4-methyl-phenyl}-3-trifluoromethyl-benzenesulfonamide, 3-[1-(6-cyclopropylamino-pyrimidin-4-yl)-1H-imidazol-2-ylamino]-4-methyl-N-(3-trifluoromethyl-phenyl)-benzenesulfonamide, N-{3-[1-(6-cyclopropylamino-pyrimidin-4-yl)-1H-imidazol-2-ylamino]-4-fluoro-phenyl}-3-dimethylamino-5-trifluoromethyl-benzamide, N-{5-[1-(6-cyclopropylamino-pyrimidin-4-yl)-1H-imidazol-2-ylamino]-2-methyl-phenyl}-3-dimethylamino-5-trifluoromethyl-benzamide, N-{4-chloro-3-[1-(6-cyclopropylamino-pyrimidin-4-yl)-1H-imidazol-2-ylamino]-phenyl}-3-dimethylamino-5-trifluoromethyl-benzamide, 3-(4-methyl-imidazol-1-yl)-N-(4-methyl-3-{1-[6-(pyridin-2-ylamino)-pyrimidin-4-yl]-1H-imidazol-2-ylamino}-phenyl)-5-trifluoromethyl-benzamide, 4-(4-ethyl-piperazin-1-ylmethyl)-N-(4-methyl-3-{1-[6-(pyridin-2-ylamino)-pyrimidin-4-yl]-1H-imidazol-2-ylamino}-phenyl)-3-trifluoromethyl-benzamide, 3-(4-ethyl-piperazin-1-yl)-N-(4-methyl-3-{1-[6-(pyridin-2-ylamino)-pyrimidin-4-yl]-1H-imidazol-2-ylamino}-phenyl)-5-trifluoromethyl-benzamide, 4-chloro-N-(4-methyl-3-{1-[6-(pyridin-2-ylamino)-pyrimidin-4-yl]-1H-imidazol-2-ylamino}-phenyl)-3-trifluoromethyl-benzamide, N-[3-(1-{6-[5-(4-ethyl-piperazin-1-yl)-pyridin-2-ylamino]-pyrimidin-4-yl}-1H-imidazol-2-ylamino)-4-methyl-phenyl]-3-trifluoromethyl-benzamide, N-(4-methyl-3-{1-[6-(4-methyl-pyridin-2-ylamino)-pyrimidin-4-yl]-1H-imidazol-2-ylamino}-phenyl)-3-trifluoromethyl-benzamide, N-(3-{1-[6-(4,6-dimethyl-pyridin-2-ylamino)-pyrimidin-4-yl]-1H-imidazol-2-ylamino}-4-methyl-phenyl)-3-trifluoromethyl-benzamide, 6-(6-{2-[2-methyl-5-(3-trifluoromethyl-benzoylamino)-phenylamino]-imidazol-1-yl}-pyrimidin-4-ylamino)-nicotinamide, N-(4-methyl-3-{1-[6-(5-methyl-pyridin-2-ylamino)-pyrimidin-4-yl]-1H-imidazol-2-ylamino}-phenyl)-3-trifluoromethyl-benzamide, N-(3-{1-[6-(5-cyano-pyridin-2-ylamino)-pyrimidin-4-yl]-1H-imidazol-2-ylamino}-4-methyl-phenyl)-3-trifluoromethyl-benzamide, 4-chloro-N-{3-[1-(6-cyclopropylamino-pyrimidin-4-yl)-1H-imidazol-2-ylamino]-4-methyl-phenyl}-3-trifluoromethyl-benzamide, 4-chloro-N-(4-methyl-3-{1-[6-(2-morpholin-4-yl-ethylamino)-pyrimidin-4-yl]-1H-imidazol-2-ylamino}-phenyl)-3-trifluoromethyl-benzamide, 5-tert-butyl-2-methyl-2H-pyrazole-3-carboxylic acid (4-methyl-3-{1-[6-(2-morpholin-4-yl-ethylamino)-pyrimidin-4-yl]-1H-imidazol-2-ylamino}-phenyl)-amide, N-(3-{1-[6-(2-dimethylamino-ethylamino)-pyrimidin-4-yl]-1H-imidazol-2-ylamino}-4-methyl-phenyl)-3-trifluoromethyl-benzamide, N-(4-methyl-3-{1-[6-(3-morpholin-4-yl-propylamino)-pyrimidin-4-yl]-1H-imidazol-2-ylamino}-phenyl)-3-trifluoromethyl-benzamide, N-(3-{1-[6-(2-methoxy-ethylamino)-pyrimidin-4-yl]-1H-imidazol-2-ylamino}-4-methyl-phenyl)-3-trifluoromethyl-benzamide, N-[4-methyl-3-(1-{6-[2-(1-methyl-pyrrolidin-2-yl)-ethylamino]-pyrimidin-4-yl}-1H-imidazol-2-ylamino)-phenyl]-3-trifluoromethyl-benzamide, N-(4-methyl-3-{1-[6-(pyridin-2-ylamino)-pyrimidin-4-yl]-1H-imidazol-2-ylamino}-phenyl)-3-trifluoromethyl-benzamide, N-[4-methyl-3-(1-pyrimidin-4-yl-1H-imidazol-2-ylamino)-phenyl]-3-trifluoromethyl-benzamide, N-[4-methyl-3-(1-pyrimidin-2-yl-1H-imidazol-2-ylamino)-phenyl]-3-trifluoromethyl-benzamide, N-{4-methyl-3-[1-(4-methylamino-pyrimidin-2-yl)-1H-imidazol-2-ylamino]-phenyl}-3-trifluoromethyl-benzamide, N-{4-methyl-3-[1-(2-methylamino-pyrimidin-4-yl)-1H-imidazol-2-ylamino]-phenyl}-3-trifluoromethyl-benzamide, N-(4-methyl-3-{1-[4-(2-morpholin-4-yl-ethylamino)-pyrimidin-2-yl]-1H-imidazol-2-ylamino}-phenyl)-3-trifluoromethyl-benzamide, N-(4-methyl-3-{1-[2-(2-morpholin-4-yl-ethylamino)-pyrimidin-4-yl]-1H-imidazol-2-ylamino}-phenyl)-3-trifluoromethyl-benzamide, N-(3-{1-[6-(2-ethyl-2H-pyrazol-3-ylamino)-pyrimidin-4-yl]-1H-imidazol-2-ylamino}-4-methyl-phenyl)-3-trifluoromethyl-benzamide, N-(3-{1-[6-(3-dimethylamino-propylamino)-pyrimidin-4-yl]-1H-imidazol-2-ylamino}-4-methyl-phenyl)-3-trifluoromethyl-benzamide, N-{3-[1-(6-isopropylamino-pyrimidin-4-yl)-1H-imidazol-2-ylamino]-4-methyl-phenyl}-3-trifluoromethyl-benzamide, N-[3-(1-{6-[(furan-3-ylmethyl)-amino]-pyrimidin-4-yl}-1H-imidazol-2-ylamino)-4-methyl-phenyl]-3-trifluoromethyl-benzamide, N-[4-methyl-3-(1-{6-[3-(4-methyl-piperazin-1-yl)-propylamino]-pyrimidin-4-yl}-1H-imidazol-2-ylamino)-phenyl]-3-trifluoromethyl-benzamide, N-[3-(1-{6-[(benzo[1,3]dioxol-5-ylmethyl)-amino]-pyrimidin-4-yl}1H-imidazol-2-ylamino)-4-methyl-phenyl]-3-trifluoromethyl-benzamide, N-(4-methyl-3-{1-[6-(2-methyl-6-morpholin-4-yl-pyridin-3-ylamino)-pyrimidin-4-yl]-1H-imidazol-2-ylamino}-phenyl)-3-trifluoromethyl-benzamide, N-(4-methyl-3-{1-[6-(4-methyl-pyrimidin-2-ylamino)-pyrimidin-4-yl]-1H-imidazol-2-ylamino}-phenyl)-3-trifluoromethyl-benzamide, N-(3-{1-[6-(6-methoxy-pyridin-3-ylamino)-pyrimidin-4-yl]-1H-imidazol-2-ylamino}-4-methyl-phenyl)-3-trifluoromethyl-benzamide, N-{4-methyl-3-[1-(6-morpholin-4-yl-pyrimidin-4-yl)-1H-imidazol-2-ylamino]-phenyl}-3-trifluoromethyl-benzamide, N-(3-{1-[6-(4-ethyl-piperazin-1-yl)-pyrimidin-4-yl]-1H-imidazol-2-ylamino}-

4-methyl-phenyl)-3-trifluoromethyl-benzamide, N-(3-{1-[6-(3-fluoro-phenylamino)-pyrimidin-4-yl]-1H-imidazol-2-ylamino}-4-methyl-phenyl)-3-trifluoromethyl-benzamide, N-(3-{1-[6-(3-dimethylamino-ethyl-formamide-phenylamino)-pyrimidin-4-yl]-1H-imidazol-2-ylamino}-4-methyl-phenyl)-3-trifluoromethyl-benzamide, N-[4-methyl-3-(1-{6-[(pyridin-3-ylmethyl)-amino]-pyrimidin-4-yl}-1H-imidazol-2-ylamino)-phenyl]-3-trifluoromethyl-benzamide, N-[4-methyl-3-(1-{6-[(pyridin-4-ylmethyl)-amino]-pyrimidin-4-yl}-1H-imidazol-2-ylamino)-phenyl]-3-trifluoromethyl-benzamide, N-(4-methyl-3-{1-[6-(4-morpholin-4-yl-piperidin-1-yl)-pyrimidin-4-yl]-1H-imidazol-2-ylamino}-phenyl)-3-trifluoromethyl-benzamide, N-[4-methyl-3-(1-{6-[(thiazol-2-ylmethyl)-amino]-pyrimidin-4-yl}-1H-imidazol-2-ylamino)-phenyl]-3-trifluoromethyl-benzamide, N-[4-methyl-3-(1-{6-[(pyridin-2-ylmethyl)-amino]-pyrimidin-4-yl}-1H-imidazol-2-ylamino)-phenyl]-3-trifluoromethyl-benzamide, N-[4-methyl-3-(1-{6-[(6-methyl-pyrazin-2-ylmethyl)-amino]-pyrimidin-4-yl}-1H-imidazol-2-ylamino)-phenyl]-3-trifluoromethyl-benzamide, N-(4-methyl-3-{1-[6-(4-pyridin-2-yl-piperazin-1-yl)-pyrimidin-4-yl]-1H-imidazol-2-ylamino}-phenyl)-3-trifluoromethyl-benzamide, N-(3-{1-[6-(3-imidazol-1-yl-propylamino)-pyrimidin-4-yl]-1H-imidazol-2-ylamino}-4-methyl-phenyl)-3-trifluoromethyl-benzamide, N-(4-methyl-3-{1-[6-(pyrazin-2-ylamino)-pyrimidin-4-yl]-1H-imidazol-2-ylamino}-phenyl)-3-trifluoromethyl-benzamide, N-(3-{1-[6-(3-formamide-phenylamino)-pyrimidin-4-yl]-1H-imidazol-2-ylamino}-4-methyl-phenyl)-3-trifluoromethyl-benzamide, 4-methyl-3-{1-[6-(2-morpholin-4-yl-ethylamino)-pyrimidin-4-yl]-1H-imidazol-2-ylamino}-N-(3-trifluoromethyl-phenyl)-benzamide, 4-methyl-3-{1-[6-(4-methyl-piperazin-1-ylamino)-pyrimidin-4-yl]-1H-imidazol-2-ylamino}-N-(3-trifluoromethyl-phenyl)-benzamide, N-(4-chloro-3-trifluoroethyl-phenyl)-4-methyl-3-{1-[6-(2-morpholin-4-yl-ethylamino)-pyrimidin-4-yl]-1H-imidazol-2-ylamino}-benzamide, N-(4-chloro-3-trifluoromethyl-phenyl)-4-methyl-3-{1-[6-(4-m ethyl-piperazin-1-ylamino)-pyrimidin-4-yl]-1H-imidazol-2-ylamino}-benzamide, 1-tert-butyl-5-(4-methyl-piperazin-1-ylmethyl)-1H-pyrazole-3-carboxylic acid {3-[1-(6-cyclopropylamino-pyrimidin-4-yl)-1H-imidazol-2-ylamino]-4-methyl-phenyl}-amide, 1-tert-butyl-5-morpholin-4-ylmethyl-1H-pyrazole-3-carboxylic acid {3-[1-(6-cyclopropylamino-pyrimidin-4-yl)-1H-imidazol-2-ylamino]-4-methyl-phenyl}-amide, N-(4-tert-butyl-thiazol-2-yl)-4-methyl-3-{1-[6-(2-morpholin-4-yl-ethylamino)-pyrimidin-4-yl]-1H-imidazol-2-ylamino}-benzamide, N-(4-tert-butyl-thiazol-2-yl)-4-methyl-3-{1-[6-(4-methyl-piperazin-1-ylamino)-pyrimidin-4-yl]-1H-imidazol-2-ylamino}-benzamide, N-(5-tert-butyl-2-methyl-2H-pyrazol-3-yl)-4-methyl-3-{1-[6-(4-methyl-piperazin-1-ylamino)-pyrimidin-4-yl]-1H-imidazol-2-ylamino}-benzamide, N-(4-methyl-3-{1-[6-(4-methyl-piperazin-1-ylamino)-pyrimidin-4-yl]-1H-imidazol-2-ylamino}-phenyl)-benzamide, N-(5-tert-butyl-2-methyl-2H-pyrazol-3-yl)-4-methyl-3-{1-[6-(2-morpholin-4-yl-ethylamino)-pyrimidin-4-yl]-1H-imidazol-2-ylamino}-benzamide, N-(4-methyl-3-{1-[2-(2-morpholin-4-yl-ethylamino)-pyridin-4-yl]-1H-imidazol-2-ylamino}-phenyl)-3-trifluoromethyl-benzamide, N-{3-[1-(4-acetylamino-pyridin-2-yl)-1H-imidazol-2-ylamino]-4-methyl-phenyl}-3-trifluoromethyl-benzamide and 2-{2-[2-Methyl-5-(3-trifluoromethyl-benzoylamino)-phenylamino]-imidazol-1-yl}-isonicotinamide.

Further preferred compounds of the invention are detailed in the Examples and Table I, infra.

Pharmacology and Utility

Compounds of the invention modulate the activity of kinases and, as such, are useful for treating diseases or disorders in which kinases, contribute to the pathology and/or symptomology of the disease. Examples of kinases that are inhibited by the compounds and compositions described herein and against which the methods described herein are useful include, but are not limited to, Abl, BCR-Abl (wild-type and mutant forms), PDGF-R, trkB, c-SRC, BMX, FGFR3, b-RAF, SGK, Tie2, Lck, JNK2α2, MKK4, c-RAF, MKK6, SAPK2α and SAPK2β.

Abelson tyrosine kinase (i.e. Abl, c-Abl) is involved in the regulation of the cell cycle, in the cellular response to genotoxic stress, and in the transmission of information about the cellular environment through integrin signaling. Overall, it appears that the Abl protein serves a complex role as a cellular module that integrates signals from various extracellular and intracellular sources and that influences decisions in regard to cell cycle and apoptosis. Abelson tyrosine kinase includes sub-types derivatives such as the chimeric fusion (oncoprotein) BCR-Abl with deregulated tyrosine kinase activity or the v-Abl. BCR-Abl is critical in the pathogenesis of 95% of chronic myelogenous leukemia (CML) and 10% of acute lymphocytic leukemia. STI-571 (Gleevec) is an inhibitor of the oncogenic BCR-Abl tyrosine kinase and is used for the treatment of chronic myeloid leukemia (CML). However, some patients in the blast crisis stage of CML are resistant to STI-571 due to mutations in the BCR-Abl kinase. Over 22 mutations have been reported to date with the most common being G250E, E255V, T315I, F317L and M351T.

Compounds of the present invention inhibit abl kinase, especially v-abl kinase. The compounds of the present invention also inhibit wild-type BCR-Abl kinase and mutations of BCR-Abl kinase and are thus suitable for the treatment of Bcr-abl-positive cancer and tumor diseases, such as leukemias (especially chronic myeloid leukemia and acute lymphoblastic leukemia, where especially apoptotic mechanisms of action are found), and also shows effects on the subgroup of leukemic stem cells as well as potential for the purification of these cells in vitro after removal of said cells (for example, bone marrow removal) and reimplantation of the cells once they have been cleared of cancer cells (for example, reimplantation of purified bone marrow cells).

The Ras-Raf-MEK-ERK signaling pathway mediates cellular response to growth signals. Ras is mutated to an oncogenic form in ~15% of human cancer. The Raf family belongs to the serine/threonine protein kinase and it includes three members, A-Raf, B-Raf and c-Raf (or Raf-1). The focus on Raf being a drug target has centered on the relationship of Raf as a downstream effector of Ras. However, recent data suggests that B-Raf may have a prominent role in the formation of certain tumors with no requirement for an activated Ras allele (Nature 417, 949-954 (1 Jul. 2002). In particular, B-Raf mutations have been detected in a large percentage of malignant melanomas.

Existing medical treatments for melanoma are limited in their effectiveness, especially for late stage melanomas. The compounds of the present invention also inhibit cellular processes involving b-Raf kinase, providing a new therapeutic opportunity for treatment of human cancers, especially for melanoma.

The compounds of the present invention also inhibit cellular processes involving c-Raf kinase. c-Raf is activated by the ras oncogene, which is mutated in a wide number of human cancers. Therefore inhibition of the kinase activity of c-Raf may provide a way to prevent ras mediated tumor growth [Campbell, S. L., Oncogene, 17, 1395 (1998)].

PDGF (Platelet-derived Growth Factor) is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis. Compounds of the invention can inhibit PDGF receptor (PDGFR) activity and are, therefore, suitable for the treatment of tumor diseases, such as gliomas, sarcomas, prostate tumors, and tumors of the colon, breast, and ovary.

Compounds of the present invention, can be used not only as a tumor-inhibiting substance, for example in small cell lung cancer, but also as an agent to treat non-malignant proliferative disorders, such as atherosclerosis, thrombosis, psoriasis, scleroderma and fibrosis, as well as for the protection of stem cells, for example to combat the hemotoxic effect of chemotherapeutic agents, such as 5-fluoruracil, and in asthma. Compounds of the invention can especially be used for the treatment of diseases, which respond to an inhibition of the PDGF receptor kinase.

Compounds of the present invention show useful effects in the treatment of disorders arising as a result of transplantation, for example, allogenic transplantation, especially tissue rejection, such as especially obliterative bronchiolitis (OB), i.e. a chronic rejection of allogenic lung transplants. In contrast to patients without OB, those with OB often show an elevated PDGF concentration in bronchoalveolar lavage fluids.

Compounds of the present invention are also effective in diseases associated with vascular smooth-muscle cell migration and proliferation (where PDGF and PDGF-R often also play a role), such as restenosis and atherosclerosis. These effects and the consequences thereof for the proliferation or migration of vascular smooth-muscle cells in vitro and in vivo can be demonstrated by administration of the compounds of the present invention, and also by investigating its effect on the thickening of the vascular intima following mechanical injury in vivo.

The trk family of neurotrophin receptors (trkA, trkB, trkC) promotes the survival, growth and differentiation of the neuronal and non-neuronal tissues. The trkB protein is expressed in neuroendocrine-type cells in the small intestine and colon, in the alpha cells of the pancreas, in the monocytes and macrophages of the lymph nodes and of the spleen, and in the granular layers of the epidermis (Shibayama and Koizumi, 1996). Expression of the TrkB protein has been associated with an unfavorable progression of Wilms tumors and of neuroblastomas. TkrB is, moreover, expressed in cancerous prostate cells but not in normal cells. The signaling pathway downstream of the trk receptors involves the cascade of MAPK activation through the Shc, activated Ras, ERK-1 and ERK-2 genes, and the PLC-gammal transduction pathway (Sugimoto et al., 2001).

The kinase, c-Src transmits oncogenic signals of many receptors. For example, over-expression of EGFR or HER2/neu in tumors leads to the constitutive activation of c-src, which is characteristic for the malignant cell but absent from the normal cell. On the other hand, mice deficient in the expression of c-src exhibit an osteopetrotic phenotype, indicating a key participation of c-src in osteoclast function and a possible involvement in related disorders.

The Tec family kinase, Bmx, a non-receptor protein-tyrosine kinase, controls the proliferation of mammary epithelial cancer cells.

Fibroblast growth factor receptor 3 was shown to exert a negative regulatory effect on bone growth and an inhibition of chondrocyte proliferation. Thanatophoric dysplasia is caused by different mutations in fibroblast growth factor receptor 3, and one mutation, TDII FGFR3, has a constitutive tyrosine kinase activity which activates the transcription factor Stat1, leading to expression of a cell-cycle inhibitor, growth arrest and abnormal bone development (Su et al., Nature, 1997, 386, 288-292). FGFR3 is also often expressed in multiple myeloma-type cancers. Inhibitors of FGFR3 activity are useful in the treatment of T-cell mediated inflammatory or autoimmune diseases including but not limited to rheumatoid arthritis (RA), collagen II arthritis, multiple sclerosis (MS), systemic lupus erythematosus (SLE), psoriasis, juvenile onset diabetes, Sjogren's disease, thyroid disease, sarcoidosis, autoimmune uveitis, inflammatory bowel disease (Crohn's and ulcerative colitis), celiac disease and myasthenia gravis.

The activity of serum and glucocorticoid-regulated kinase (SGK), is correlated to perturbed ion-channel activities, in particular, those of sodium and/or potassium channels and compounds of the invention can be useful for treating hypertension.

Lin et al (1997) J. Clin. Invest. 100, 8: 2072-2078 and P. Lin (1998) PNAS 95, 8829-8834, have shown an inhibition of tumor growth and vascularization and also a decrease in lung metastases during adenoviral infections or during injections of the extracellular domain of Tie-2 (Tek) in breast tumor and melanoma xenograft models. Tie2 inhibitors can be used in situations where neovascularization takes place inappropriately (i.e. in diabetic retinopathy, chronic inflammation, psoriasis, Kaposi's sarcoma, chronic neovascularization due to macular degeneration, rheumatoid arthritis, infantile haemangioma and cancers).

Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis.

JNKs, along with other MAPKs, have been implicated in having a role in mediating cellular response to lancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, cancer and neurodegenerative diseases. As a result of the importance of JNK activation associated with liver disease or episodes of hepatic ischemia, compounds of the invention may also be useful to treat various hepatic disorders. A role for JNK in cardiovascular disease such as myocardial infarction or congestive heart failure has also been reported as it has been shown JNK mediates hypertrophic responses to various forms of cardiac stress. It has been demonstrated that the JNK cascade also plays a role in T-cell activation, including activation of the IL-2 promoter. Thus, inhibitors of JNK may have therapeutic value in altering pathologic immune responses. A role for JNK activation in various cancers has also been established, suggesting the potential use of JNK inhibitors in cancer. For example, constitutively activated JNK is associated with HTLV-1 mediated tumorigenesis [Oncogene 13:135-42 (1996)]. JNK may play a role in Kaposi's sarcoma (KS). Other proliferative effects of other cytokines implicated in KS proliferation, such as vascular endothelial growth factor (VEGF), IL-6 and TNFα, may also be mediated by JNK. In addition, regulation of the c-jun gene in p210 BCR-ABL transformed cells corresponds with activity of JNK, suggesting a role for JNK inhibitors in the treatment for chronic myelogenous leukemia (CML) [Blood 92:2450-60 (1998)].

Certain abnormal proliferative conditions are believed to be associated with raf expression and are, therefore, believed to be responsive to inhibition of raf expression. Abnormally high levels of expression of the raf protein are also implicated in transformation and abnormal cell proliferation. These abnormal proliferative conditions are also believed to be responsive to inhibition of raf expression. For example, expression of the c-raf protein is believed to play a role in abnormal cell proliferation since it has been reported that 60% of all lung carcinoma cell lines express unusually high levels of c-raf mRNA and protein. Further examples of abnormal proliferative conditions are hyper-proliferative disorders such as cancers, tumors, hyperplasia, pulmonary fibrosis, angiogenesis, psoriasis, atherosclerosis and smooth muscle cell proliferation in the blood vessels, such as stenosis or restenosis following angioplasty. The cellular signaling pathway of which raf is a part has also been implicated in inflammatory disorders characterized by T-cell proliferation (T-cell activation and growth), such as tissue graft rejection, endotoxin shock, and glomerular nephritis, for example.

The stress activated protein kinases (SAPKs) are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults. Therefore, agents that inhibit SAPK activity in a cell prevent DNA repair and sensitize the cell to agents that induce DNA damage or inhibit DNA synthesis and induce apoptosis of a cell or that inhibit cell proliferation.

Mitogen-activated protein kinases (MAPKs) are members of conserved signal transduction pathways that activate transcription factors, translation factors and other target molecules in response to a variety of extracellular signals. MAPKs are activated by phosphorylation at a dual phosphorylation motif having the sequence Thr-X-Tyr by mitogen-activated protein kinase kinases (MKKs). In higher eukaryotes, the physiological role of MAPK signaling has been correlated with cellular events such as proliferation, oncogenesis, development and differentiation. Accordingly, the ability to regulate signal transduction via these pathways (particularly via MKK4 and MKK6) could lead to the development of treatments and preventive therapies for human diseases associated with MAPK signaling, such as inflammatory diseases, autoimmune diseases and cancer.

The family of human ribosomal S6 protein kinases consists of at least 8 members (RSK1, RSK2, RSK3, RSK4, MSK1, MSK2, p70S6K and p70S6 Kb). Ribosomal protein S6 protein kinases play important pleotropic functions, among them is a key role in the regulation of mRNA translation during protein biosynthesis (Eur. J. Biochem 2000 November; 267 (21): 6321-30, Exp Cell Res. Nov. 25, 1999; 253 (1):100-9, Mol Cell Endocrinol. May 25, 1999; 151(1-2):65-77). The phosphorylation of the S6 ribosomal protein by p70S6 has also been implicated in the regulation of cell motility (Immunol. Cell Biol. 2000 August; 78(4):447-51) and cell growth (Prog. Nucleic Acid Res. Mol. Biol., 2000; 65:101-27), and hence, may be important in tumor metastasis, the immune response and tissue repair as well as other disease conditions.

The SAPK's (also called "jun N-terminal kinases" or "JNK's") are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults.

Agents that inhibit SAPK activity in a cell prevent DNA repair and sensitize the cell to those cancer therapeutic modalities that act by inducing DNA damage.

BTK plays a role in autoimmune and/or inflammatory disease such as systemic lupus erythematosus (SLE), rheumatoid arthritis, multiple vasculitides, idiopathic thrombocytopenic purpura (ITP), myasthenia gravis, and asthma. Because of BTK's role in B-cell activation, inhibitors of BTK are useful as inhibitors of B-cell mediated pathogenic activity, such as autoantibody production, and are useful for the treatment of B-cell lymphoma and leukemia.

CHK2 is a member of the checkpoint kinase family of serine/threonine protein kinases and is involved in a mechanism used for surveillance of DNA damage, such as damage caused by environmental mutagens and endogenous reactive oxygen species. As a result, it is implicated as a tumor suppressor and target for cancer therapy.

CSK influences the metastatic potential of cancer cells, particularly colon cancer.

Fes is a non-receptor protein tyrosine kinase that has been implicated in a variety of cytokine signal transduction pathways, as well as differentiation of myeloid cells. Fes is also a key component of the granulocyte differentiation machinery.

Flt3 receptor tyrosine kinase activity is implicated in leukemias and myelodysplastic syndrome. In approximately 25% of AML the leukemia cells express a constitutively active form of auto-phosphorylated (p) FLT3 tyrosine kinase on the cell surface. The activity of p-FLT3 confers growth and survival advantage on the leukemic cells. Patients with acute leukemia, whose leukemia cells express p-FLT3 kinase activity, have a poor overall clinical outcome. Inhibition of p-FLT3 kinase activity induces apoptosis (programmed cell death) of the leukemic cells.

Inhibitors of IKKα and IKKβ (1 & 2) are therapeutics for diseases which include rheumatoid arthritis, transplant rejection, inflammatory bowel disease, osteoarthritis, asthma, chronic obstructive pulmonary disease, atherosclerosis, psoriasis, multiple sclerosis, stroke, systemic lupus erythematosus, Alzheimer's disease, brain ischemia, traumatic brain injury, Parkinson's disease, amyotrophic lateral sclerosis, subarachnoid hemorrhage or other diseases or disorders associated with excessive production of inflammatory mediators in the brain and central nervous system.

Met is associated with most types of the major human cancers and expression is often correlated with poor prognosis and metastasis. Inhibitors of Met are therapeutics for diseases which include cancers such as lung cancer, NSCLC (non small cell lung cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, brain stem glioma or pituitary adenomas), cancers of the blood such as acute myeloid leukemia, chronic myeloid leukemia, etc, Barrett's esophagus (pre-malignant syndrome) neoplastic cutaneous disease, psoriasis, mycoses fungoides and benign prostatic hypertrophy, diabetes related diseases such as diabetic retinopathy, retinal ischemia and retinal neovascularization, hepatic cirrhosis, cardiovascular disease such as atherosclerosis, immunological disease such as autoimmune disease and renal disease. Preferably, the disease is cancer such as acute myeloid leukemia and colorectal cancer.

The Nima-related kinase 2 (Nek2) is a cell cycle-regulated protein kinase with maximal activity at the onset of mitosis that localizes to the centrosome. Functional studies have implicated Nek2 in regulation of centrosome separation and spindle formation. Nek2 protein is elevated 2- to 5-fold in cell lines derived from a range of human tumors including those of cervical, ovarian, prostate, and particularly breast.

p70S6K-mediated diseases or conditions include, but are not limited to, proliferative disorders, such as cancer and tuberous sclerosis.

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other immunomodulatory or anti-inflammatory substances, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA4Ig. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Scheme I:

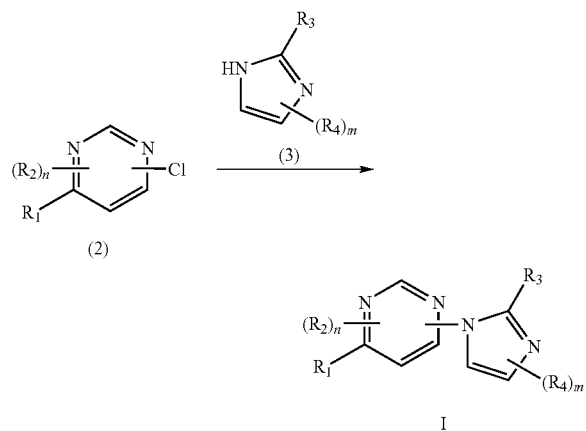

in which $R_1$, $R_2$, $R_3$, $R_4$, n and m are as defined for Formula I in the Summary of the Invention. A compound of Formula I can be prepared by reacting a compound of formula 2 with a compound of formula 3 in the presence of a suitable base (e.g., DIPEA, or the like) and a suitable solvent (e.g., butanol, THF, DMF, or the like). The reaction proceeds in a temperature range of about 80 to about 120° C. and can take up to about 20 hours to complete.

A detailed example of the synthesis of a compound of formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt form, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) those of reaction schemes I and II, for example coupling compounds of formula 8 with $R_6YOH$ according to reaction scheme I; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I according to the invention.

Example 1

N-[4-methyl-3-(1-{6-[4-(2-morpholin-4-yl-ethyl)-phenylamino]-pyrimidin-4-yl}-1H-imidazol-2-ylamino)-phenyl]-3-trifluoromethyl-benzamide

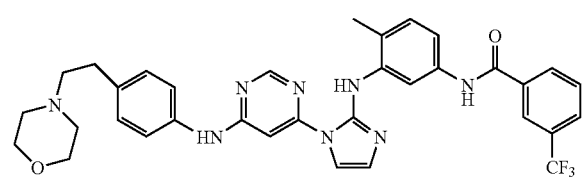

N-(2,2-Diethoxyethyl)carbodiimide

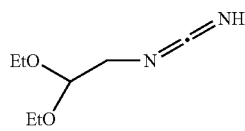

A solution of the aminoacetaldehyde diethyl acetal (13.16 g, 99 mmol) in ether (35 mL) was added to a suspension of CNBr (10.47 g, 99 mmol) in hexane (35 mL) at room temperature. The reaction mixture was stirred at room temperature overnight. The solid was removed by filtration and washed with ether. The combined filtrate was concentrated. Purification by column chromatography (silica gel, eluting with dichloromethane to 4% methanol in dichloromethane, gradient) afforded the title compound (7.0 g, 44.7%, one half of the starting amine served as a sacrificial base in the reaction) ($R_f$: 2.70, 4% methanol in dichloromethane, stain with 10% ethanolic molybdatophosphoric acid). $^1$H NMR 400 MHz (CDCl$_3$) δ 4.58 (t, J=5.2 Hz, 1H), 3.77-3.69 (m, 2H), 3.65 (br, s, 1H), 3.60-352 (m, 2H), 3.16 (t, J=5.6 Hz, 1H), 1.23 (t, 6H, J=6.8 Hz).

N-[3-(1H-Imidazol-2-ylamino)-4-methyl-phenyl]-3-trifluoromethyl-benzamide

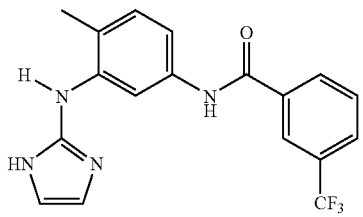

A mixture of N-(2,2-diethoxyethyl)carbodiimide (398 mg, 2.51 mmol), 3-amino-4-methyl-phenyl]-3-trifluoromethyl-benzamide (649 mg, 2.20 mmol), methanesulfonic acid (143 μL, 2.20 mmol) in ethanol (25 mL) is heated at reflux for 16 hours. An additional portion of N-(2,2-diethoxyethyl)carbodiimide (525 mg, 3.32 mmol) and methanesulfonic acid (143 μL, 2.20 mmol) are added. After an additional 3 hours refluxing, the reaction mixture is concentrated. The residue is dissolved in HCl (6N, 5 mL) and ethanol (5 mL). After stirring overnight, the reaction mixture is concentrated and basified with 25% NaOH solution to a pH of 14. The mixture is stirred for 30 minutes, extracted with CH$_2$Cl$_2$, dried, concentrated and purified by column chromatography (silica gel, eluting with 7N NH$_3$ in methanol:dichloromethane from 2% to 4%) to give the title compound.

N-{3-[1-(6-chloro-pyrimidin-4-yl)-1H-imidazol-2-ylamino]-4-methyl-phenyl}-3-trifluoromethyl-benzamide

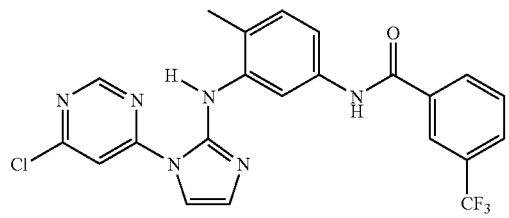

A mixture of N-[3-(1H-Imidazol-2-ylamino)-4-methyl-phenyl]-3-trifluoromethyl-benzamide (330 mg, 0.92 mmol), 4,6-dichloropyrimidine (409 mg, 2.75 mmol), N,N-diisopropylethyl amine (500 μL, 2.87 mmol) in 2-butanol (20 mL) is heated at 110° C. After 16 hours, the reaction mixture is concentrated. The solid is washed with saturated sodium carbonate, water, ethyl acetate, and dried to give the title compound. $^1$H NMR 600 MHz (DMSO-d$_6$) δ 10.71 (s, 1H), 10.50 (s, 1H), 9.09 (s, 1H), 8.80 (s, 1H), 8.33 (s, 1H), 8.29 (d, J=7.8 Hz, 1H), 8.17 (s, 1H), 7.96 (d, J=8.4 Hz, 1H), 7.84 (s, 1H), 7.77 (t, J=8.4 Hz, 1H), 7.42 (d, J=7.2 Hz, 1H), 7.21 (d, J=8.4 Hz, 1H), 6.95 (s, 1H), 2.38 (s, 3H); MS m/z 473.3 (M+1).

N-[4-methyl-3-(1-{6-[4-(2-morpholin-4-yl-ethyl)-phenylamino]-pyrimidin-4-yl}-1H-imidazol-2-ylamino)-phenyl]-3-trifluoromethyl-benzamide

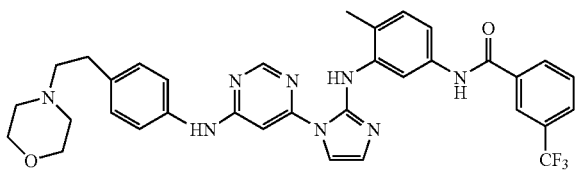

A Smith vial (2-5 mL) is charged with N-{3-[1-(6-chloro-pyrimidin-4-yl)-1H imidazol-2-ylamino]-4-methyl-phenyl}-3-trifluoromethyl-benzamide (16.8 mg, 0.035 mmol), 4-(2-morpholin-4-yl-ethyl)-phenylamine (22 mg, 0.11 mmol), p-toluenesulfonic acid monohydrate (4.4 mg, 0.023 mmol) and DMSO (0.5 mL). After purging with Argon, the vial is sealed and irradiated at 100° C. for 1.5 hours in a Smith Synthesizer. The resulting solution is subjected to purification by reverse-phase LC-MS to yield the title compound. $^1$H NMR 600 MHz (DMSO-d$_6$) δ 11.00 (s, 1H), 10.54 (s, 1H), 10.09 (s, 1H), 8.69 (s, 1H), 8.50 (s, 1H), 8.30 (s, 1H), 8.28 (d, J=8.4 Hz, 1H), 7.97 (d, J=6.6 Hz, 1H), 7.79 (t, J=8.4 Hz 1H), 7.64 (d, J=8.4 Hz, 2H), 7.55 (s, 1H), 7.50 (d, J=8.4 Hz, 1H), 7.28 (m, 3H), 7.06 (s, 1H), 6.95 (s, 1H), 4.03 (d, J=12.6 Hz, 2H), 4.03 (d, J=12.6 Hz, 2H), 3.69 (t, J=12.6 Hz, 2H), 3.52 (d, J=12.0 Hz, 2H), 3.36 (t, J=7.8 Hz, 2H), 3.13 (br, 2H), 2.98 (t, J=7.8 Hz, 2H), 2.33 (s, 3H); MS m/z 643.4 (M+1).

Example 2

N-{3-[1-(6-Cyclopropylamino-pyrimidin-4-yl)-1H-imidazol-2-ylamino]-4-methyl-phenyl}-3-(4-methyl-imidazol-1-yl)-5-trifluoromethyl-benzamide

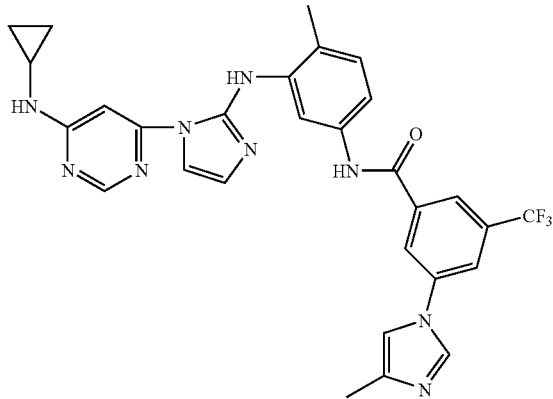

N-(3-Amino-4-methyl-phenyl)-benzamide

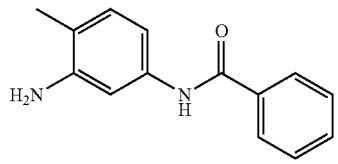

To a solution of 4-methyl-3-nitro-aniline (15.86 g, 104 mmol), pyridine (17.0 mL, 208 mmol) in CH$_2$Cl$_2$ (150 mL) at 0° C. was added benzoyl chloride (13.30 mL, 114 mmol) dropwise. After stirring for 2 h at room temperature, the reaction mixture was concentrated. The residue was washed with saturated sodium carbonate solution, water then ethyl ether to afford the desired nitro compound, which was used in the next step without any further purification. $^1$H NMR 600 MHz (Acetone-d$_6$) δ 9.85 (s, 1H), 8.61 (s, 1H), 8.05-8.02 (m, 3H), 7.60 (t, 1H, J=7.2 Hz), 7.53 (t, 2H, J=7.2 Hz), 7.46 (d, 1H, J=7.8 Hz), 2.54 (s, 3H); MS m/z 257.3 (M+1).

The nitro compound was dissolved in ethanol (250 mL). After hydrogenation on palladium (10 wt % on activated carbon, wet, Degussa type, 5 g) using Parr Shaker, 20-30 psi H$_2$, 16 h, the reaction mixture was filtered through a pad of celite and washed with ethanol. The combined filtrate and washings were concentrated to afford the title compound N-(3-Amino-4-methyl-phenyl)-benzamide (22.43 g, 95% over two steps), which was used for next reaction without any further purification.

$^1$H NMR 600 MHz (Acetone-d$_6$) δ 9.40 (s, 0.4H), 9.23 (s, 0.6H), 7.96 (t, 2H, J=7.8 Hz), 7.55-7.52 (m, 1H), 7.49 (d, 1H, J=7.2 Hz), 7.47 (d, 1H, J=7.2 Hz), 7.37 (d, 0.4; H, J=8.4 Hz), 7.31 (s, 0.6H), 7.17 (s, 0.4H), 7.11 (d, 0.4H, J=8.4 Hz), 7.95 (d, 0.6H, J=8.4 Hz), 7.91 (d, 0.6H, J=8.4 Hz), 4.44 (br, s, 1.2H), 2.90 (br, s, 0.8H), 2.11 (s, 1.8H), 1.98 (s, 1.2H); MS m/z 227.3 (M+1).

N-[3-(1H-Imidazol-2-ylamino)-4-methyl-phenyl]-benzamide

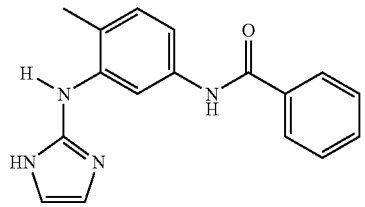

A mixture of N-(2,2-diethoxyethyl)carbodiimide (10.38 g, 65.6 mmol), 3-amino-4-methyl-phenyl]-benzamide (7.42 g, 32.8 mmol), methanesulfonic acid (3.20 mL, 49.3 mmol) in ethanol (200 mL) was heated at reflux for 19 h. The reaction mixture was concentrated (No purification was pursued in this step). The residue was dissolved in HCl solution (6N, 30 mL). After stirring for overnight, the reaction mixture was neutralized with 25% NaOH solution at 0° C. to pH=6, then basified with saturated sodium carbonate solution to pH=11. The mixture was stirred for 30 minutes, and extracted with ethanol in CH$_2$Cl$_2$ (100 mL), then 10% ethanol in CH$_2$Cl$_2$ (2×100 mL). The combined organic layers were dried over Na$_2$SO$_4$, filtered, concentrated and dried under vacuum. The residue was triturated in CH$_2$Cl$_2$ (50 mL). The solid was collected by filtration and washed with CH$_2$Cl$_2$, dried to afford the title compound N-[3-(1H-imidazol-2-ylamino)-4-methyl-phenyl]-benzamide as a white solid (4.80 g, 50%). $^1$H NMR 600 MHz (DMSO-d$_6$) δ 10.79 (s, 1H), 10.11 (s, 1H), 8.00 (d, 1H, J=2.4 Hz), 7.94 (d, 2H, J=7.2 Hz), 7.60 (s, 1H), 7.56 (t, 1H, J=7.2 Hz), 7.49 (t, 2H, J=7.2 Hz), 7.25 (dd, 1H, J=2.4, 8.4 Hz), 7.04 (d, 1H, J=7.8 Hz), 6.80 (br, s, 1H), 6.65 (br, s, 1H), 2.20 (s, 3H), MS m/z 293.4 (M+1).

N-{3-[1-(6-chloro-pyrimidin-4-yl)-1H-imidazol-2-ylamino]-4-methyl-phenyl}-benzamide

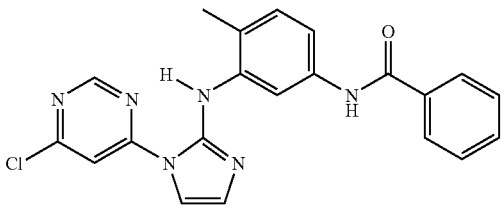

A mixture of N-[3-(1H-imidazol-2-ylamino)-4-methyl-phenyl]-3-benzamide (3.41 g, 11.7 mmol), 4,6-dichloropyrimidine (5.20 g, 34.9 mmol), N,N-diisopropylethyl amine (6.10 mL, 35.0 mmol) in 2-butanol (150 mL) was heated at 100° C. After 16 h, the reaction mixture was concentrated. The residue was washed with saturated sodium carbonate, water, ethyl acetate, dried to afford the title compound (2.65 g, 56%), the ethyl acetate filtrate was condensed, flash chromatography (silica gel, eluting with methanol in dichloromethane from 1% to 5%, gradient) to afford an additional portion of the title compound (500 mg, 10%). $^1$H NMR 600

MHz (DMSO-d$_6$) δ 10.66 (s, 1H), 10.26 (s, 1H), 9.08 (s, 1H), 8.80 (s, 1H), 8.16 (s, 1H), 7.98 (d, 2H, J=7.2 Hz), 7.82 (m, 1H), 7.58 (t, 1H), J=7.8 Hz), 7.52 (t, 2H, J=7.8 Hz), 7.39 (d, 1H, J=8.4 Hz), 7.18 (d, 1H, J=8.4 Hz), 6.93 (m, 1H), 2.36 (s, 3H); MS m/z 405.1 (M+1).

N-{3-[1-(6-Cyclopropylamino-pyrimidin-4-yl)-1H-imidazol-2-ylamino]-4-methyl-phenyl}-benzamide

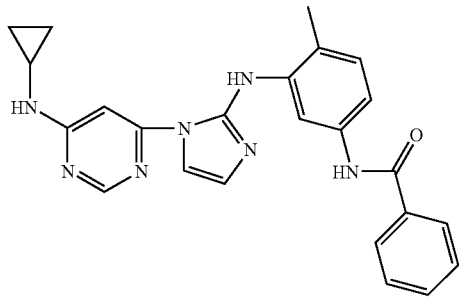

A mixture of N-{3-[1-(6-chloro-pyrimidin-4-yl)-1H-imidazol-2-ylamino]-4-methyl-phenyl}-benzamide (2.65 g, 6.55 mmol), cyclopropylamine (8.8 mL, 124.43 mmol) in 2-propanol (30 mL) was heated at 65° C. for 16 h. The reaction mixture was then cooled down to room temperature and concentrated. The residue yellow solid was washed with water, dried under vacuum to afford the title compound. The obtained crude title compound was directly used for the next step reaction without any further purification. $^1$H NMR 600 MHz (DMSO-d$_6$) δ 11.13 (bs, 1H), 10.24 (s, 1H), 8.77 (s, 1H), 8.48 (bs, 1H), 8.10 (bs, 1H), 7.98 (d, 2H, J=6.0 Hz), 7.71 (bs, 1H), 7.57 (s, 1H), 7.52 (s, 2H), 7.34 (d, 1H, J=6.6 Hz), 7.15 (d, 1H, J=6.6 Hz), 6.88 (s, 1H), 6.74 (bs, 1H), 2.61 (bs, 1H), 2.33 (s, 3H), 0.82 (s, 2H), 0.53 (s, 2H); MS m/z 426.5 (M+1).

N-3-[1-(6-Cyclopropylamino-pyrimidin-4-yl)-1H-imidazol-2-yl]-4-methyl-benzene-1,3-diamine

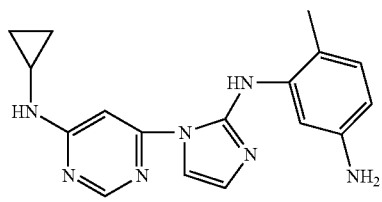

The crude product of N-{3-[1-(6-cyclopropylamino-pyrimidin-4-yl)-1H-imidazol-2-ylamino]-4-methyl-phenyl}-benzamide was dissolved in aqueous HCl solution (6 N, 50 mL) and heated at 105° C. for 6 hours. The reaction mixture was then cooled down to room temperature. The white precipitate was filtered off and washed with water. The combined filtrate solution was concentrated to viscous oil. Addition of saturated sodium carbonate aqueous solution to the oil crushed out the title compound[1] as a yellow solid, which was collected by filtration, washed with water and air dried (1.6 g, 74% over two steps). $^1$H NMR 600 MHz (DMSO-d$_6$) δ 10.91 (bs, 1H), 8.44 (bs, 1H), 8.06 (bs, 1H), 7.84 (bs, 1H), 7.64 (bs, 1H), 6.84 (s, 1H), 6.80 (d, 1H, J=7.8 Hz), 6.70 (bs, 1 H), 6.08 (d, 1H, J=8.4 Hz), 4.82 (bs, 2H), 2.61 (bs, 1H), 2.18 (s, 3H), 0.81 (s, 2H) 0.52 (s, 2H); MS m/z 322.4 (M+1).

N-{3-[1-(6-Cyclopropylamino-pyrimidin-4-yl)-1H-imidazol-2-ylamino]-4-methyl-phenyl}-3-(4-methyl-imidazol-1-yl)-5-trifluoromethyl-benzamide

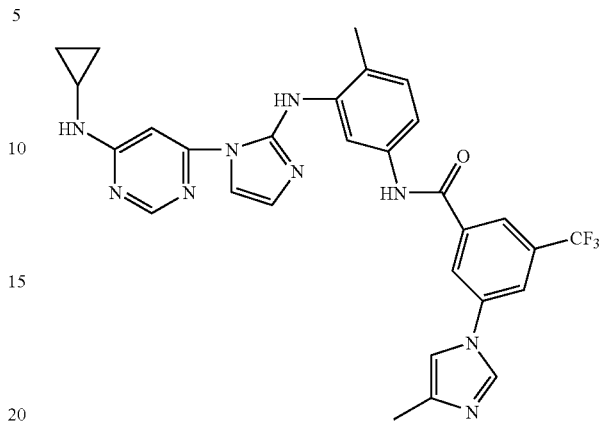

To a solution of N-3-[1-(6-cyclopropylamino-pyrimidin-4-yl)-1H-imidazol-2-yl]-4-methyl-benzene-1,3-diamine (1.38 g, 4.28 mmol), 3-(4-methyl-imidazol-1-yl)-5-trifluoromethyl-benzoic acid (1.18 g, 4.37 mmol) and DIPEA (3 mL, 17.2 mmol) in DMF (20 mL), was added HATU (1.68 g, 4.42 mmol) as solid. The reaction mixture was stirred at room temperature for 1 hour. The solvent was evaporated and the residue oil was treated with saturated sodium bicarbonate aqueous solution. The precipitated off white solid was collected by filtration and washed with water. The solid was then slurried in methanol at 50° C. for 30 min. The solid was collected by filtration, washed with MeOH, dried under vacuum to afford the title compound (2.14 g, 87%). $^1$H NMR 400 MHz (DMSO-d$_6$) δ 10.21 (bs, 1H), 10.52 (s, 1H), 8.78 (s, 1H), 8.54-8.44 (m, 2H), 8.42 (s, 1H), 8.23 (s, 1H), 8.19 (s, 1H), 8.11 (bs, 1H), 7.72 (s, 2H), 7.40 (dd, 1H, J=8.0 Hz, 1.2 Hz), 7.20 (d, 1H, J=8.4 Hz), 6.89 (d, 1H, J=1.2 Hz), 6.74 (bs, 1H), 2.66 (bs, 1H), 2.35 (s, 3H), 2.19 (s, 3H), 0.82 (bs, 2H), 0.53 (bs, 2H); MS m/z 574.2 (M+1).

Example 3

Synthesis of 3-[1-(6-Cyclopropylamino-pyrimidin-4-yl)-1H-imidazol-2-ylamino]-N-[4-(4-ethyl-piperazin-1-ylmethyl)-3-trifluoromethyl-phenyl]-4-methyl-benzamide

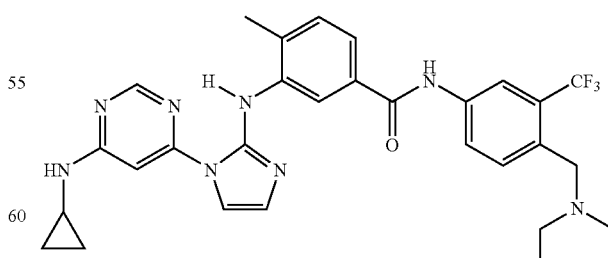

4-Chloro-6-(2-chloro-imidazol-1-yl)-pyrimidine

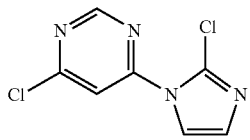

2-Chloro-1H-imidazole (2.0 g, 20 mmol), 4,6-dichloropyrimidine (6 g, 40 mmol) and DIEA (10.4 ml, 60 mmol) were mixed in 40 mL butanol and refluxed at 120° C. for 24 hours. The solvent was removed by rotary evaporation. The crude product was purified by flash chromatography on silica gel (0% EtOAc/hexanes to 20% EtOAc/hexanes gradient), afforded the title compound (2.6 g, 62% yield) as yellow solid. $R_f$=0.25 (20% EtOAc/hexanes); $^1$H NMR 400 MHz (DMSO-$d_6$) δ 9.13 (s, 1H), 8.17 (s, 1H), 7.94 (d, 1H), 7.17 (d, 1 H); MS m/z 215.4 (M+1).

[6-(2-Chloro-imidazol-1-yl)-pyrimidin-4-yl]-cyclopropyl-amine

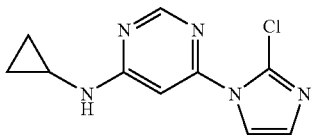

4-Chloro-6-(2-chloro-imidazol-1-yl)-pyrimidine (0.85 g, 4 mmol) and cyclopropylamine (1.4 mL, 20 mmol) were mixed in 10 mL methanol and stirred at 50° C. for 12 hours. After reaction was complete, the solvent was removed by rotary evaporation. The crude product was washed with water and taken to dryness to give the title compound (0.84 g, 90%); $^1$H NMR 400 MHz (DMSO-$d_6$) δ 8.45 (s, 1H), 8.17 (d, 1H), 7.75 (s, 1 H), 7.08 (s, 1H), 6.80 (d, 1H), 3.34 (s, 1H), 0.78 (br, 2H), 0.52 (br, 2H); MS m/z 236.4 (M+1).

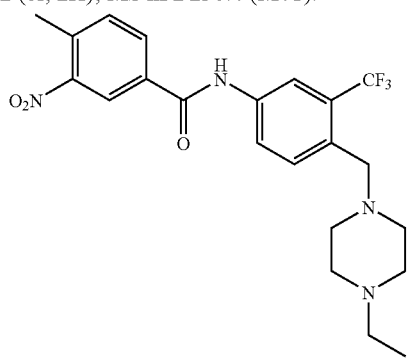

Into a solution of 4-(4-Ethyl-piperazin-1-ylmethyl)-3-trifluoromethyl-phenylamine (3.0 g, 1.04 mmol, 1.0 eq.) in dichloromethane (5.2 ml) was added diisopropylethyl amine (2.00 ml, 1.14 mmol, 1.1 eq.). The solution was cooled to 0° C., after which 4-Methyl-3-nitrobenzoylchloride (2.13 g, 1.07 mmol, 1.03 eq.) was added in portions into the reaction mixture which was further equilibrated for 30 minutes. The reaction mixture was then partitioned between dichloromethane and saturated sodium carbonate solution. The organic layer was separated and the aqueous layer was extracted with dichloromethane. The combined organic extracts were washed with water, brine, dried over Na$_2$SO$_4$, filtered and concentrated to afford the desired product (4.58 g, 98%). The desired compound was used in the next step without further purification.

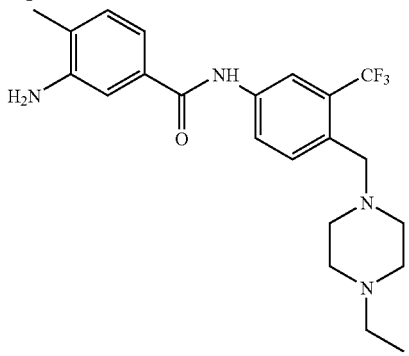

Into a solution N-[4-(4-Ethyl-piperazin-1-ylmethyl)-3-trifluoromethyl-phenyl]-4-methyl-3-nitro-benzamide (4.5 g, 1.00 mmol, 1.0 eq.) in MeOH (50 ml) was added Raney Nickel (0.45 g, 10 wt %). The suspension was stirred under hydrogen atmosphere (1 atm) for 24 hours. At the end of reaction as indicated by HPLC, the reaction mass was filtered over celite and the filtrate was concentrated under reduced pressure to yield the desired product (4.1 g, 97%) $^1$H NMR 400 MHz (DMSO-$d_6$) δ 10.24 (s, 1H), 8.18 (s, 1H), 8.02 (d, J=8.0 Hz, 1H), 7.66 (d, J=8.8 Hz, 1H, 7.16 (s, 1H), 7.13 (m, 2H), 5.1 (s, 2H), 3.55 (s, 2H), 2.37 (m, 10H) 2.11 (s, 3H), 1.05 (t, 3H).

3-[1-(6-Cyclopropylamino-pyrimidin-4-yl)-1H-imidazol-2-ylamino]-N-[4-(4-ethyl-piperazin-1-ylmethyl)-3-trifluoromethyl-phenyl]-4-methyl-benzamide

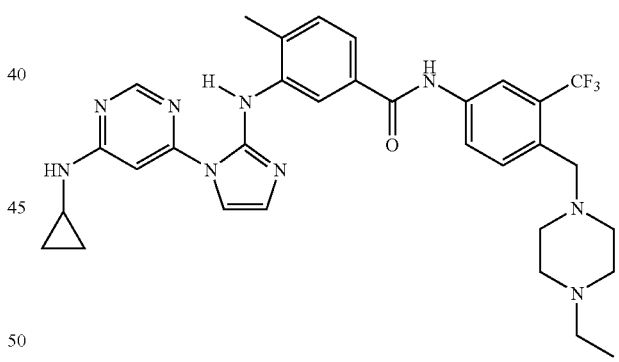

A mixture of [6-(2-chloro-imidazol-1-yl)-pyrimidin-4-yl]-cyclopropyl-amine (2.24 g, 9.53 mmol), xxxx (2.00 g, 4.76 mmol) and MeSO$_3$H (930 uL, 14.3 mol) in 1,3-dimethyl-imidazolidin-2-one (4 mL) was heated at 90° C. in a sealed tube. After overnight, the reaction mixture was cooled to room temperature and diluted with CHCl$_3$ and washed with saturated aqueous NaHCO$_3$ solution. The organic layer was dried over Na$_2$SO$_4$ and concentrated. The residue was dissolved in CHCl$_3$ and purified by column chromatography (EtOAc/Hex/MeOH=9/3/1) to give the product as a white powder which was recrystallized from CHCl$_3$/MeOH to afford the title compound (1.15 g, 39% yield). $^1$H NMR 400 MHz (DMSO-$d_6$) δ 11.29 (bs, 1H), 10.42 (s, 1H), 9.10 (s, 1H), 8.50 (bs, 1H), 8.23 (bs, 1H), 8.08 (bs, 1H), 8.04 (d, 1H, J=9.6 Hz), 7.69 (d, 1H, J=8.0 Hz), 7.71-7.69 (bs, 1H), 7.46 (d, 1H, J=7.6 Hz), 7.36 (d, 1H, J=7.2 Hz), 6.91 (s, 1H), 6.75 (bs, 1H), 3.56 (s, 2H), 2.65 (br, 1H), 2.43 (s, 1H), 2.43-2.33 (m, 10H), 0.98 (t, 3H, J=6.8 Hz), 0.82 (bs, 2H), 0.53 (bs, 2H); MS m/z 620.3 (M+1).

By repeating the procedures described in the above examples, using appropriate starting materials, the following compounds of Formula I, as identified in Table 1, are obtained.

TABLE 1

| Compound Number | Structure | Physical Data $^1$H NMR 400 MHz (DMSO-$d_6$) and/or MS (m/z) |
|---|---|---|
| 3 | 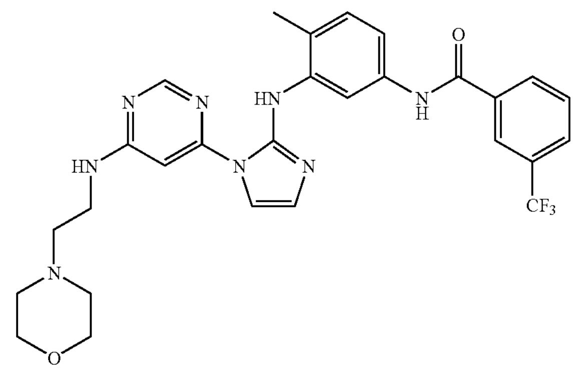 | $^1$H NMR 600 MHz (DMSO-$d_6$)δ10.09(bs, 1H), 10.54(s, 1H), 9.94(bs, 1H), 8.58(bs, 1H), 8.47(bs, 1H), 8.41(s, 1H), 8.28 (d, J = 8.2 Hz, 1H), 8.05(bs, 0.5H), 7.97(d, J = 8.2 Hz, 1H), 7.79(d, J = 8.2 Hz, 1H), 7.58(bs, 0.5H), 7.49(d, J = 7.2 Hz, 1H), 7.28(d, J = 8.2 Hz, 1H), 7.06(s, 1H), 6.77(s, 1H), 4.08-3.92(m, 2H), 3.84-3.64 (m, 4H), 3.60-3.48(m, 2H), 3.40-3.28(m, 2H), 3.24-3.08(m, 2H), 2.31(s, 3H); MS m/z 567.4 (M + 1). |
| 4 | 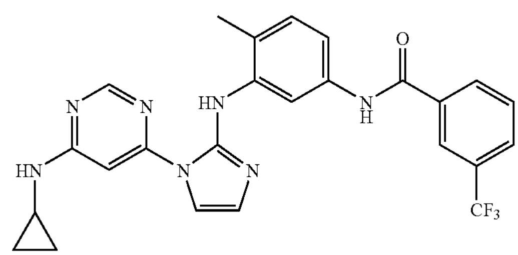 | $^1$H NMR 600 MHz (DMSO-$d_6$)δ11.33(bs, 1H), 10.56(s, 1H), 8.48(bs, 1H), 8.30(s, 1H), 8.27(d, J = 7.2 Hz, 2H), 7.98(d, J = 7.2 Hz, 2H), 7.80(t, J = 8.2 Hz, 1H), 7.58(d, J = 7.2 Hz, 1H), 7.33(d, J = 7.2 Hz, 1H), 7.15(bs, 1H), 6.88(bs, 1H), 2.30(s, 3H), 0.84(bs, 2H), 0.55 (bs, 2H); MS m/z 494.4 (M + 1). |
| 5 | 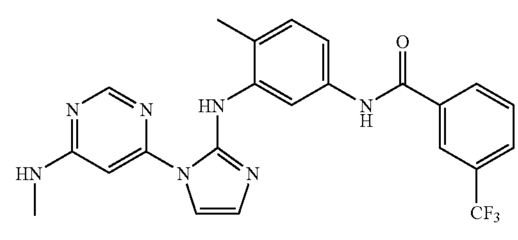 | $^1$H NMR 600 MHz (DMSO-$d_6$)δ 11.42(bs, 0.5H), 11.14(bs, 0.5H), 10.56(s, 1H), 8.54(bs, 0.5H), 8.43(bs, 0.5H), 8.30(s, 1H), 8.27(d, J = 8.2 Hz, 1H), 7.98(d, J = 8.2 Hz, 1H), 7.96-7.84(m, 1H), 7.79(t, J = 7.2 Hz, 1H), 7.72-7.60(m, 1H), 7.58(d, J = 7.2 Hz, 1H), 7.33(d, J = 8.2 Hz, 1H), 7.13(s, 1H), 6.69(s, 1H), 2.89(d, J = 16.4 Hz, 3H), 2.29(s, 3H); MS 468.4 m/z (M + 1). |
| 6 | 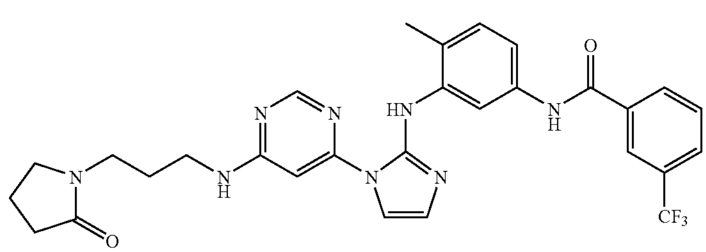 | $^1$H NMR 600 MHz (DMSO-$d_6$)δ 11.40(bs, 0.5H), 11.12(bs, 0.5H), 10.56(s, 1H), 8.52(bs, 0.5H), 8.43(bs, 0.5H), 8.30(s, 1H), 8.27(d, J = 8.2 Hz, 1H), 8.21(bs, 1H), 7.98(d, J = 8.2 Hz, 1H), 7.90(bs, 1H), 7.80(t, J = 8.2 Hz, 1H), 7.64(bs, 1H), 7.59(d, J = 7.2 Hz, 1H), 7.33(d, J = 8.2 Hz, 1H), 7.20-7.08(m, 1H), 6.80-6.68(m, 1H), 3.44-3.32(m, 4H), 3.30-3.22(m, 2H), 2.29(s, 3H), 2.22(t, J = 7.2 Hz, 2H), 1.98-1.88(m, 2H), 1.78-1.70(m, 2H); MS m/z 579.4 (M + 1). |

TABLE 1-continued

| Compound Number | Structure | Physical Data $^1$H NMR 400 MHz (DMSO-$d_6$) and/or MS (m/z) |
|---|---|---|
| 7 | 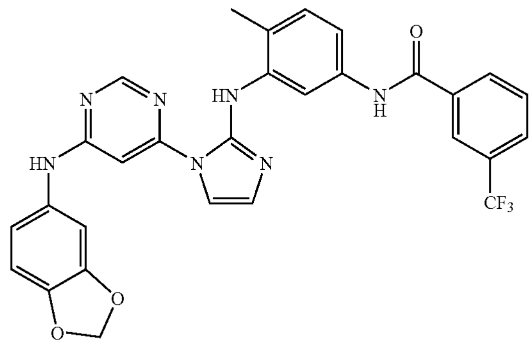 | $^1$H NMR 600 MHz (DMSO-$d_6$) δ 11.03(s, 1H), 10.56(s, 1H), 9.93(s, 1H), 8.64(s, 1H), 8.30(s, 1H), 8.27(d, J = 8.2 Hz, 1H), 7.98(d, J = 8.2 Hz, 1H), 7.79(t, J = 8.2 Hz, 1H), 7.66(s, 1H), 7.58(d, J = 8.2 Hz, 1H), 7.33(d, J = 8.2 Hz, 1H), 7.29(s, 1H), 7.13(s, 1H), 6.97(d, J = 8.2 Hz, 1H), 6.93(d, J = 8.2 Hz, 1H), 6.86(s, 1H), 6.03(s, 2H), 2.30 (s, 3H); MS m/z 574.4 (M + 1). |
| 8 | 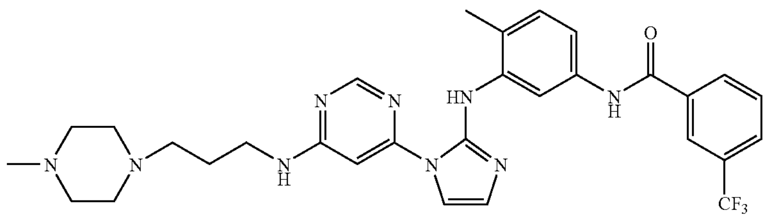 | MS m/z 594.5 (M + 1). |
| 9 | 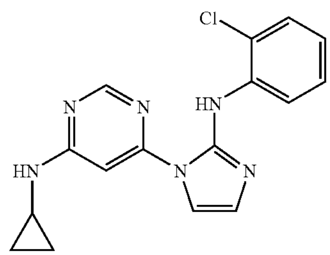 | $^1$H NMR 400 MHz (DMSO-$d_6$) δ 11.81(bs, 1H), 8.60-8.44(m, 1H), 8.19(bs, 1H), 7.84(bs, 1H), 7.52(d, J = 8.2 Hz, 1H), 7.36(t, J = 8.2 Hz, 1H), 7.06-6.96(m, 2H), 6.80(bs, 1H), 0.83(bs, 2H), 0.53(bs, 2H); MS m/z 327.10 (M + 1). |
| 10 | 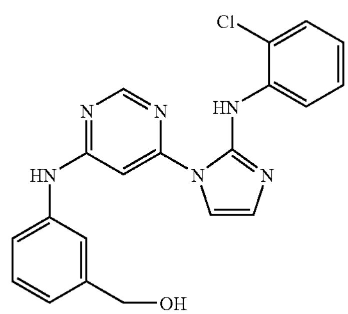 | MS m/z 393.12 (M + 1). |
| 11 | 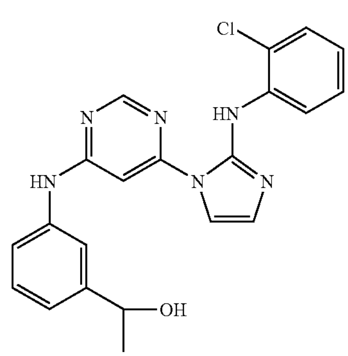 | $^1$H NMR 400 MHz (DMSO-$d_6$) δ 11.58(s, 1H), 9.99(s, 1H), 8.71(s, 1H), 8.53(bs, 1H), 7.60-7.48(m, 4H), 7.40-7.28 (m, 2H), 7.10-7.04(m, 2H), 7.04-7.00(m, 1H), 6.87(s, 1H), 4.72(q, J = 6.8 Hz, 1H), 1.34(d, J = 6.2 Hz, 3H); MS m/z 407.13 (M + 1). |

TABLE 1-continued

| Compound Number | Structure | Physical Data ¹H NMR 400 MHz (DMSO-d₆) and/or MS (m/z) |
|---|---|---|
| 12 | 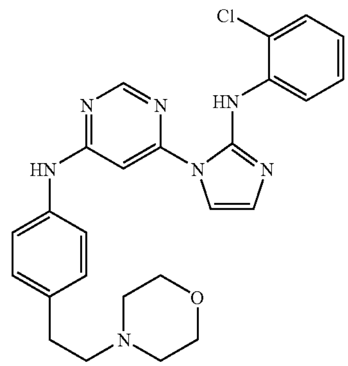 | MS m/z 475.19 (M + 1). |
| 13 | 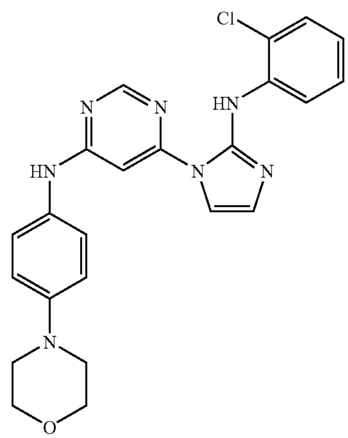 | MS m/z 447.26 (M + 1). |
| 14 | 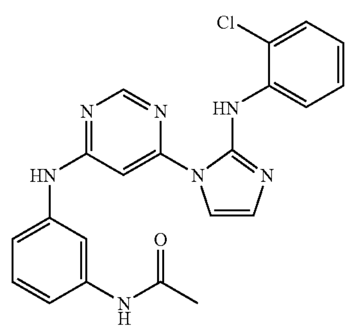 | ¹H NMR 400 MHz (DMSO-d₆)δ11.57(s, 1H), 10.02(s, 2H), 8.70(s, 1H), 7.93(s, 1H), 7.55-7.50(m, 2H), 7.42-7.32 (m, 2H), 7.28(t, J = 8.2 Hz, 1H), 7.24-7.18(m, 1H), 7.06-7.00(m, 2H), 6.92(s, 1H), 2.06(s, 3H); MS m/z 420.13 (M + 1). |
| 15 | 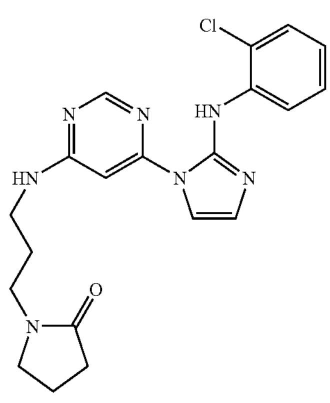 | MS m/z 412.16 (M + 1). |

TABLE 1-continued

| Compound Number | Structure | Physical Data ¹H NMR 400 MHz (DMSO-$d_6$) and/or MS (m/z) |
|---|---|---|
| 16 | 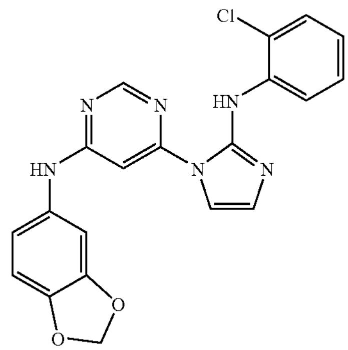 | MS m/z 407.05 (M + 1). |
| 17 | 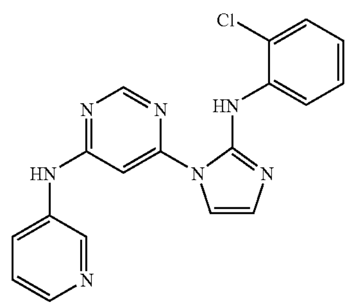 | MS m/z 364.10 (M + 1). |
| 18 | 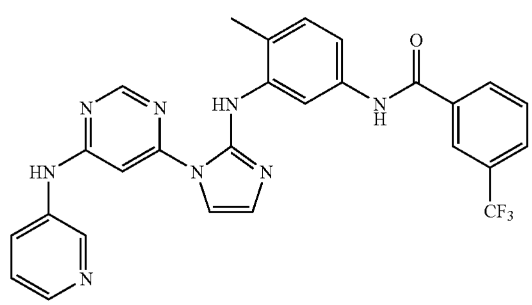 | MS m/z 531.10 (M + 1). |
| 19 | 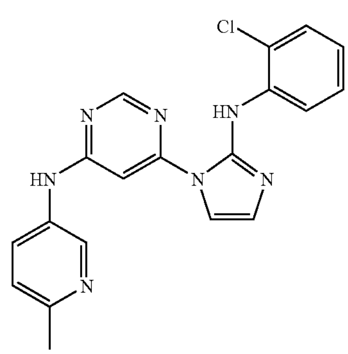 | MS m/z 378.10 (M + 1). |

TABLE 1-continued

| Compound Number | Structure | Physical Data $^1$H NMR 400 MHz (DMSO-$d_6$) and/or MS (m/z) |
|---|---|---|
| 20 | 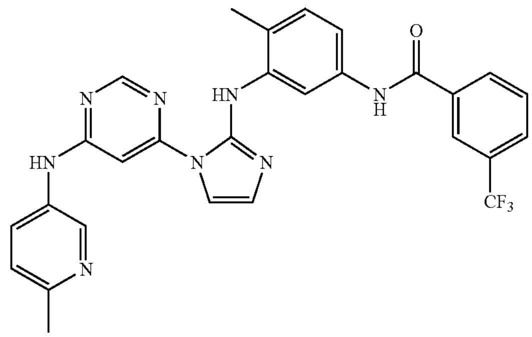 | $^1$H NMR 400 MHz (DMSO-$d_6$)δ10.99(s, 1H), 10.57(s, 1H), 10.51(s, 1H), 9.02(d, J = 2.0 Hz, 1H), 8.79(s, 1H), 8.41 (d, J = 4.8 Hz, 1H), 8.37(s, 1H), 8.33-8.25(m, 3H), 7.98(d, J = 8.2 Hz, 1H), 7.79(t, J = 8.2 Hz, 1H), 7.67(d, J = 2.7 Hz, 1H), 7.63(dd, J = 8.2, 4.8 Hz, 1H), 7.54(dd, J = 8.2, 1.4 Hz, 1H), 7.32(d, J = 8.2 Hz, 1H), 7.13 (d, J = 2.0 Hz, 1H), 7.07(s, 1H), 2.32(s, 3H); MS m/z 545.20 (M + 1). |
| 21 | 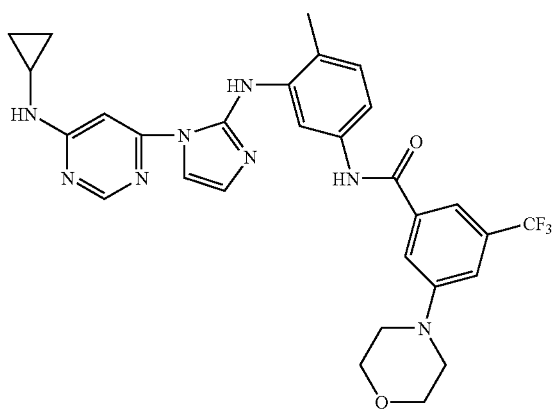 | MS m/z 578.20 (M + 1). |
| 22 | 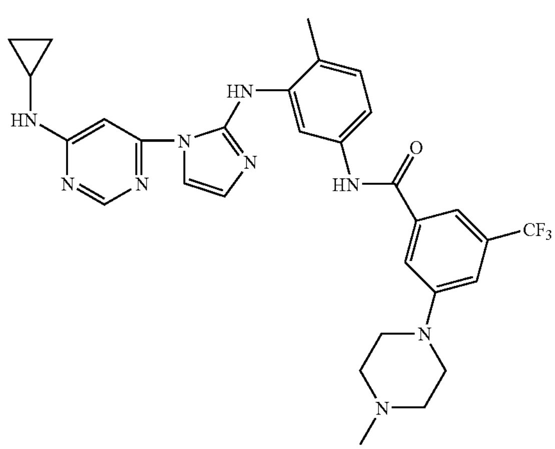 | $^1$H NMR 600 MHz (DMSO-$d_6$)δ11.28(bs, 1H), 10.44(s, 1H), 9.91(bs, 1H), 8.48(bs, 1H), 8.40(bs, 1H), 8.22(bs, 1H), 7.89(bs, 1H), 7.79(s, 1H), 7.75(s, 1H), 751(s, 1H), 7.48 (d, J = 7.2 Hz, 1H), 7.28(d, J = 8.2 Hz, 1H), 7.06(s, 1H), 6.84(bs, 1H), 4.16-4.04(m, 2H), 3.60-3.44(m, 2H), ), 3.24-3.04 (m, 4H), 2.89(s, 3H), 2.31(s, 3H), 0.84(s, 2H), 0.54(s, 2H); MS m/z 591.30 (M + 1). |

TABLE 1-continued

| Compound Number | Structure | Physical Data ¹H NMR 400 MHz (DMSO-d₆) and/or MS (m/z) |
|---|---|---|
| 23 | 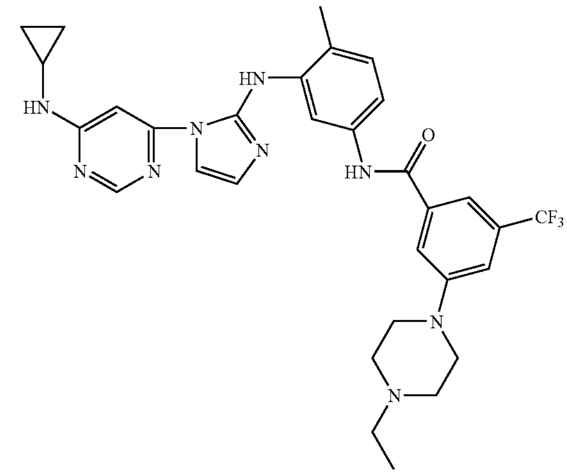 | ¹H NMR 600 MHz (DMSO-d₆)δ11.29(bs, 1H), 10.45(s, 1H), 9.73(bs, 1H), 8.48(bs, 1H), 8.38(bs, 1H), 8.23(bs, 1H), 7.89(bs, 1H), 7.78(s, 1H), 7.75(s, 1H), 7.52(s, 1H), 7.49(d, J = 7.2 Hz, 1H), 7.29(d, J = 8.2 Hz, 1H), 7.07(s, 1H), 6.84(bs, 1H), 4.18-4.06(m, 2H), 3.68-3.56(m, 2H), 3.28-3.18(m, 2H), 3.18-3.08(m, 4H), 2.31(s, 3H), 1.27(t, J = 8.2 Hz, 3H), 0.84(s, 2H), 0.54(s, 2H); MS m/z 605.30 (M + 1). |
| 24 | 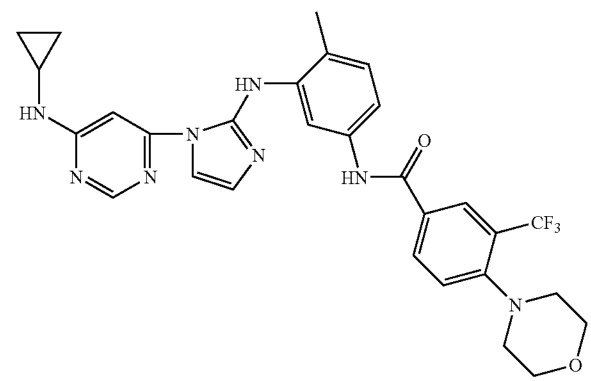 | ¹H NMR 600 MHz (DMSO-d₆)δ11.32(bs, 1H), 10.47(s, 1H), 8.47(bs, 1H), 8.36-8.12(m, 4H), 7.98(bs, 1H), 7.65(d, J = 8.2 Hz, 1H), 7.58(d, J = 8.2 Hz, 1H), 7.32(d, J = 8.2 Hz, 1H), 7.16(bs, 1H), 6.89(bs, 1H), 3.76-3.70(m, 4H), 2.98-2.94(m, 4H), 2.28(s, 3H), 0.84(s, 2H), 0.55(s, 2H); MS m/z 578.30 (M + 1). |
| 25 | 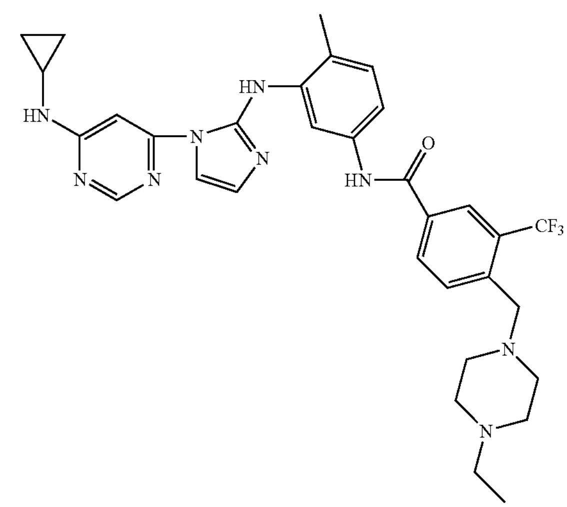 | ¹H NMR 600 MHz (DMSO-d₆)δ11.30(bs, 1H), 10.55(s, 1H), 9.46(bs, 1H), 8.48(bs, 1H), 8.40-8.16(m, 4H), 7.93(d, J = 8.2 Hz, 1H), 7.53(d, J = 8.2 Hz, 1H), 7.30(d, J = 8.2 Hz, 1H), 7.09(bs, 1H), 6.85(bs, 1H), 3.80(s, 2H), 3.52-3.40(m, 2H), 3.20-3.12(m, 2H), 3.08-2.96(m, 2H), 2.96-2.88(m, 2H), 2.48-2.40(m, 2H), 2.30(s, 3H), 1.22(t, J = 7.2 Hz, 3H), 0.84(s, 2H), 0.54(s, 2H); MS m/z 619.30 (M + 1). |

TABLE 1-continued

| Compound Number | Structure | Physical Data ¹H NMR 400 MHz (DMSO-d₆) and/or MS (m/z) |
|---|---|---|
| 26 | 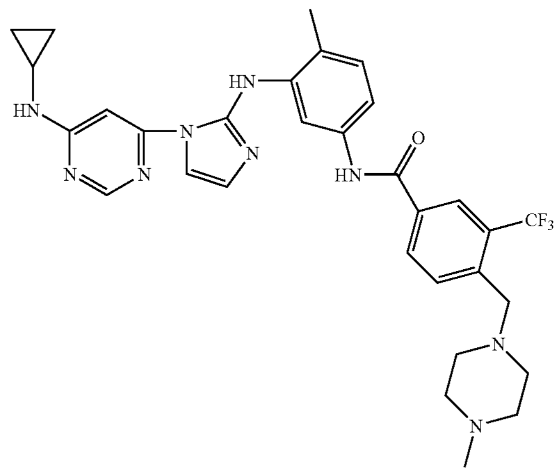 | ¹H NMR 600 MHz (DMSO-d₆) δ 11.31(bs, 1H), 10.55(s, 1H), 9.67(bs, 1H), 8.48(bs, 1H), 8.40-8.20(m, 4H), 7.93(d, J = 8.2 Hz, 1H), 7.54(d, J = 7.2 Hz, 1H), 7.31(d, J = 8.2 Hz, 1H), 7.11(s, 1H), 6.86(bs, 1H), 3.79(s, 2H), 3.46-3.38(m, 2H), 3.12-3.02(m, 2H), 2.96-2.88 (m, 2H), 2.82(s, 3H), 2.46-2.36 (m, 2H), 2.30(s, 3H), 0.84(s, 2H), 0.54(s, 2H); MS m/z 605.30 (M + 1). |
| 27 | 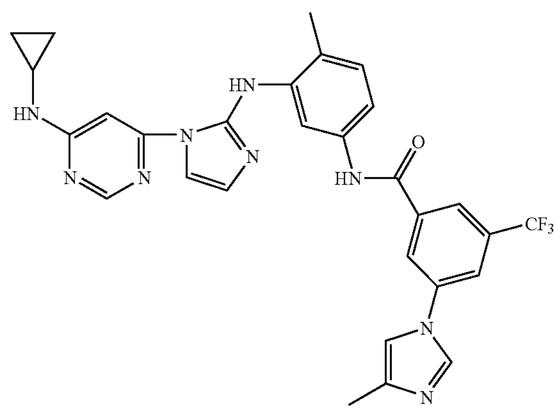 | ¹H NMR 400 MHz (DMSO-d₆) (Free base) δ 11.21(bs, 1H), 10.53(s, 1H), 8.78(s, 1H), 8.56-8.44(m, 3H), 8.24(s, 1H), 8.21(s, 1H), 8.11(bs, 1H), 7.76 (s, 1H), 7.73(bs, 1H), 7.41(dd, J = 8.2, 2.0 Hz, 1H), 7.20(d, J = 8.2 Hz, 1H), 6.89(s, 1H), 6.74(bs, 1H), 2.35(s, 3H), 2.21 (s, 3H), 0.82(s, 2H), 0.53(s, 2H); MS m/z 574.30 (M + 1). |
| 29 | 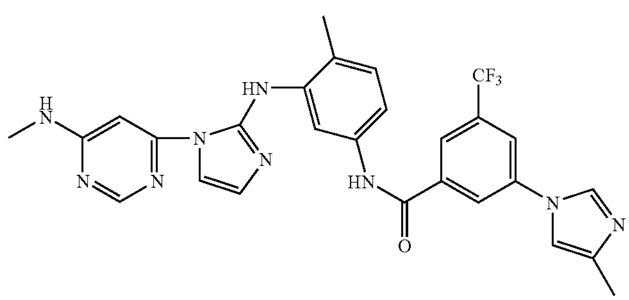 | MS m/z 547.20 (M + 1). |
| 30 | 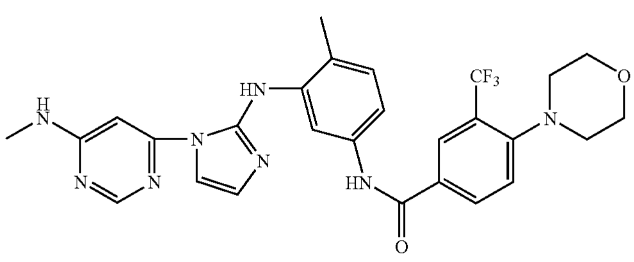 | ¹H NMR 600 MHz (DMSO-d₆) δ 11.42(bs, 0.5H), 11.13(bs, 0.5H), 10.47(s, 1H), 8.54(s, 0.5H), 8.43(s, 0.5H), 8.25(s, 1H), 8.24(s, 1H), 8.22-8.12(m, 1H), 8.02(bs, 1H), 7.88(bs, 1H), 7.65(d, J = 8.2 Hz, 1H), 7.58(d, J = 8.2 Hz, 1H), 7.32(d, J = 8.2 Hz, 1H), 7.15(bs, 1H), 6.71(s, 1H), 3.74(t, J = 5.1 Hz, 4H), 2.96(t, J = 5.1 Hz, 4H), 2.89(d, J = 18.4 Hz, 1H), 2.28 (s, 3H); MS m/z 552.30 (M + 1). |

TABLE 1-continued

| Compound Number | Structure | Physical Data ¹H NMR 400 MHz (DMSO-d₆) and/or MS (m/z) |
|---|---|---|
| 31 | 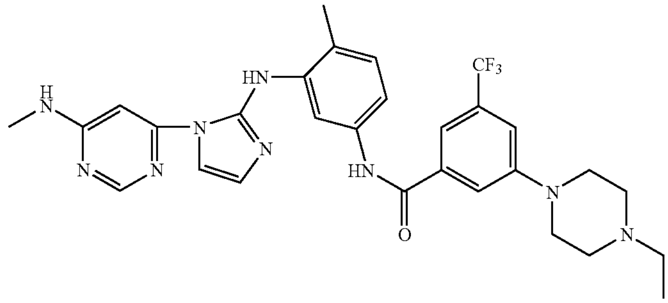 | ¹H NMR 600 MHz (DMSO-d₆) δ11.39(bs, 0.5H), 11.13(bs, 0.5H), 10.46(s, 1H), 8.54(bs, 0.5H), 8.43(s, 0.5H), 8.34(bs, 1H), 7.85(s, 1H), 7.78(s, 1H), 7.75(s, 1H), 7.64-7.54(m, 1H), 7.53-7.47(m, 2H), 7.29(d, J = 8.2 Hz, 1H), 7.07(bs, 1H), 6.68(s, 1H), 4.18-4.04(m, 2H), 3.66-3.56(m, 2H), 3.28-3.20(m, 2H), 3.20-3.08(m, 4H), 2.96-2.84(m, 3H), 2.31(s, 3H), 1.27(t, J = 8.2 Hz, 3H); MS m/z 579.30 (M + 1). |
| 32 | 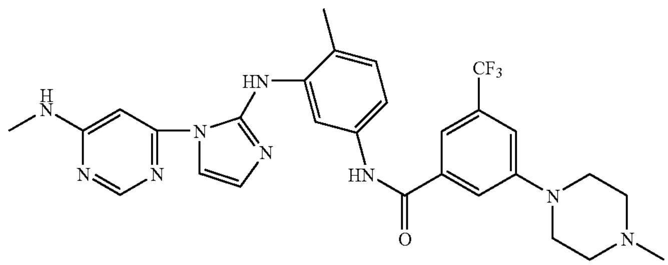 | ¹H NMR 600 MHz (DMSO-d₆) δ11.39(bs, 0.5H), 11.13(bs, 0.5H), 10.45(s, 1H), 8.53(bs, 0.5H), 8.43(s, 0.5H), 8.33(bs, 1H), 7.85(s, 1H), 7.79(s, 1H), 7.74(s, 1H), 7.64-7.54(m, 1H), 7.53-7.47(m, 2H), 7.29(d, J = 9.2 Hz, 1H), 7.08(bs, 1H), 6.68(s, 1H), 4.16-4.04(m, 2H), 3.60-3.48(m, 2H), 3.24-3.08(m, 4H), 2.96-2.84(m, 6H), 2.30(s, 3H); MS m/z 565.30 (M + 1). |
| 33 | 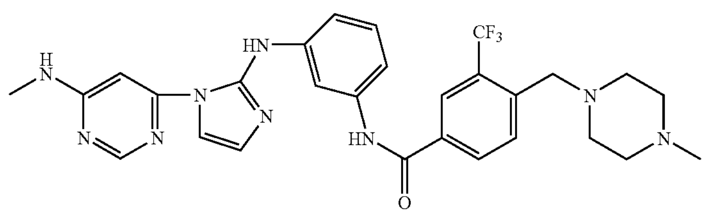 | ¹H NMR 600 MHz (DMSO-d₆) δ11.40(bs, 0.5H), 11.14(bs, 0.5H), 10.56(s, 1H), 9.78(bs, 1H), 8.54(s, 0.5H), 8.43(bs, 0.5H), 8.30(s, 1H), 8.26(d, J = 8.2 Hz, 1H), 7.95(bs, 0.5H), 7.92(d, J = 8.2 Hz, 1H), 7.87(s, 1H), 7.62(bs, 0.5H), 7.55(d, J = 8.2 Hz, 1H), 7.31(d, J = 8.2 Hz, 1H), 7.10(s, 1H), 6.69(s, 1H), 3.79(s, 2H), 3.42(d, J = 11.3 Hz, 2H), 3.07(d, J = 11.3 Hz, 2H), 2.96-2.84(m, 2H), 2.82(s, 3H), 2.43(d, J = 11.3 Hz, 2H), 2.29(s, 3H); MS m/z 579.30 (M + 1). |
| 34 | 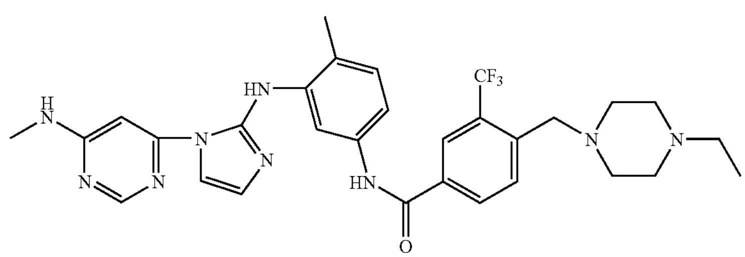 | ¹H NMR 600 MHz (DMSO-d₆) δ11.41(bs, 0.5H), 11.14(bs, 0.5H), 10.56(s, 1H), 9.55(bs, 1H), 8.54(bs, 0.5H), 8.43(bs, 0.5H), 8.30(s, 1H), 8.26(d, J = 8.2 Hz, 1H), 7.98(bs, 0.5H), 7.93(d, J = 8.2 Hz, 1H), 7.88(s, 1H), 7.62(bs, 0.5H), 7.55(d, J = 8.2 Hz, 1H), 7.31(d, J = 8.2 Hz, 1H), 7.11(s, 1H), 6.70(s, 1H), 3.80(s, 2H), 3.48(d, J = 12.3 Hz, 3H), 3.16(q, J = 7.2 Hz, 2H), 3.06-2.98(m, 2H), 2.98-2.82(m, 4H), 2.44(t, J = 11.3 Hz, 2H), 2.30(s, 3H), 1.22(t, J = 7.2 Hz, 3H); MS m/z 593.30 (M + 1). |
| 35 | 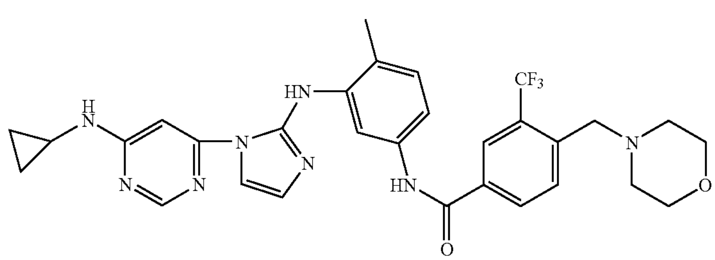 | MS m/z 593.30 (M + 1). |

TABLE 1-continued

| Compound Number | Structure | Physical Data $^1$H NMR 400 MHz (DMSO-$d_6$) and/or MS (m/z) |
|---|---|---|
| 36 | 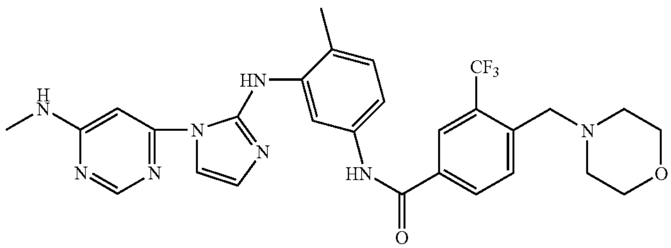 | MS m/z 567.30 (M + 1). |
| 37 | 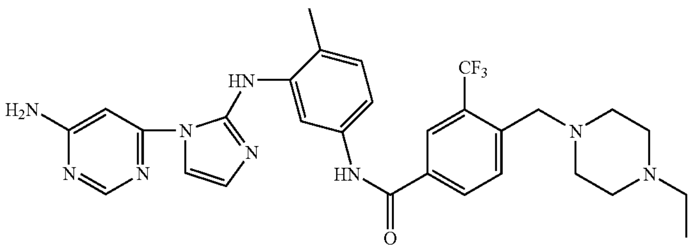 | $^1$H NMR 400 MHz (DMSO-$d_6$) δ11.19(s, 1H), 10.55(s, 1H), 8.45(s, 1H), 8.30(s, 2H), 8.26 (d, J = 8.8 Hz, 1H), 7.93(d, J = 8.2 Hz, 1H), 7.62(s, 1H), 7.54(d, J = 8.2 Hz, 1H), 7.44(s, 2H), 7.30(d, J = 8.8 Hz, 1H), 7.08(s, 1H), 6.62(s, 1H), 3.80(s, 2H), 3.52-3.42(m, 2H), 3.22-3.10(m, 2H), 3.08-2.92(m, 4H), 2.48-2.36(m, 2H), 2.29(s, 3H), 1.21(t, J = 7.5 Hz, 3H); MS m/z 580.30 (M + 1). |
| 38 | 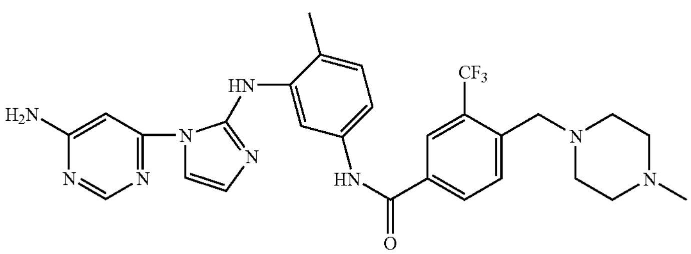 | $^1$H NMR 400 MHz (DMSO-$d_6$) δ11.19(s, 1H), 10.55(s, 1H), 8.45(s, 1H), 8.30(s, 2H), 8.26 (d, J = 9.6 Hz, 1H), 7.92(d, J = 8.2 Hz, 1H), 7.62(s, 1H), 7.54(d, J = 9.6 Hz, 1H), 7.43(s, 2H), 7.30(d, J = 8.2 Hz, 1H), 7.08(s, 1H), 6.62(s, 1H), 3.79(s, 2H), 3.46-3.36(m, 2H), 3.12-3.10(m, 2H), 2.96-2.88(m, 2H), 2.82(s, 3H), 2.46-2.34(m, 2H), 2.29(s, 3H); MS m/z 566.30 (M + 1). |
| 39 | 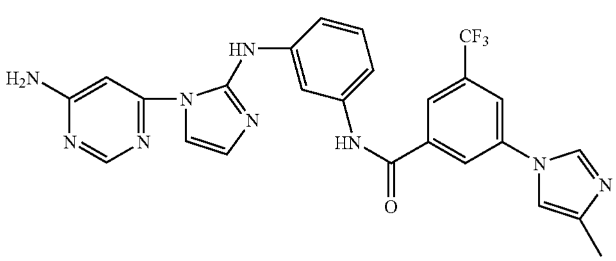 | $^1$H NMR 400 MHz (DMSO-$d_6$) δ11.20(s, 1H), 10.66(s, 1H), 9.59(s, 1H), 8.60(s, 1H), 8.50-8.40(m, 4H), 8.16(2, 1H), 7.56(s, 1H), 7.51(d, J = 9.6 Hz, 1H), 7.39(s, 2H), 7.30(d, J = 8.2 Hz, 1H), 7.01(s, 1H), 6.59(s, 1H), 2.35(s, 3H), 2.32 (s, 3H); MS m/z 534.20 (M + 1). |
| 40 | 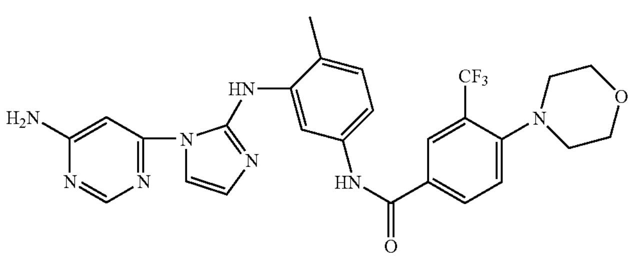 | $^1$H NMR 400 MHz (DMSO-$d_6$) δ11.19(s, 1H), 10.47(s, 1H), 8.45(s, 1H), 8.25(s, 1H), 8.18-8.10(m, 2H), 7.70-7.63(m, 1H), 7.58(d, J = 8.8 Hz, 1H), 7.51(s, 1H), 7.46(s, 2H), 7.32(d, J = 8.2 Hz, 1H), 7.14(s, 1H), 6.63(s, 1H), 2.96(t, J = 4.1 Hz, 4H), 2.92(t, J = 4.1 Hz, 4H), 2.28(s, 3H); MS m/z 539.20 (M + 1). |

TABLE 1-continued

| Compound Number | Structure | Physical Data ¹H NMR 400 MHz (DMSO-$d_6$) and/or MS (m/z) |
|---|---|---|
| 41 | 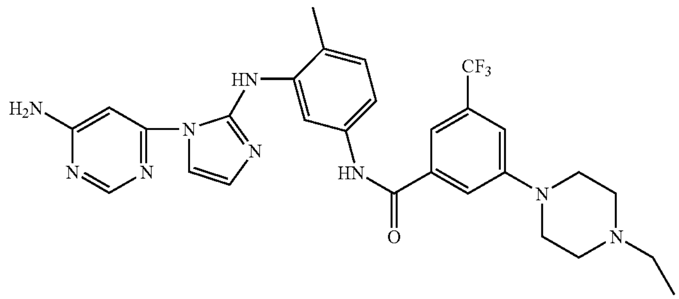 | MS m/z 566.30 (M + 1). |
| 42 | 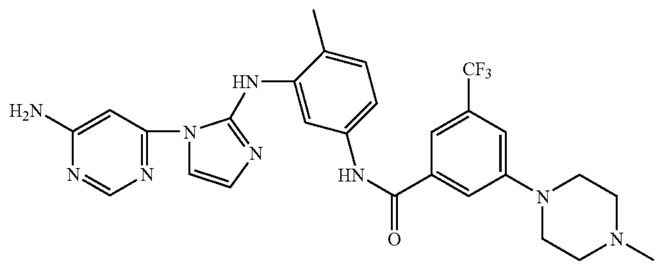 | ¹H NMR 400 MHz (DMSO-$d_6$) δ11.18(s, 1H), 10.44(s, 1H), 8.45(s, 2H), 7.78(s, 1H), 7.75(s, 2H), 7.56(d, J = 6.8 Hz, 1H), 7.51(s, 1H), 7.47(d, J = 8.2 Hz, 1H), 7.40(s, 1H), 7.27(d, J = 8.2 Hz, 1H), 7.03(s, 1H), 6.60(s, 1H), 4.16-4.04(m, 2H), 3.64-3.48(m, 2H), 3.24-3.04(m, 4H), 2.88(s, 3H), 2.30(s, 3H); MS m/z 552.30 (M + 1). |
| 43 | 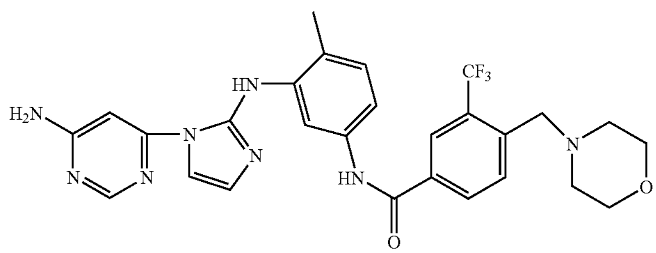 | ¹H NMR 400 MHz (DMSO-$d_6$) δ11.19(s, 1H), 10.61(s, 1H), 8.45(s, 1H), 8.40-8.24(m, 3H), 8.03(d, J = 7.5 Hz, 1H), 7.63(s, 1H), 7.55(d, J = 8.2 Hz, 1H), 7.44(s, 2H), 7.31(d, J = 8.2 Hz, 1H), 7.09(s, 1H), 6.63(s, 1H), 3.91(s, 2H), 3.82-3.68(m, 4H), 3.20-2.80(m, 4H), 2.29(s, 3H); MS m/z 553.30 (M + 1). |
| 44 | 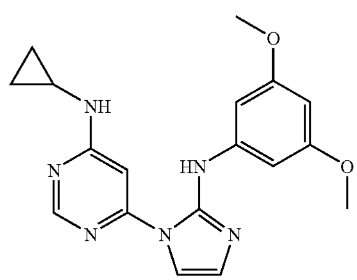 | MS m/z 353.40 (M + 1). |
| 45 | 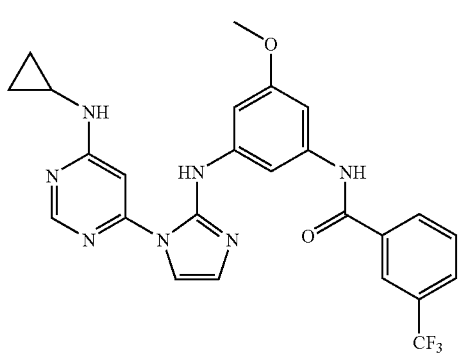 | ¹H NMR 600 MHz (DMSO-$d_6$)δ11.15(bs, 1H), 10.51(s, 1H), 8.48(bs, 1H), 8.30(s, 1H), 8.27 (d, J = 7.2 Hz, 1H), 8.21(bs, 1H), 7.99(d, J = 7.2 Hz, 1H), 7.84(bs, 1H), 7.80(t, J = 8.2 Hz, 1H), 7.58(s, 1H), 7.21(s, 1H), 7.10(bs, 1H), 6.83(bs, 1H), 3.79(s, 3H), 0.82(s, 2H), 0.53 (s, 2H); MS m/z 510.10 (M + 1). |

TABLE 1-continued

| Compound Number | Structure | Physical Data<br>¹H NMR 400 MHz (DMSO-$d_6$) and/or MS (m/z) |
|---|---|---|
| 46 | 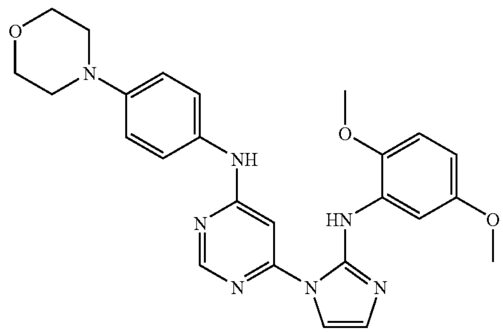 | ¹H NMR 400 MHz (DMSO-$d_6$)δ11.30(s, 1H), 9.81(s, 1H), 8.63(s, 1H), 7.78(s, 1H), 7.52(s, 1H), 7.46(d, J = 8.2 Hz, 1H), 7.05(s, 1H), 7.02-6.96(m, 3H), 6.77(s, 1H), 6.61(dd, J = 8.2, 2.0 Hz, 1H), 3.86(s, 3H), 3.78-3.73(m, 4H), 3.72(s, 3H), 3.13-3.07(m, 4H); MS m/z 474.30 (M + 1). |
| 47 | 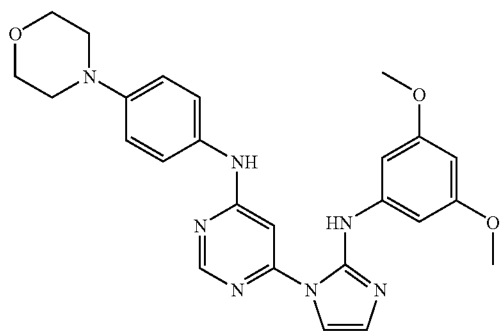 | MS m/z 474.30 (M + 1). |
| 48 | 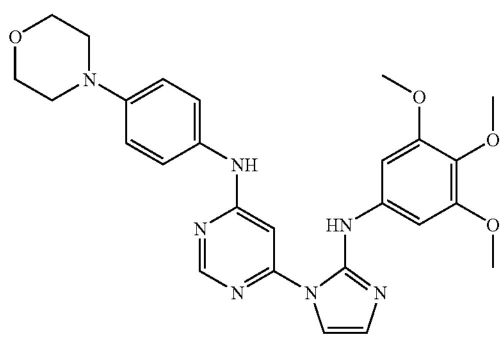 | ¹H NMR 400 MHz (DMSO-$d_6$)δ10.86(s, 1H), 9.93(s, 1H), 8.61(s, 1H), 7.67(s, 1H), 7.46 (d, J = 7.5 Hz, 2H), 7.21(d, J = 1.4 Hz, 1H), 6.99(s, 1H), 6.97(s, 1H), 6.88(s, 1H), 6.86(s, 2H), 3.79(s, 6H), 3.78-3.73(m, 4H), 3.67(s, 3H), 3.13-3.07(m, 4H); MS m/z 504.30 (M + 1). |
| 49 | 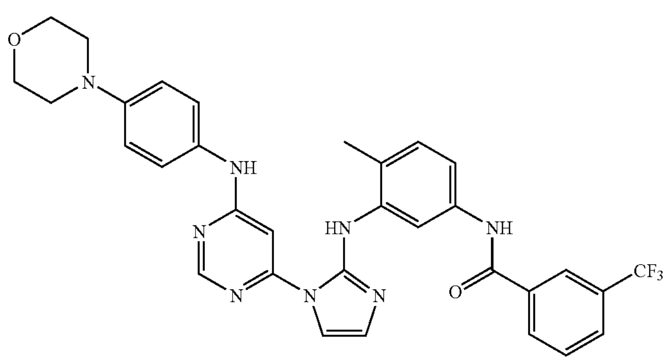 | MS m/z 615.30 (M + 1). |

TABLE 1-continued

| Compound Number | Structure | Physical Data $^1$H NMR 400 MHz (DMSO-$d_6$) and/or MS (m/z) |
|---|---|---|
| 50 | 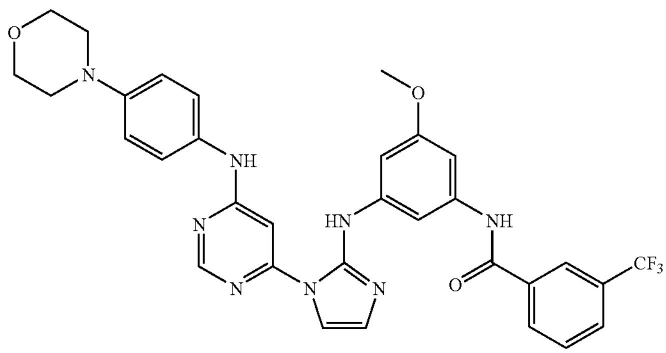 | $^1$H NMR 400 MHz (DMSO-$d_6$) δ 10.86(s, 1H), 10.55(s, 1H), 9.88(s, 1H), 8.62(s, 1H), 8.29(s, 1H), 8.26(d, J = 7.5 Hz, 1H), 7.99(d, J = 8.2 Hz, 1H), 7.80(t, J = 8.2 Hz, 1H), 7.62(s, 1H), 7.58(s, 1H), 7.50-7.40(m, 2H), 7.23(s, 1H), 7.18(s, 1H), 7.02-6.94(m, 3H), 6.86(s, 1H), 3.79(s, 3H), 3.78-3.71(m, 4H), 3.12-3.05(m, 4H); MS m/z 631.30 (M + 1). |
| 51 | 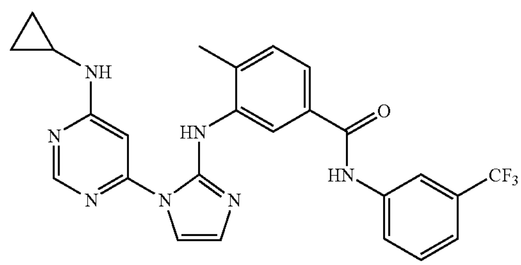 | MS m/z 494.30 (M + 1). |
| 52 | 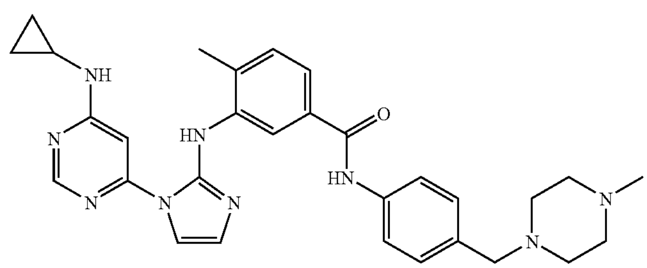 | MS m/z 538.30 (M + 1). |
| 53 | 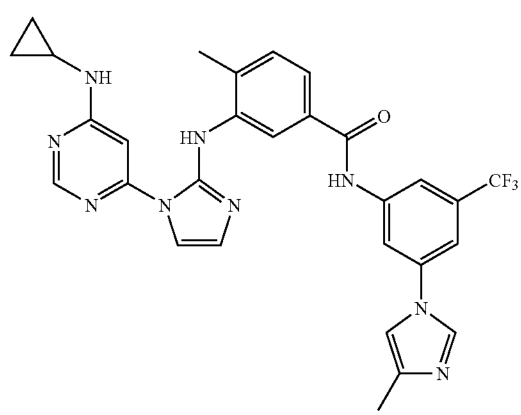 | MS m/z 574.30 (M + 1). |

TABLE 1-continued

| Compound Number | Structure | Physical Data <br> ¹H NMR 400 MHz (DMSO-$d_6$) and/or MS (m/z) |
|---|---|---|
| 54 | 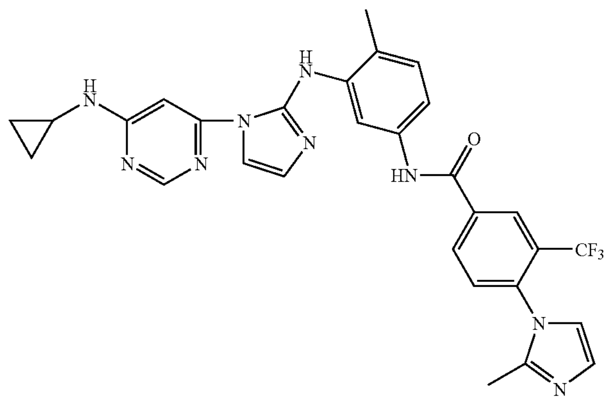 | ¹H NMR 600 MHz (DMSO-$d_6$) δ11.31(bs, 1H), 10.76(s, 1H), 8.58(s, 1H), 8.54(d, J = 8.2 Hz, 1H), 8.49(s, 1H), 8.44(bs, 1H), 8.24(bs, 1H), 8.07(d, J = 8.2 Hz, 1H), 7.97(s, 1H), 7.91(bs, 1H), 7.84(d, J = 2.0 Hz, 1H), 7.56(d, J = 7.2 Hz, 1H), 7.32 (d, J = 8.2 Hz, 1H), 7.08(s, 1H), 6.86(bs, 1H), 2.64-2.60(m, 1H), 2.41(s, 3H), 2.33(s, 3H), 0.85(bs, 2H), 0.55(bs, 2H); MS m/z 573.22 (M + 1). |
| 55 | 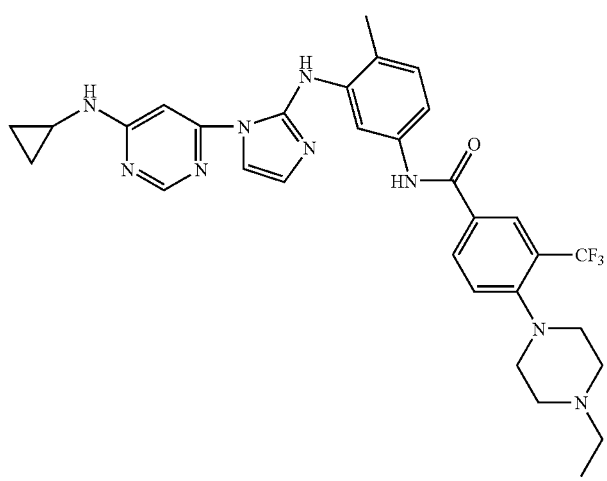 | MS m/z 605.28 (M + 1). |
| 56 | 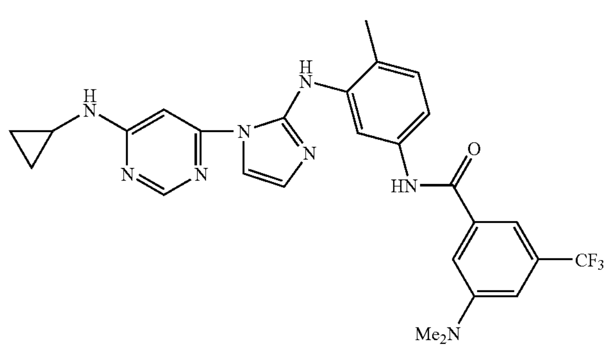 | MS m/z 536.23 (M + 1). |

TABLE 1-continued

| Compound Number | Structure | Physical Data <br> ¹H NMR 400 MHz (DMSO-d₆) and/or MS (m/z) |
|---|---|---|
| 57 | 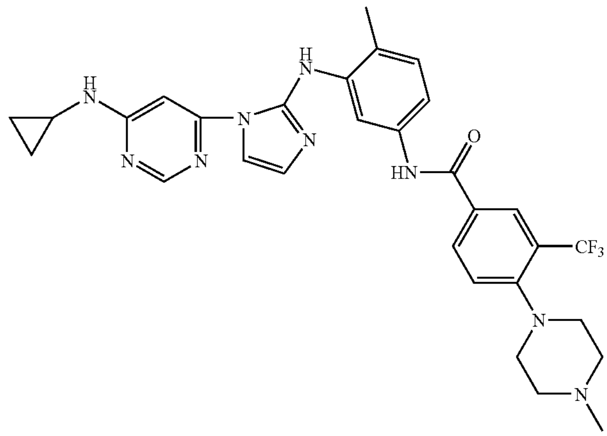 | MS m/z 591.27 (M + 1). |
| 58 | 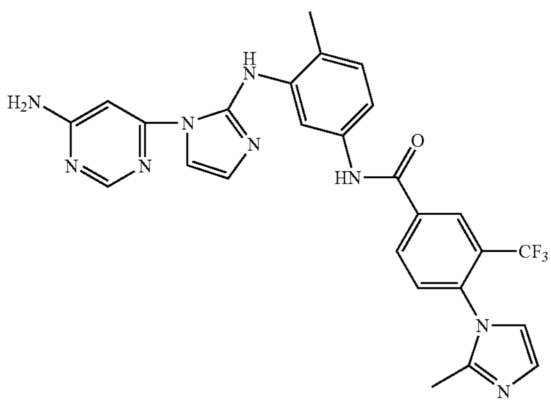 | ¹H NMR 600 MHz (DMSO-d₆) δ11.19(s, 1H), 10.75(s, 1H), 8.58(s, 1H), 8.53(d, J = 8.2 Hz, 1H), 8.46(s, 1H), 8.06(d, J = 8.2 Hz, 1H), 7.96(s, 1H), 7.84(s, 1H), 7.58(s, 1H), 7.54(d, J = 8.2 Hz, 1H), 7.40(s, 2H), 7.31(d, J = 8.2 Hz, 1H), 7.05(s, 1H), 6.61(s, 2H), 2.40(s, 3H), 2.32 (s, 3H); MS m/z 533.19 (M + 1). |
| 59 | 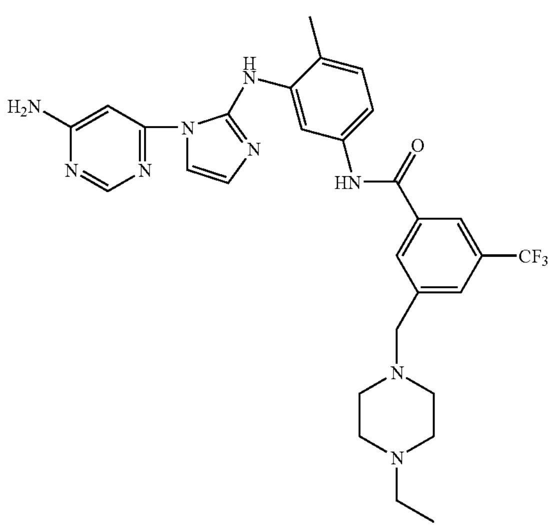 | ¹H NMR 600 MHz (DMSO-d₆) δ11.19(s, 1H), 10.56(s, 1H), 8.46(s, 1H), 8.28(s, 1H), 8.23(s, 1H), 7.93(s, 1H), 7.62(s, 1H), 7.54(d, J = 7.2 Hz, 1H), 7.43(s, 2H), 7.31(d, J = 8.2 Hz, 1H), 7.08(s, 1H), 6.62(s, 1H), 3.84(s, 2H), 3.52-3.42(m, 2H), 3.13(q, J = 7.2 Hz, 2H), 3.08-3.96(m, 4H), 2.30(s, 3H), 1.20(t, J = 7.2 Hz, 3H); MS m/z 579.27 (M + 1). |

TABLE 1-continued

| Compound Number | Structure | Physical Data $^1$H NMR 400 MHz (DMSO-$d_6$) and/or MS (m/z) |
|---|---|---|
| 60 | 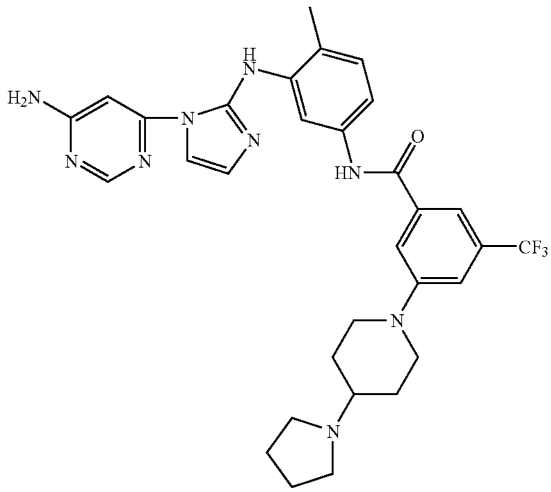 | $^1$H NMR 600 MHz (DMSO-$d_6$) δ11.18(s, 1H), 10.43(s, 1H), 8.45(s, 1H), 7.75(s, 1H), 7.70(s, 0.5H), 7.66(s, 1H), 7.60(s, 1H), 7.54(s, 05H), 7.52-7.48(m, 1H), 7.44(s, 1H), 7.41(s, 2H), 7.29(d, J = 8.2 Hz, 1H), 7.06(s, 1H), 6.62(s, 1H), 4.10-4.00(m, 1H), 3.60-3.52(m, 2H), 3.40-3.30(m, 2H), 3.16-3.06(m, 2H), 2.92-2.82(m, 2H), 2.30(s, 3H), 2.20-2.10(m, 2H), 2.06-1.98(m, 2H), 1.90-1.80(m, 2H), 1.72-1.60(m, 2H); MS m/z 605.28 (M + 1). |
| 61 | 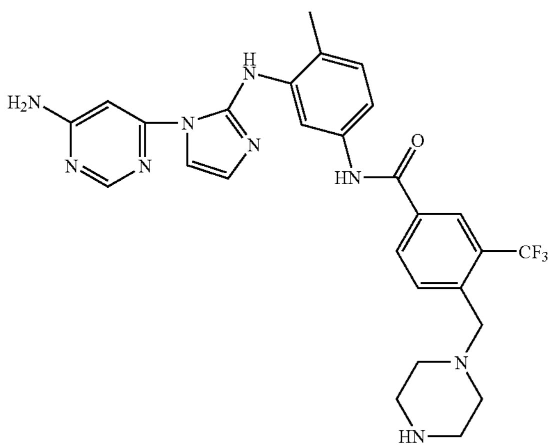 | $^1$H NMR 600 MHz (DMSO-$d_6$) δ11.19(s, 1H), 10.55(s, 1H), 8.66(s, 2H), 8.45(s, 1H), 8.29(s, 1H), 8.26(d, J = 8.2 Hz, 1H), 7.94(d, J = 8.2 Hz, 1H), 7.64(s, 1H), 7.56(d, J = 8.2 Hz, 1H), 7.44(s, 1H), 7.31(d, J = 8.2 Hz, 1H), 7.10(s, 1H), 6.63(s, 1H), 3.78(s, 2H), 3.16-3.10(m, 4H), 2.66-2.60(m, 4H), 2.29(s, 3H); MS m/z 551.24 (M + 1). |
| 62 | 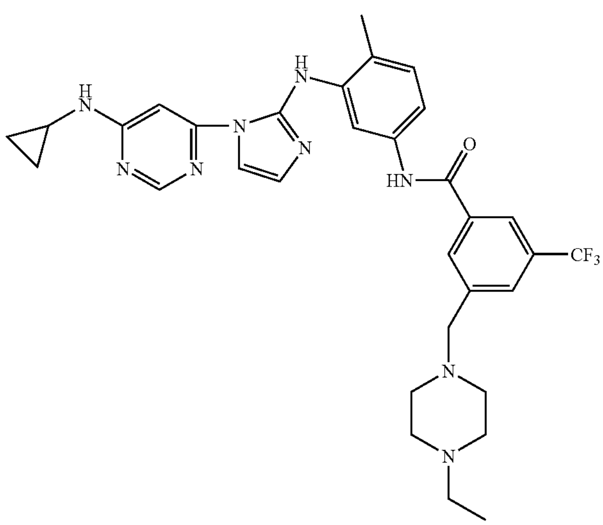 | $^1$H NMR 600 MHz (DMSO-$d_6$) δ11.31(s, 1H), 10.56(s, 1H), 8.49(bs, 1H), 8.34(bs, 1H), 8.29(s, 1H), 8.23(s, 1H), 7.93(s, 1H), 7.54(d, J = 7.2 Hz, 1H), 7.31(d, J = 8.2 Hz, 1H), 7.10(s, 1H), 6.86(bs, 1H), 3.84(s, 2H), 3.52-3.44(m, 4H), 3.14(q, J = 7.2 Hz, 2H), 3.08-2.96(m, 4H), 2.48-2.40(m, 1H), 2.31(s, 3H), 1.20(t, J = 7.2 Hz, 3H), 0.85(bs, 2H), 0.55(bs, 2H); MS m/z 619.30 (M + 1). |

TABLE 1-continued

| Compound Number | Structure | Physical Data $^1$H NMR 400 MHz (DMSO-$d_6$) and/or MS (m/z) |
|---|---|---|
| 63 | 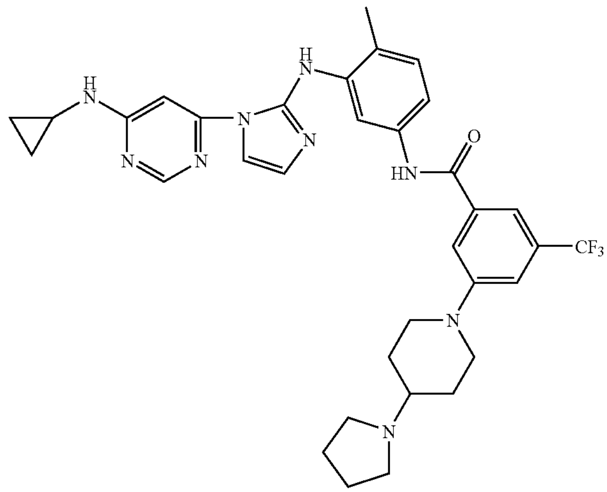 | $^1$H NMR 600 MHz (DMSO-$d_6$) δ 11.30(bs, 1H), 10.43(s, 1H), 9.69(s, 1H), 8.48(s, 1H), 8.33(s, 1H), 8.24(s, 1H), 7.92(s, 1H), 7.75(s, 1H), 7.66(s, 1H), 7.56-7.48(m, 1H), 7.44(s, 1H), 7.30(d, J = 8.2 Hz, 1H), 7.09 (s, 1H), 6.86(bs, 1H), 4.06(d, J = 13.3 Hz, 2H), 3.40-3.28(m, 2H), 3.16-3.06(m, 2H), 2.88(t, J = 12.3 Hz, 2H), 2.64-2.58(m, 1H), 2.54-2.50(m, 1H), 2.31(s, 3H), 2.15(d, J = 11.3 Hz, 2H), 2.08-1.96(m, 2H), 1.90-1.80 (m, 2H), 1.72-1.62(m, 2H), 0.84(bs, 2H), 0.54(bs, 2H); MS m/z 645.32 (M + 1). |
| 64 | 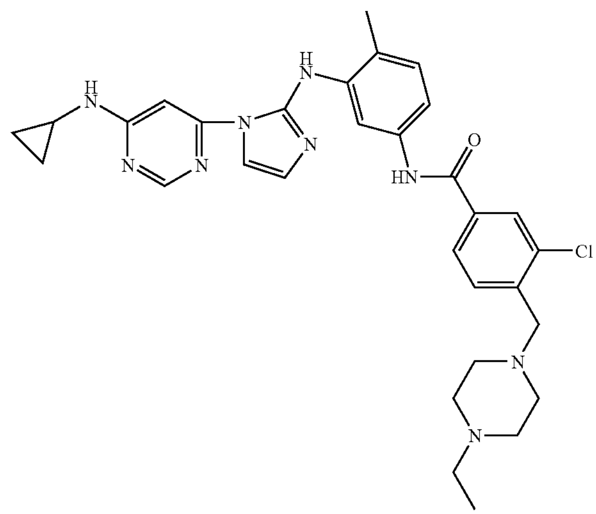 | MS m/z 585.27 (M + 1). |
| 65 | 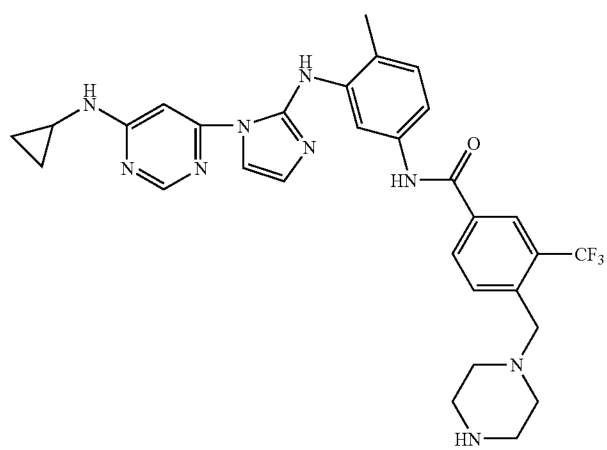 | $^1$H NMR 600 MHz (DMSO-$d_6$) δ 11.30(bs, 1H), 10.55(s, 1H), 8.66(s, 1H), 8.48(s, 1H), 8.29(s, 1H), 8.26(s, 1H), 8.25(s, 1H), 7.95(s, 1H), 7.94(s, 1H), 7.54(d, J = 7.2 Hz, 1H), 7.30 (d, J = 8.2 Hz, 1H), 7.10(s, 1H), 6.86(bs, 1H), 3.78(s, 2H), 3.16-3.10(m, 4H), 2.66-2.60(m, 4H), 2.54-2.50(m, 1H), 2.30(s, 3H), 0.85(bs, 2H), 0.54(bs, 2H); MS m/z 591.27 (M + 1). |

TABLE 1-continued
| Compound Number | Structure | Physical Data $^1$H NMR 400 MHz (DMSO-$d_6$) and/or MS (m/z) |
|---|---|---|
| 66 | 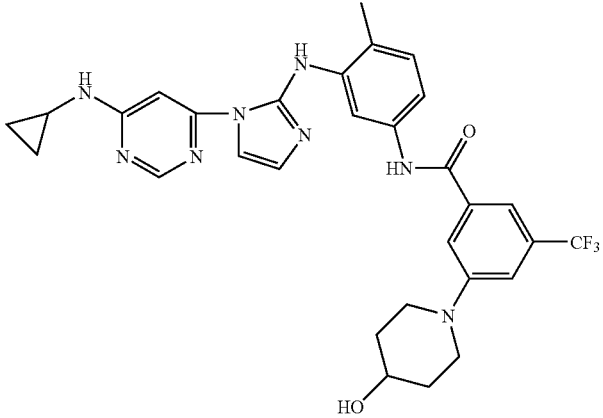 | MS m/z 592.25 (M + 1). |
| 67 | 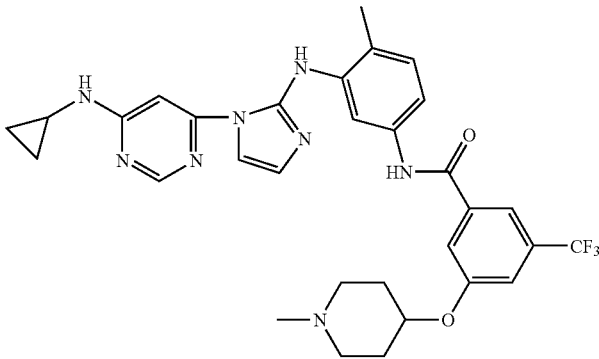 | MS m/z 606.27 (M + 1). |
| 68 | 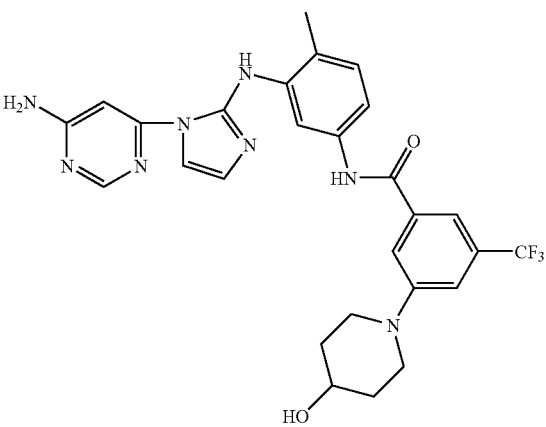 | MS m/z 552.22 (M + 1). |

TABLE 1-continued

| Compound Number | Structure | Physical Data<br>¹H NMR 400 MHz (DMSO-$d_6$) and/or MS (m/z) |
|---|---|---|
| 69 | 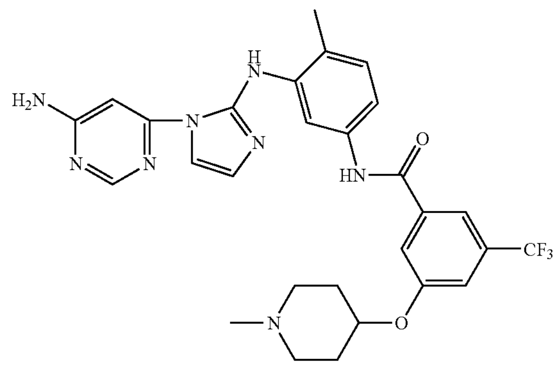 | MS m/z 566.24 (M + 1). |
| 70 | 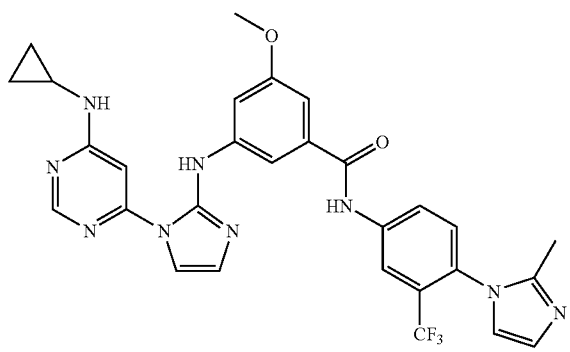 | MS m/z 590.22 (M + 1). |
| 71 | 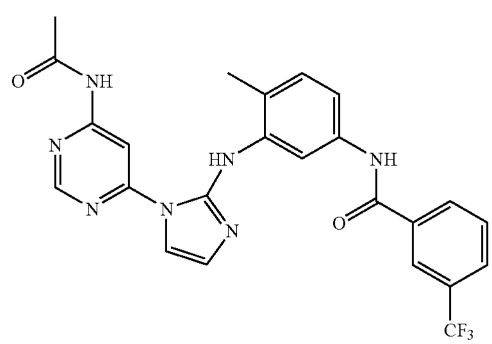 | MS m/z 496.16 (M + 1). |
| 72 | 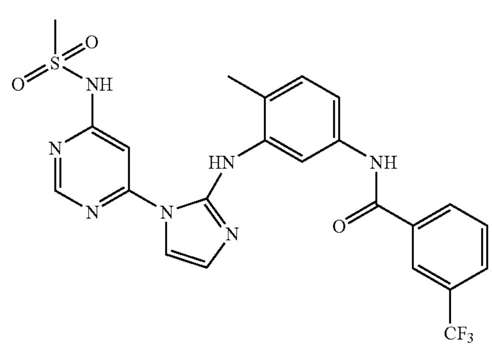 | MS m/z 532.13 (M + 1). |

TABLE 1-continued
| Compound Number | Structure | Physical Data $^1$H NMR 400 MHz (DMSO-$d_6$) and/or MS (m/z) |
|---|---|---|
| 73 | 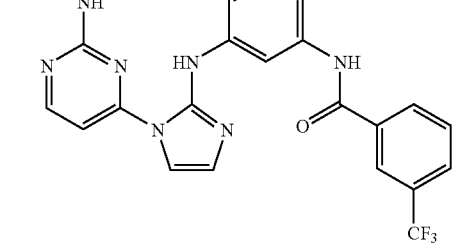 | MS m/z 494.18 (M + 1). |
| 74 | 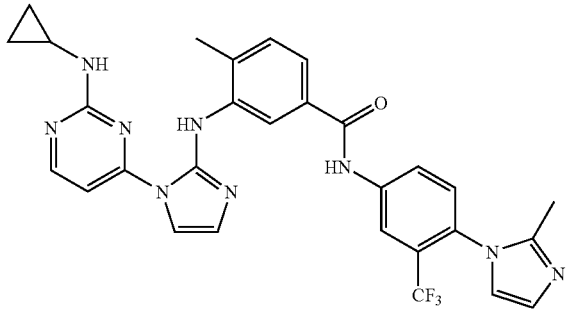 | MS m/z 574.22 (M + 1). |
| 75 | 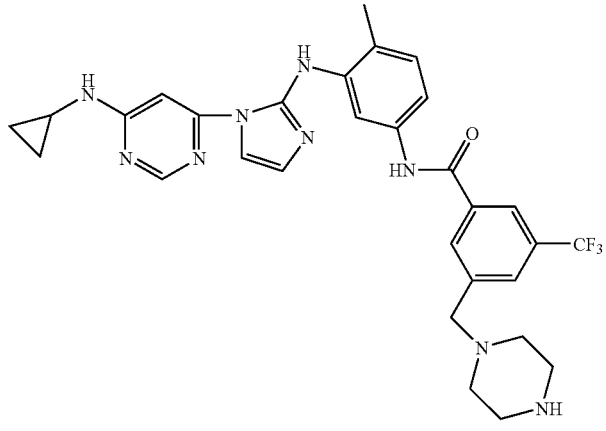 | MS m/z 592.27 (M + 1). |
| 76 | 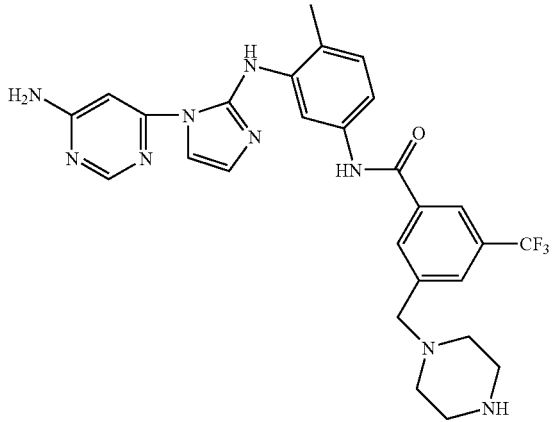 | MS m/z 552.24 (M + 1). |

TABLE 1-continued

| Compound Number | Structure | Physical Data $^1$H NMR 400 MHz (DMSO-$d_6$) and/or MS (m/z) |
|---|---|---|
| 77 | 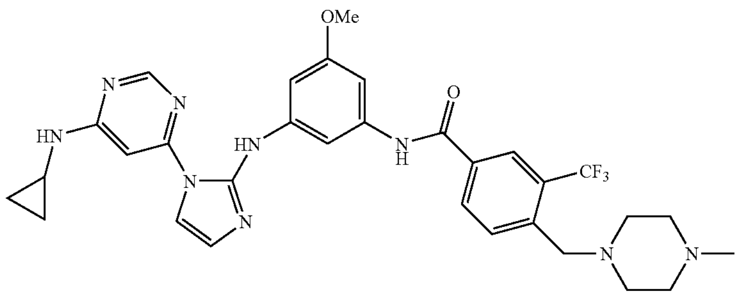 | MS m/z 622.25 (M + 1). |
| 78 | 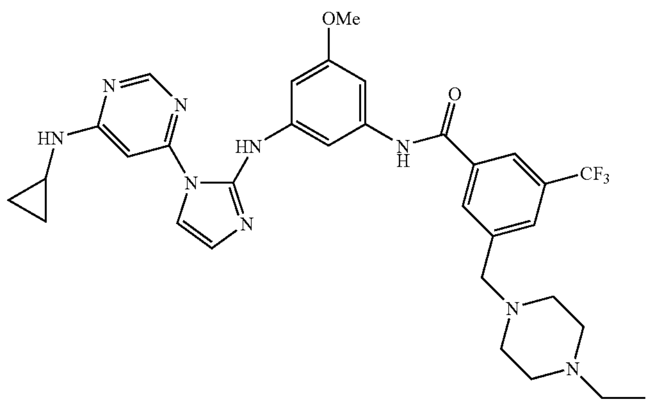 | MS m/z 636.29 (M + 1). |
| 79 | 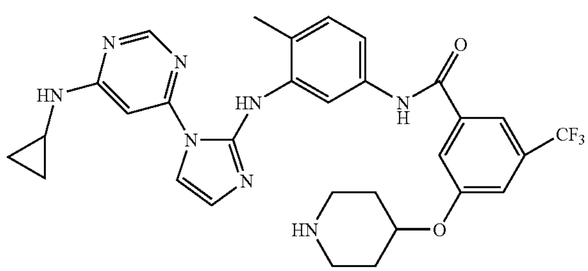 | MS m/z 593.25 (M + 1). |
| 80 | 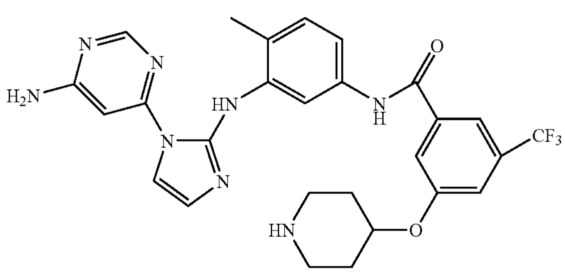 | MS m/z 553.22 (M + 1). |

TABLE 1-continued
| Compound Number | Structure | Physical Data $^1$H NMR 400 MHz (DMSO-$d_6$) and/or MS (m/z) |
|---|---|---|
| 81 | 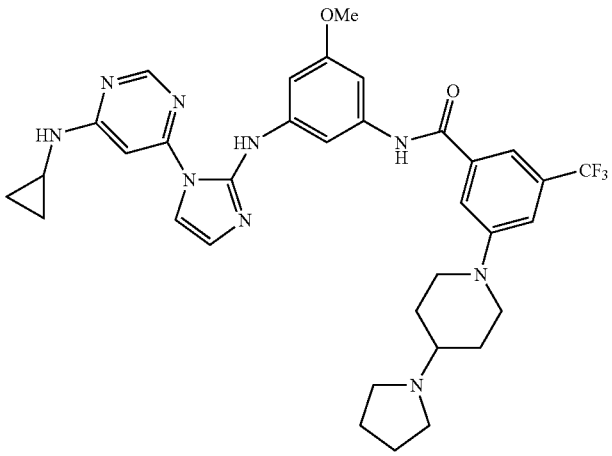 | MS m/z 662.30 (M + 1). |
| 82 | 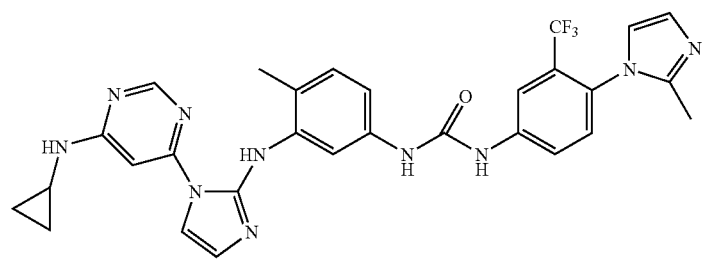 | MS m/z 589.23 (M + 1). |
| 83 | 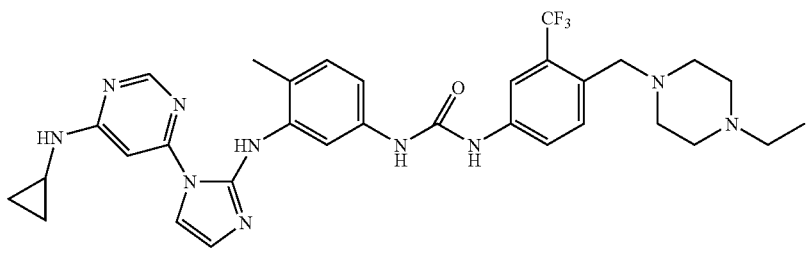 | MS m/z 635.31 (M + 1). |
| 84 | 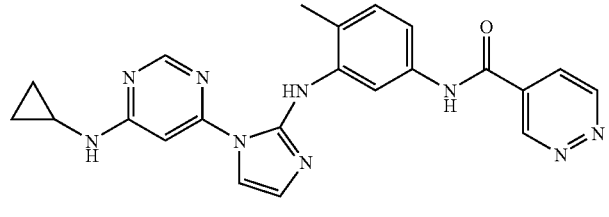 | MS m/z 428.5 (M + 1). |
| 85 | 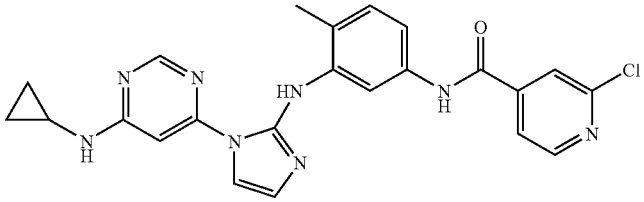 | MS m/z 461.2 (M + 1). |

TABLE 1-continued

| Compound Number | Structure | Physical Data ¹H NMR 400 MHz (DMSO-$d_6$) and/or MS (m/z) |
|---|---|---|
| 86 | 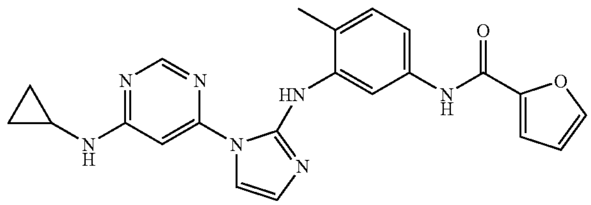 | MS m/z 416.4 (M + 1). |
| 87 | 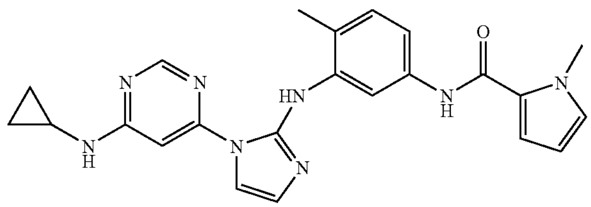 | MS m/z 429.5 (M + 1). |
| 88 | 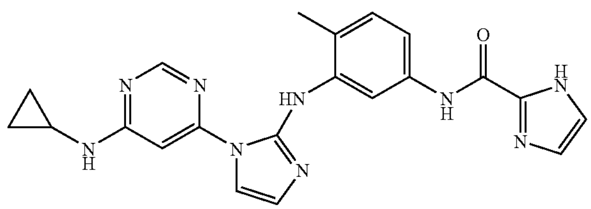 | MS m/z 416.5 (M + 1). |
| 89 | 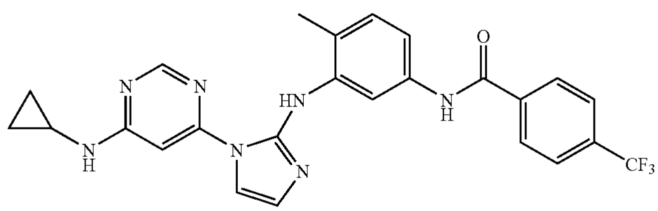 | MS m/z 494.5 (M + 1). |
| 90 | 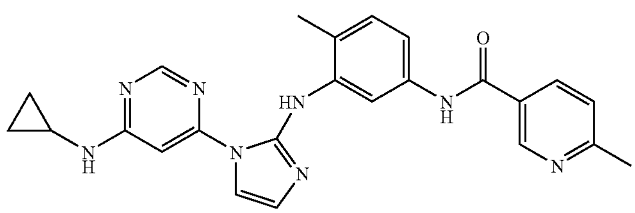 | MS m/z 441.5 (M + 1). |
| 91 | 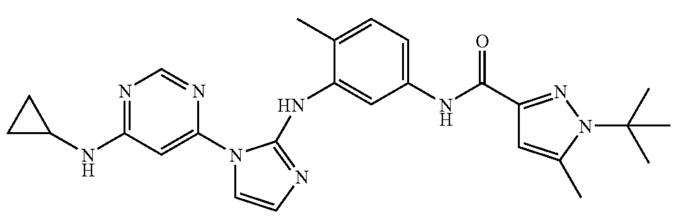 | MS m/z 486.6 (M + 1). |
| 92 | 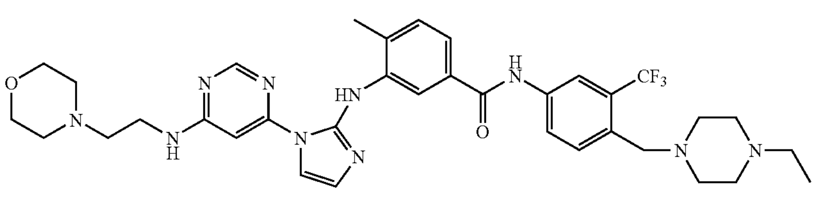 | MS m/z 693.8 (M + 1). |

TABLE 1-continued

| Compound Number | Structure | Physical Data ¹H NMR 400 MHz (DMSO-d₆) and/or MS (m/z) |
|---|---|---|
| 93 | 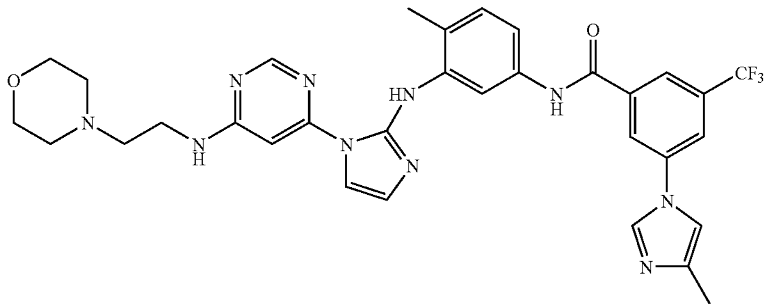 | MS m/z 647.7 (M + 1). |
| 94 | 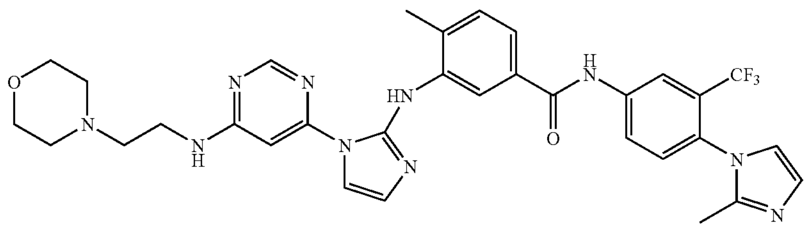 | MS m/z 647.7 (M + 1). |
| 95 | 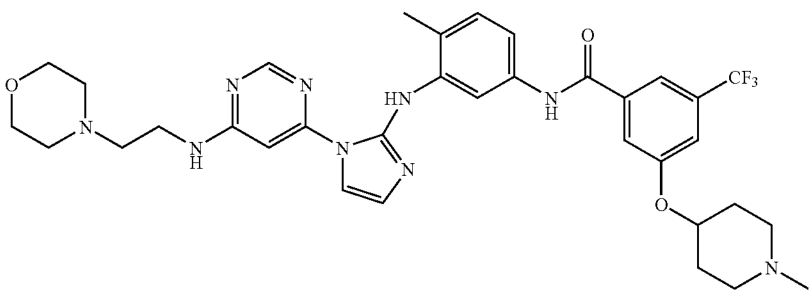 | MS m/z 680.8 (M + 1). |
| 96 | 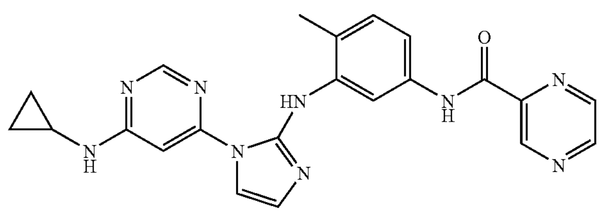 | MS m/z 428.5 (M + 1). |
| 97 | 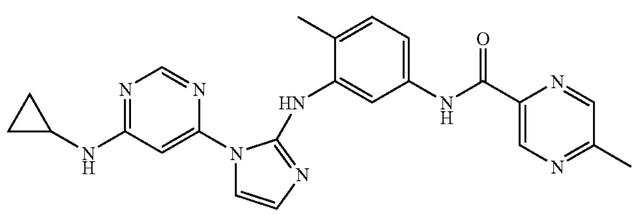 | MS m/z 442.3 (M + 1). |
| 98 | 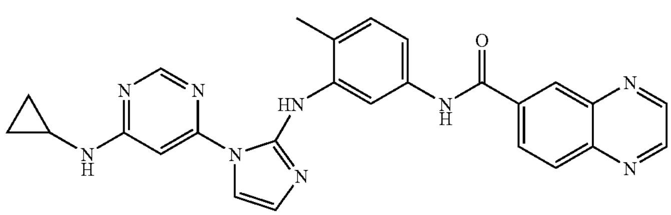 | MS m/z 478.5 (M + 1). |

TABLE 1-continued
| Compound Number | Structure | Physical Data $^1$H NMR 400 MHz (DMSO-$d_6$) and/or MS (m/z) |
|---|---|---|
| 99 | 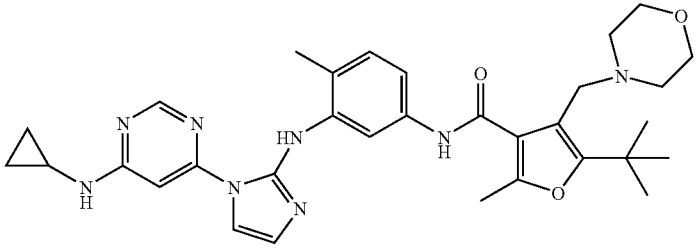 | MS m/z 585.7 (M + 1). |
| 100 | 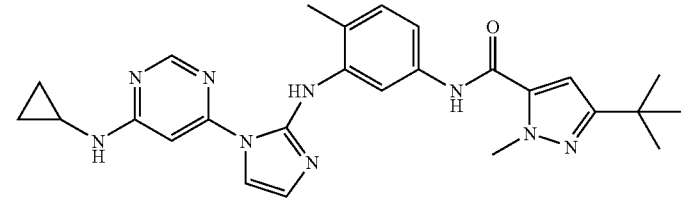 | MS m/z 486.6 (M + 1). |
| 101 | 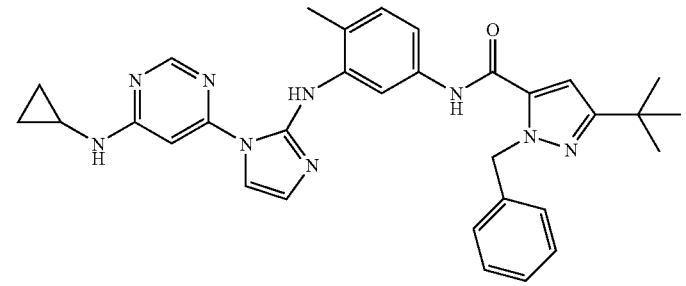 | MS m/z 562.7 (M + 1). |
| 102 | 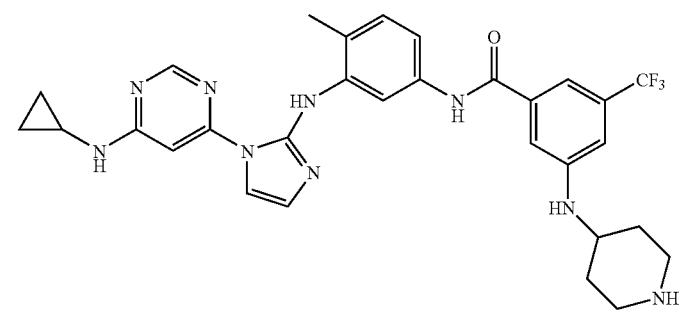 | MS m/z 592.6 (M + 1). |
| 103 | 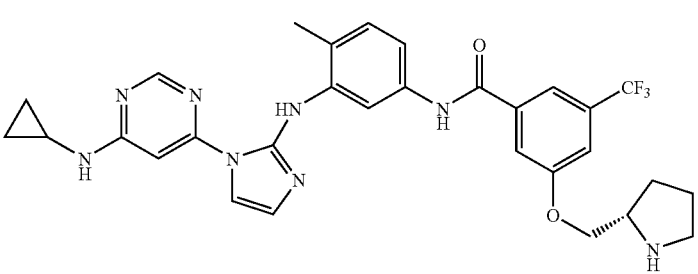 | MS m/z 593.6 (M + 1). |
| 104 | 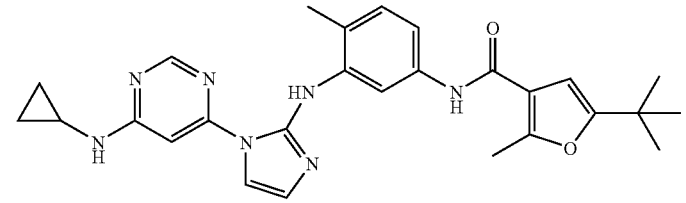 | MS m/z 486.6 (M + 1). |

TABLE 1-continued

| Compound Number | Structure | Physical Data ¹H NMR 400 MHz (DMSO-$d_6$) and/or MS (m/z) |
|---|---|---|
| 105 | 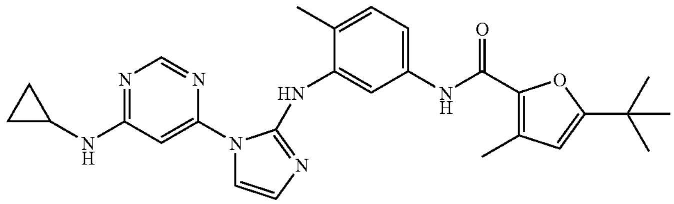 | MS m/z 486.6 (M + 1). |
| 106 | 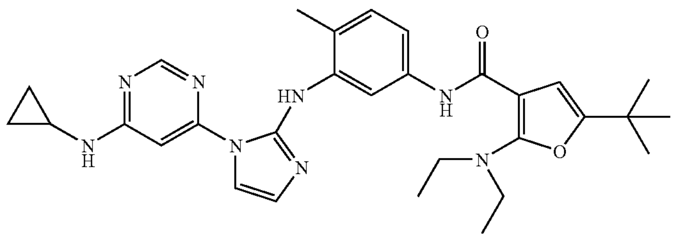 | MS m/z 543.7 (M + 1). |
| 107 | 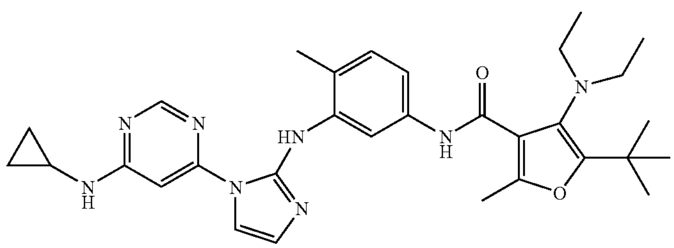 | MS m/z 557.7 (M + 1). |
| 108 | 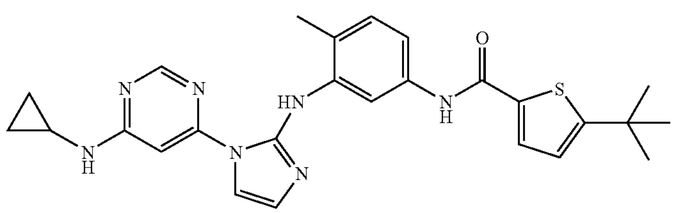 | MS m/z 488.6 (M + 1). |
| 109 | 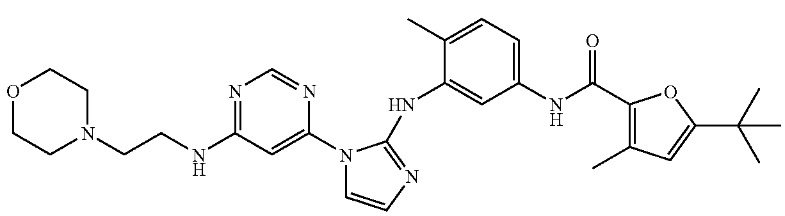 | MS m/z 559.7 (M + 1). |
| 110 | 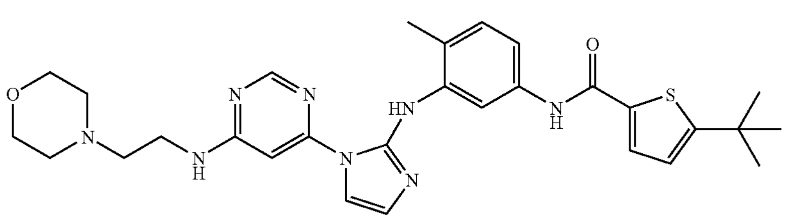 | MS m/z 561.7 (M + 1). |

TABLE 1-continued

| Compound Number | Structure | Physical Data<br>¹H NMR 400 MHz (DMSO-$d_6$) and/or MS (m/z) |
|---|---|---|
| 111 | 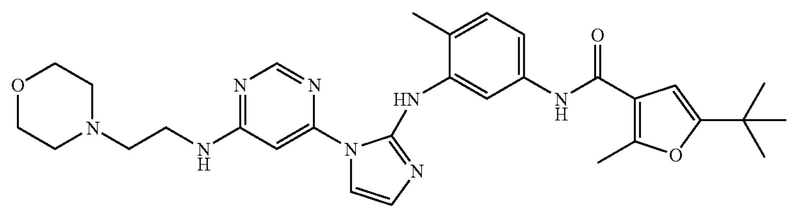 | MS m/z 559.7 (M + 1). |
| 112 | 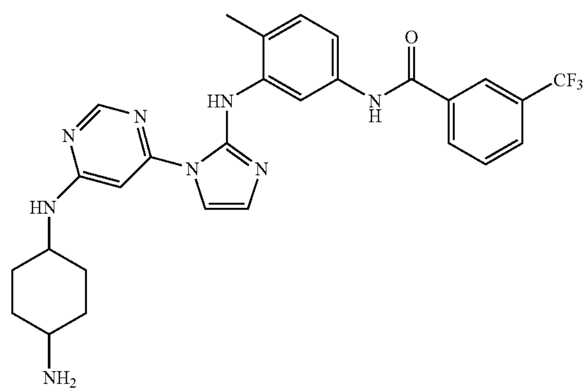 | MS m/z 551.2 (M + 1). |
| 113 | 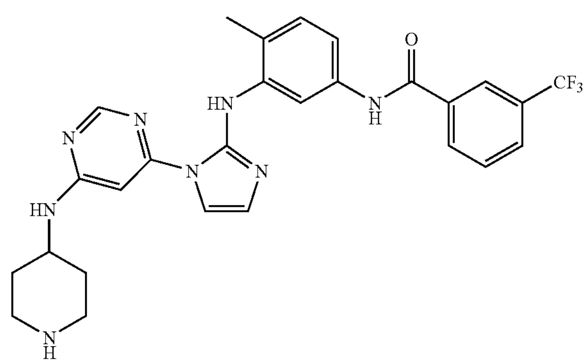 | MS m/z 537.2 (M + 1). |
| 114 | 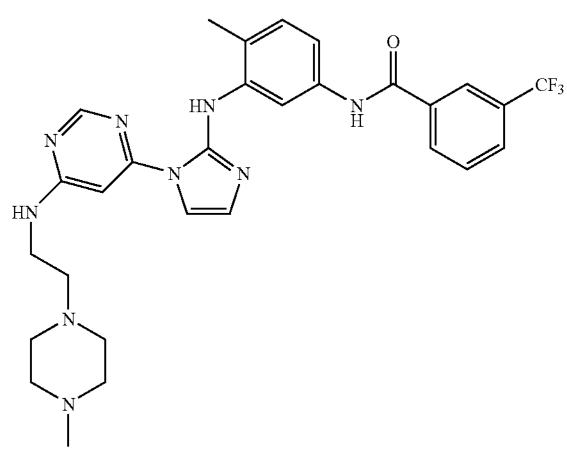 | MS m/z 580.3 (M + 1). |

TABLE 1-continued

| Compound Number | Structure | Physical Data $^1$H NMR 400 MHz (DMSO-$d_6$) and/or MS (m/z) |
|---|---|---|
| 115 | 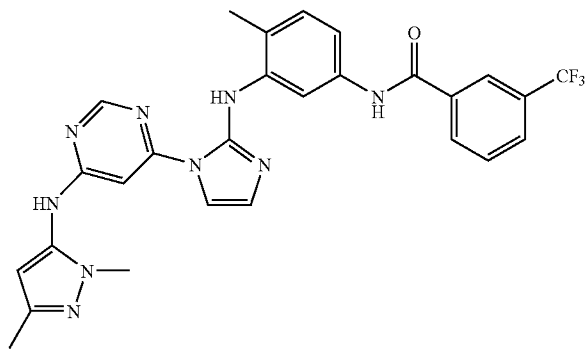 | MS m/z 548.2 (M + 1). |
| 116 | 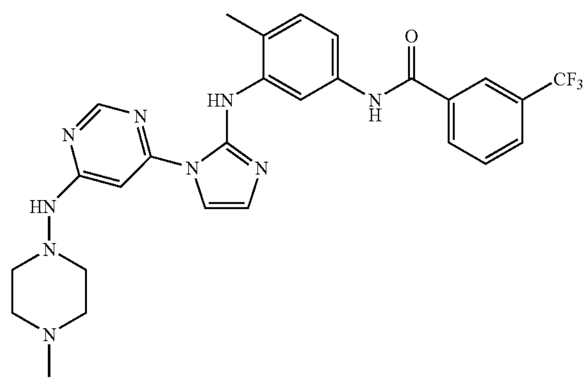 | MS m/z 552.2 (M + 1). |
| 117 | 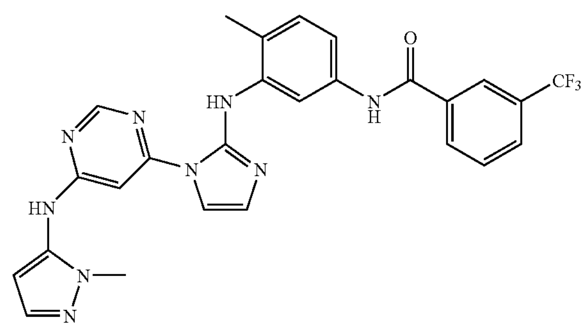 | MS m/z 534.2 (M + 1). |
| 118 | 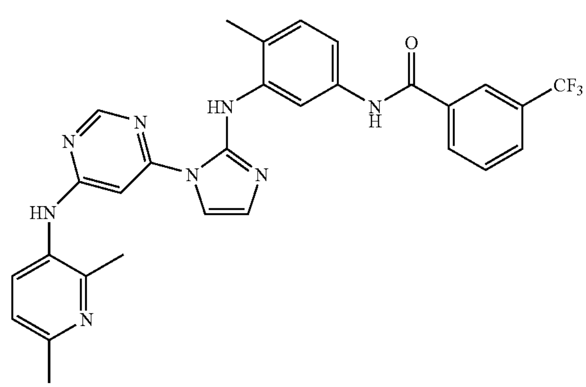 | MS m/z 559.2 (M + 1). |

TABLE 1-continued

| Compound Number | Structure | Physical Data<br>¹H NMR 400 MHz (DMSO-$d_6$) and/or MS (m/z) |
|---|---|---|
| 119 | 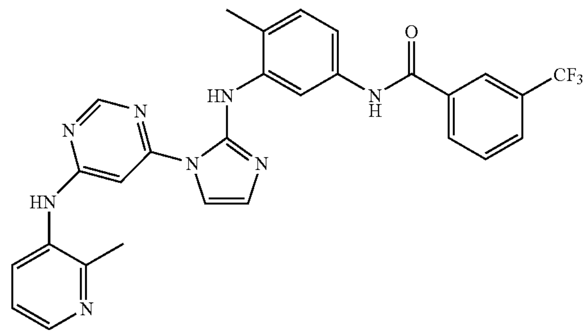 | MS m/z 545.2 (M + 1). |
| 120 | 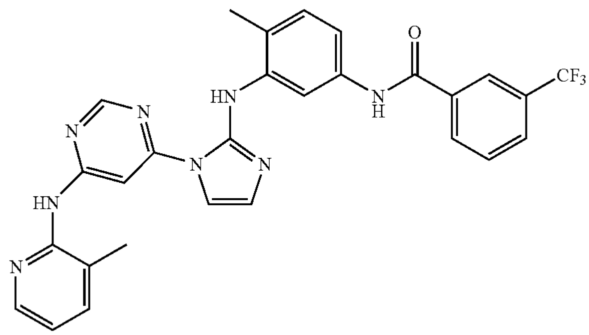 | MS m/z 545.2 (M + 1). |
| 121 | 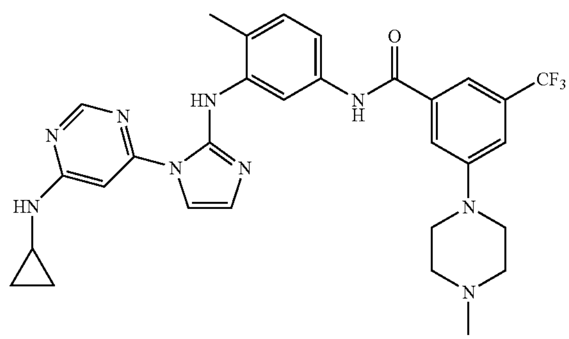 | 1H NMR 400 MHz (DMSO-d6) 11.17(br, 1H), 10.36(s, 1H), 8.75(s, 1H), 8.49(s, 1H), 8.11(br, 1H), 7.75(s, 1H), 7.66(s, 1H), 7.36(br, 1H), 7.32(d, 1H), 7.17(d, 1H), 6.88 (s, 1H), 6.73(br, 1H), 3.33(m, 4H), 2.50(m, 4H), 2.34(s, 3H), 2.26(s, 3H), 1.99(s, 1H), 0.82 (m, 2H), 0.53(m, 2H); MS m/z 592.3 (M + 1). |
| 122 | 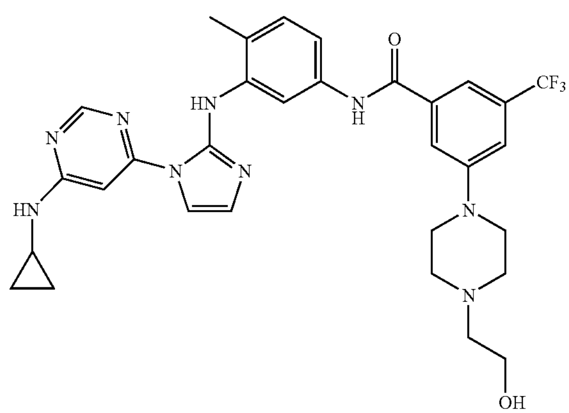 | 1H NMR 400 MHz (DMSO-d6) 11.14(br, 1H), 10.36(s, 1H), 8.75(s, 1H), 8.50(s, 1H), 8.08(br, 1H), 7.74(br, 2H), 7.65(b, 2H), 7.35(s, 1H), 7.32(d, 1H), 7.17(d, 1H), 6.89 (s, 1H), 4.48(br, 1H), 3.56(br, 1H), 3.34(m, 6H), 2.60, 2.50 (m, 6H), 2.34(s, 3H), 0.83(m, 2H), 0.53(m, 2H); MS m/z 622.3 (M + 1). |

TABLE 1-continued
| Compound Number | Structure | Physical Data<br>¹H NMR 400 MHz (DMSO-$d_6$) and/or MS (m/z) |
|---|---|---|
| 123 | 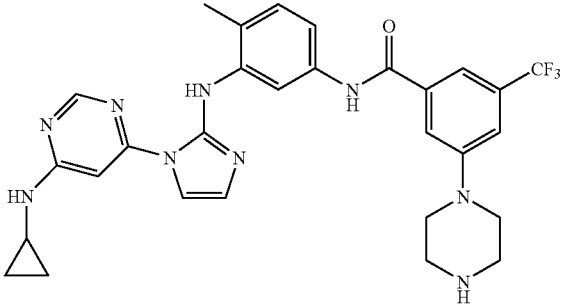 | MS m/z 578.3 (M + 1). |
| 124 | 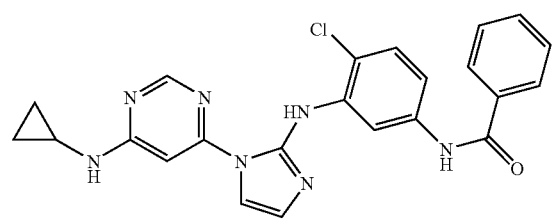 | MS m/z 446.2 (M + 1) |
| 125 | 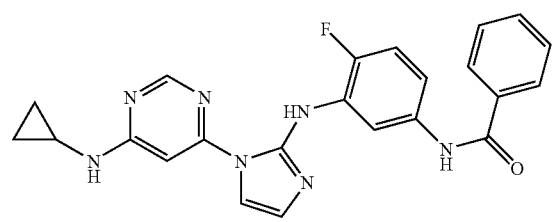 | MS m/z 430.2 (M + 1) |
| 126 | 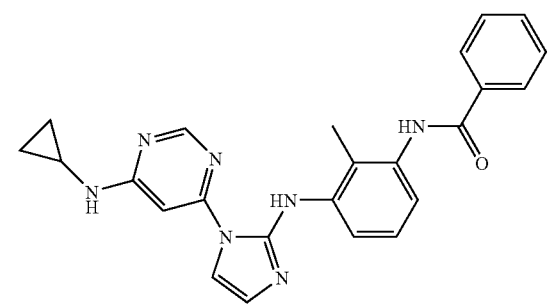 | MS m/z 426.2 (M + 1) |
| 127 | 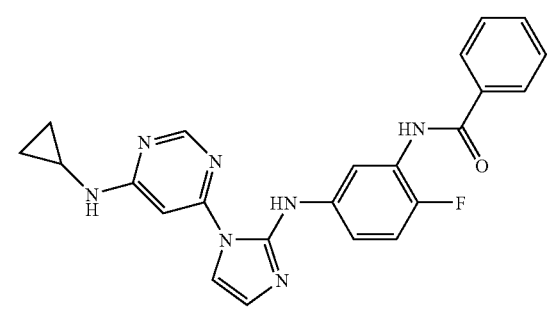 | MS m/z 430.2 (M + 1) |

TABLE 1-continued

| Compound Number | Structure | Physical Data $^1$H NMR 400 MHz (DMSO-$d_6$) and/or MS (m/z) |
|---|---|---|
| 128 | 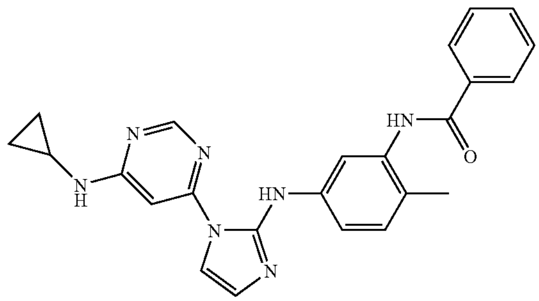 | MS m/z 426.2 (M + 1) |
| 129 | 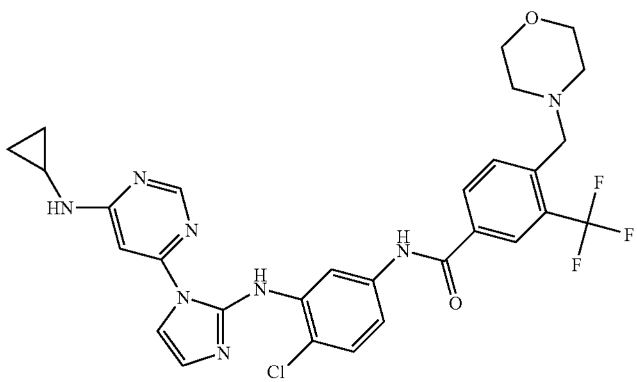 | MS m/z 613.3 (M + 1) |
| 130 | 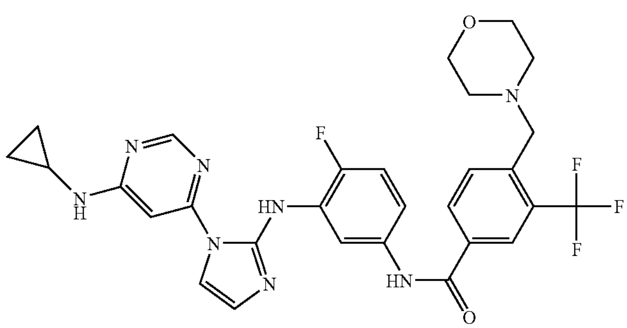 | MS m/z 597.3 (M + 1) |
| 131 | 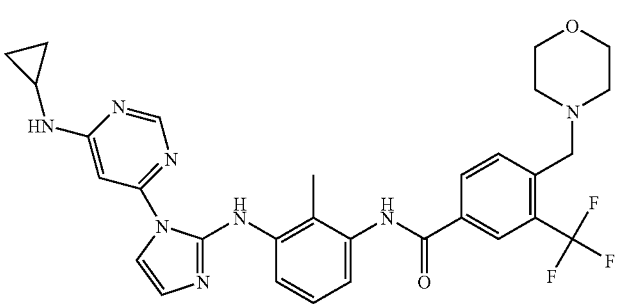 | MS m/z 593.3 (M + 1) |

TABLE 1-continued

| Compound Number | Structure | Physical Data $^1$H NMR 400 MHz (DMSO-$d_6$) and/or MS (m/z) |
|---|---|---|
| 132 | 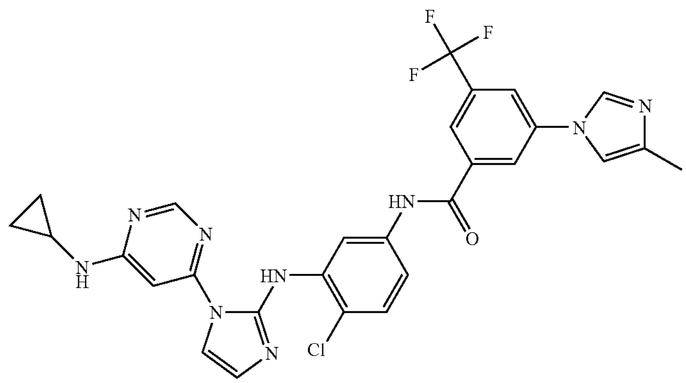 | MS m/z 594.3 (M + 1) |
| 133 | 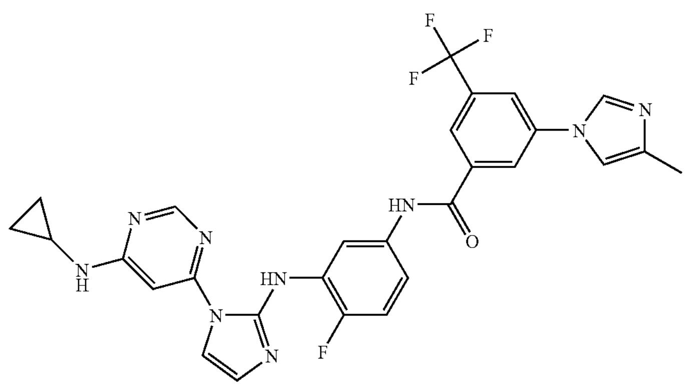 | MS m/z 578.3 (M + 1) |
| 134 | 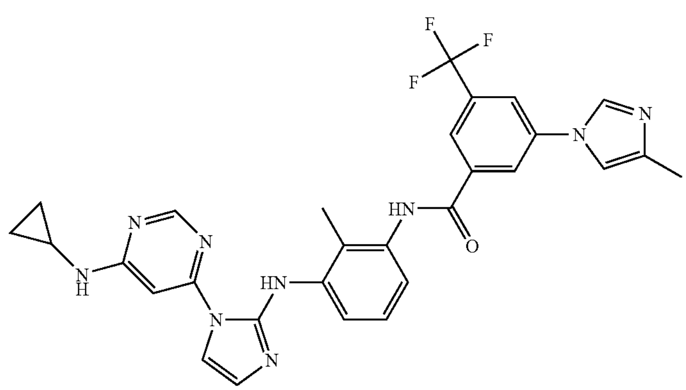 | MS m/z 574.3 (M + 1) |
| 135 | 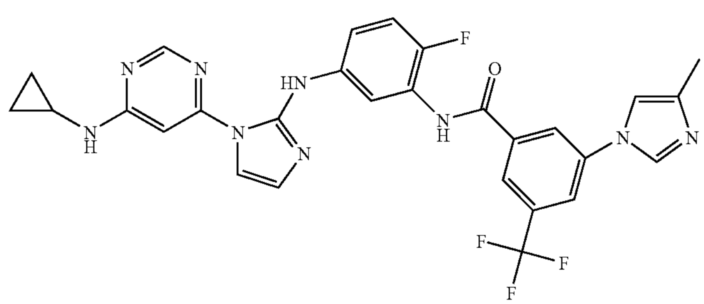 | MS m/z 577.3 (M + 1) |

TABLE 1-continued

| Compound Number | Structure | Physical Data $^1$H NMR 400 MHz (DMSO-$d_6$) and/or MS (m/z) |
|---|---|---|
| 136 | 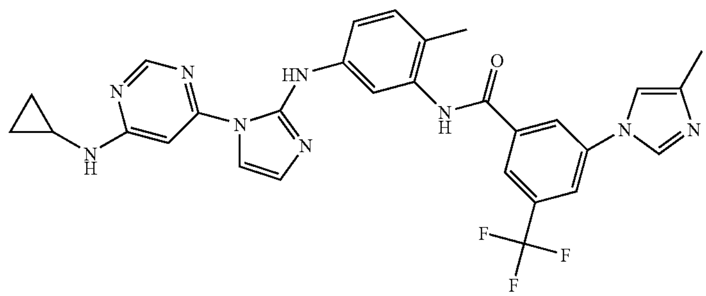 | MS m/z 574.3 (M + 1) |
| 137 | 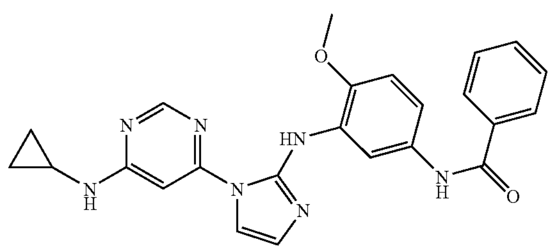 | MS m/z 442.3 (M + 1) |
| 138 | 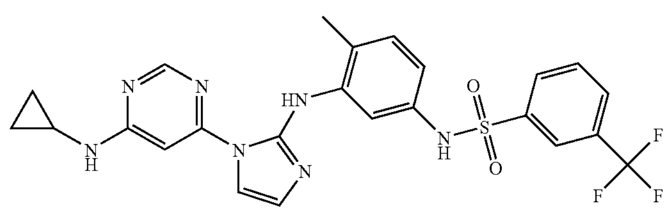 | MS m/z 530.3 (M + 1) |
| 139 | 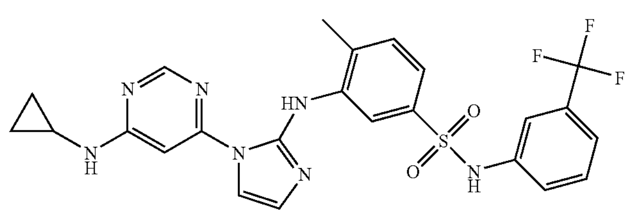 | MS m/z 530.3 (M + 1) |
| 140 | 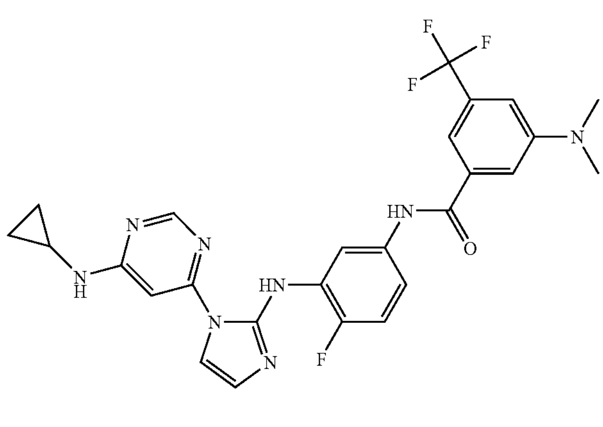 | MS m/z 541.3 (M + 1) |

TABLE 1-continued
| Compound Number | Structure | Physical Data $^1$H NMR 400 MHz (DMSO-$d_6$) and/or MS (m/z) |
|---|---|---|
| 141 | 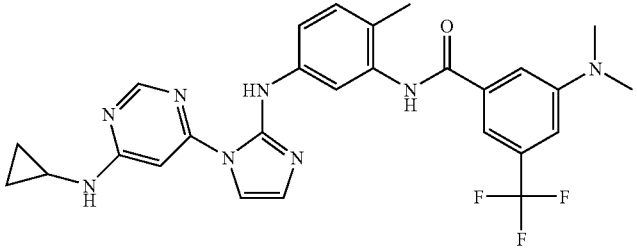 | MS m/z 537.3 (M + 1) |
| 142 | 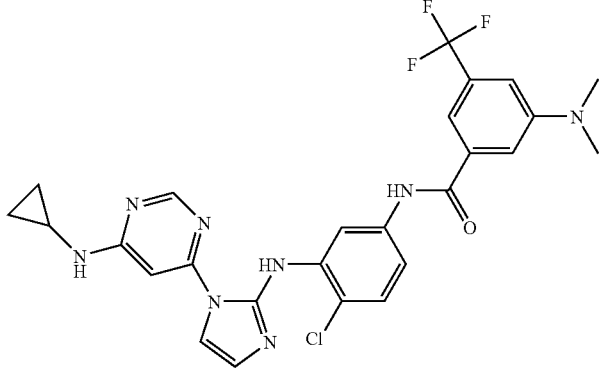 | MS m/z 557.3 (M + 1) |
| 143 | 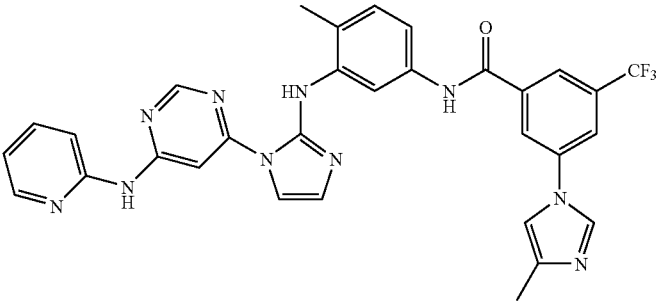 | MS m/z 611.3 (M + 1) |
| 144 | 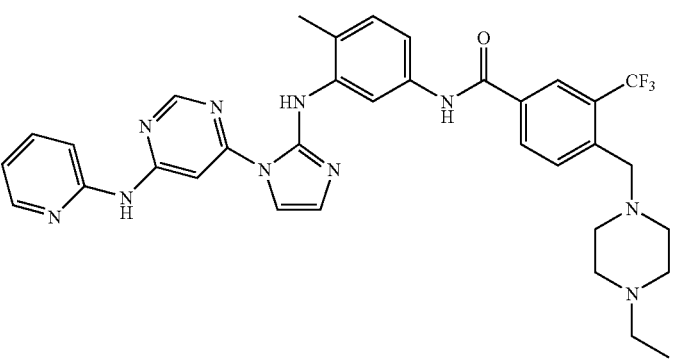 | MS m/z 657.3 (M + 1) |

TABLE 1-continued

| Compound Number | Structure | Physical Data ¹H NMR 400 MHz (DMSO-$d_6$) and/or MS (m/z) |
|---|---|---|
| 145 | 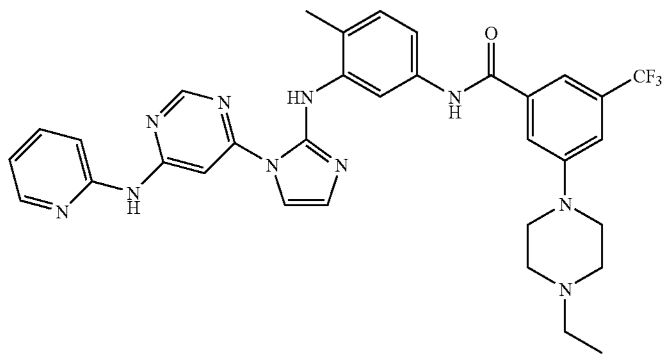 | MS m/z 643.3 (M + 1) |
| 146 | 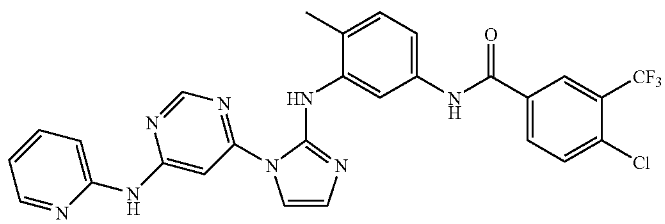 | MS m/z 565.3 (M + 1) |
| 147 | 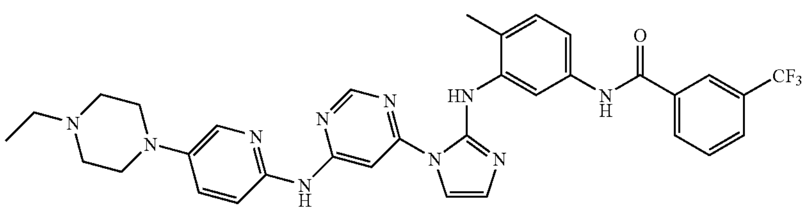 | MS m/z 643.3 (M + 1) |
| 148 | 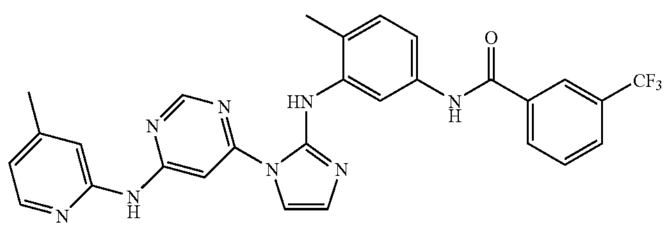 | MS m/z 545.3 (M + 1) |
| 149 | 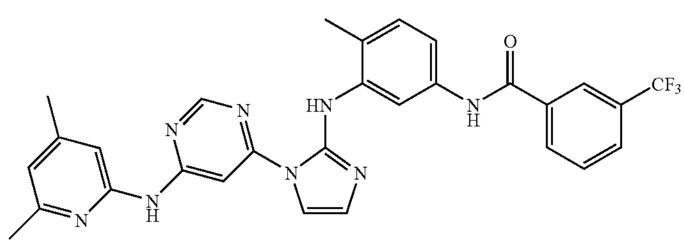 | MS m/z 559.3 (M + 1) |
| 150 | 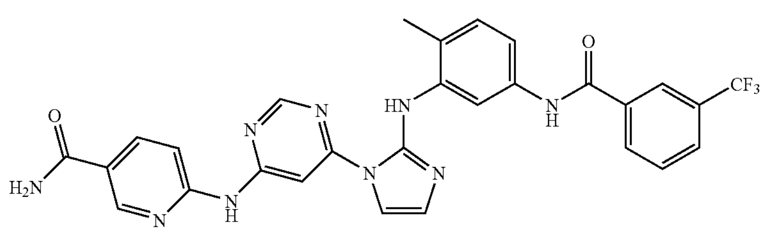 | MS m/z 574.3 (M + 1) |

TABLE 1-continued

| Compound Number | Structure | Physical Data<br>¹H NMR 400 MHz (DMSO-d₆) and/or MS (m/z) |
|---|---|---|
| 151 | 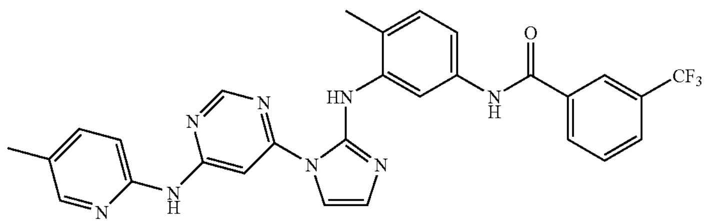 | MS m/z 545.3 (M + 1) |
| 152 | 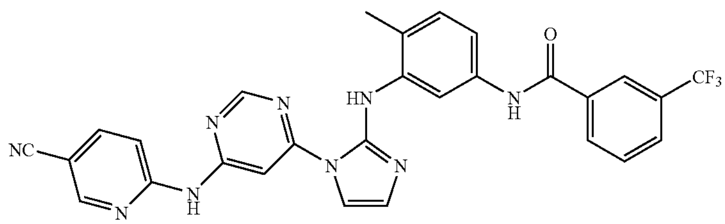 | MS m/z 556.3 (M + 1) |
| 153 | 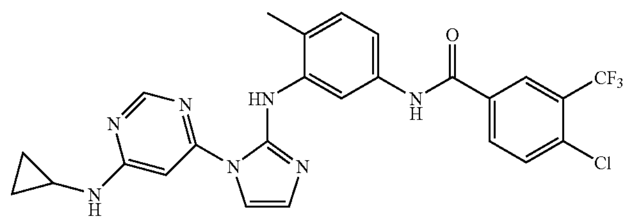 | MS m/z 528.3 (M + 1) |
| 154 | 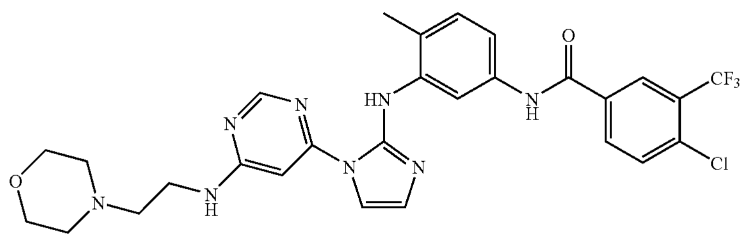 | MS m/z 601.3 (M + 1) |
| 155 | 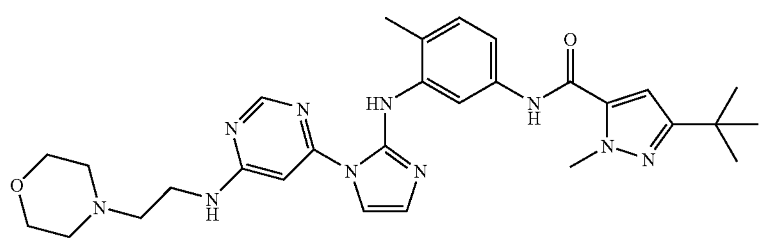 | MS m/z 559.3 (M + 1) |
| 156 | 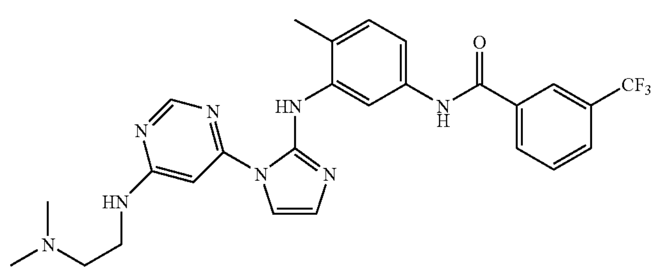 | MS m/z 525.3 (M + 1) |

TABLE 1-continued
| Compound Number | Structure | Physical Data $^1$H NMR 400 MHz (DMSO-$d_6$) and/or MS (m/z) |
|---|---|---|
| 157 | 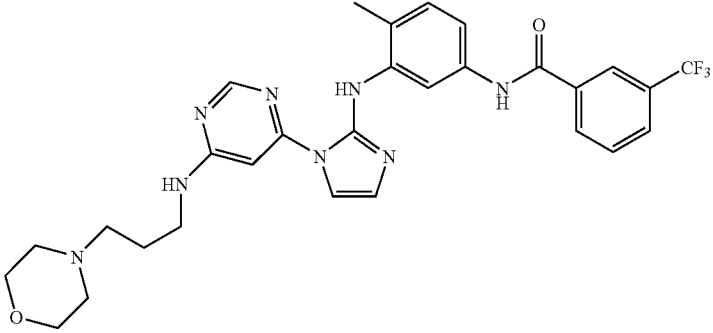 | MS m/z 581.3 (M + 1) |
| 158 | 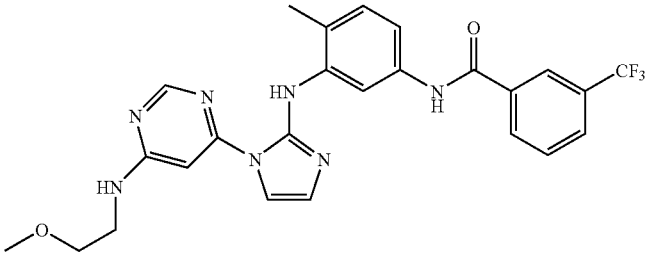 | MS m/z 512.3 (M + 1) |
| 159 | 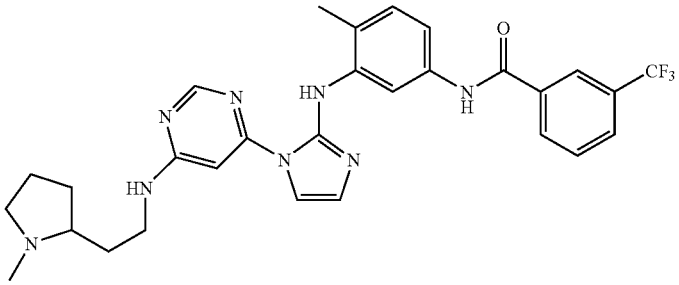 | MS m/z 565.3 (M + 1) |
| 160 | 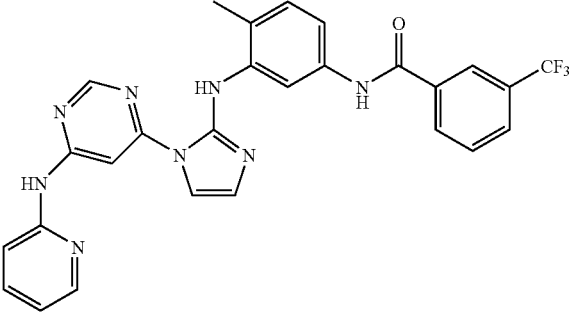 | MS m/z 531.3 (M + 1) |
| 161 | 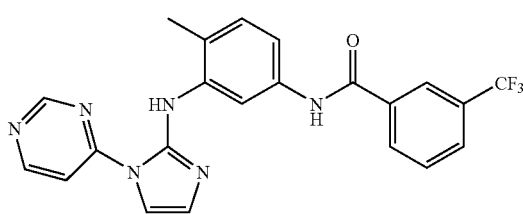 | MS m/z 439.3 (M + 1) |

TABLE 1-continued

| Compound Number | Structure | Physical Data<br>¹H NMR 400 MHz (DMSO-d₆) and/or MS (m/z) |
|---|---|---|
| 162 | 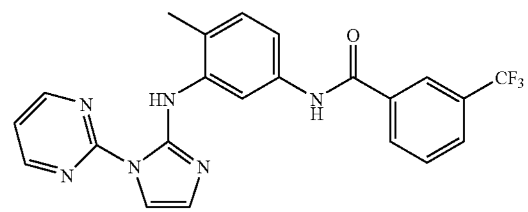 | MS m/z 439.3 (M + 1) |
| 163 | 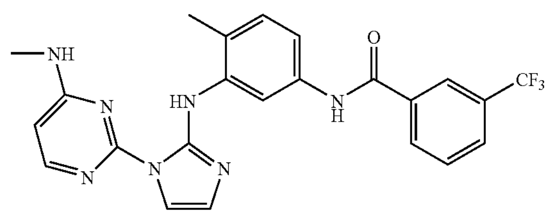 | MS m/z 468.3 (M + 1) |
| 164 | 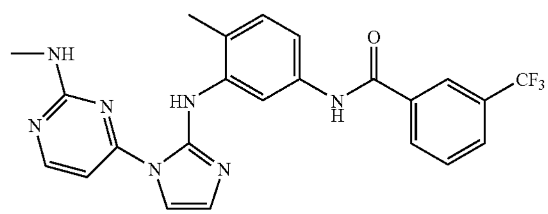 | MS m/z 468.3 (M + 1) |
| 165 | 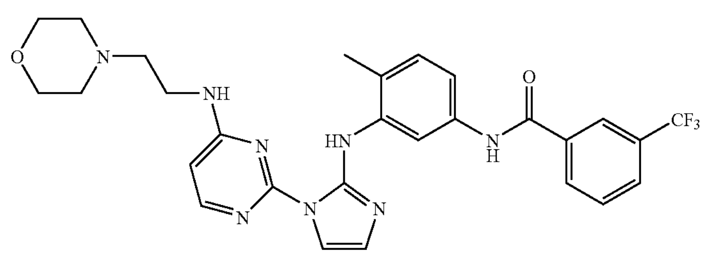 | MS m/z 567.3 (M + 1) |
| 166 | 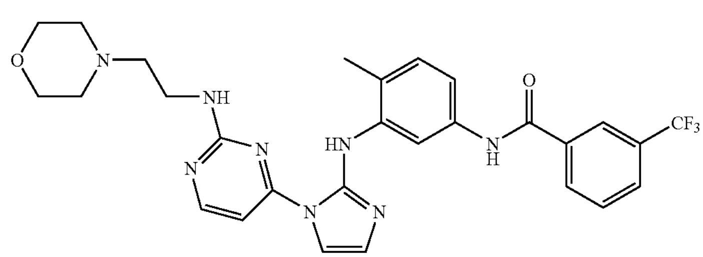 | MS m/z 567.3 (M + 1) |
| 167 | 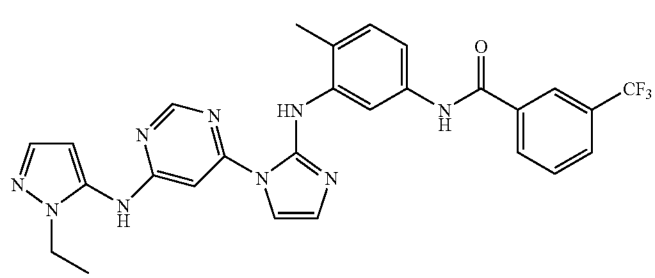 | MS m/z 548.3 (M + 1) |

US 7,745,437 B2
103                                                                                                              104
TABLE 1-continued
| Compound Number | Structure | Physical Data<br>¹H NMR 400 MHz (DMSO-$d_6$) and/or MS (m/z) |
|---|---|---|
| 168 | 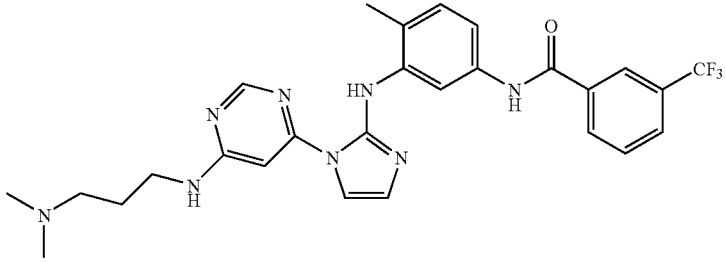 | MS m/z 539.3 (M + 1) |
| 169 | 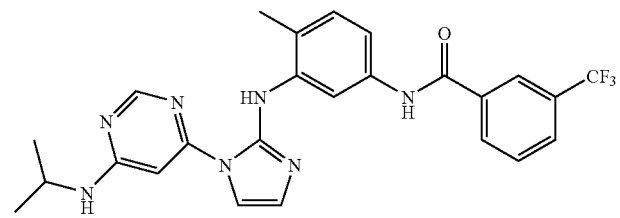 | MS m/z 496.3 (M + 1) |
| 170 | 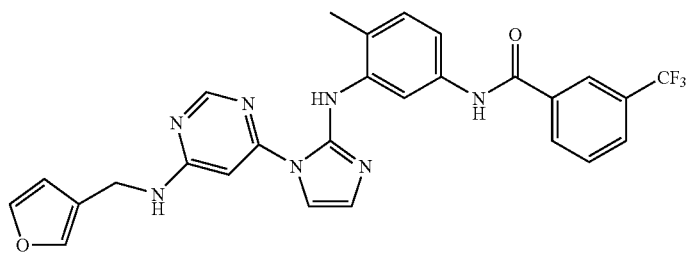 | MS m/z 534.3 (M + 1) |
| 171 | 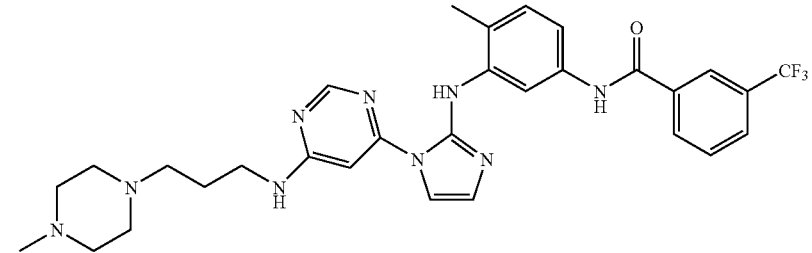 | MS m/z 594.3 (M + 1) |
| 172 | 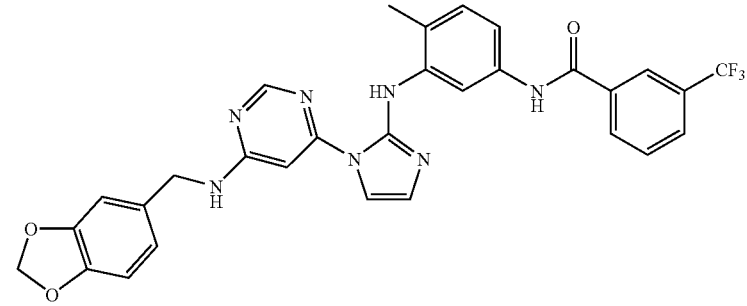 | MS m/z 588.3 (M + 1) |

TABLE 1-continued

| Compound Number | Structure | Physical Data ¹H NMR 400 MHz (DMSO-$d_6$) and/or MS (m/z) |
|---|---|---|
| 173 | 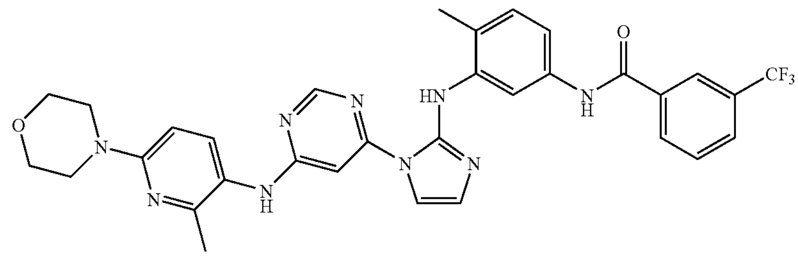 | MS m/z 630.3 (M + 1) |
| 174 | 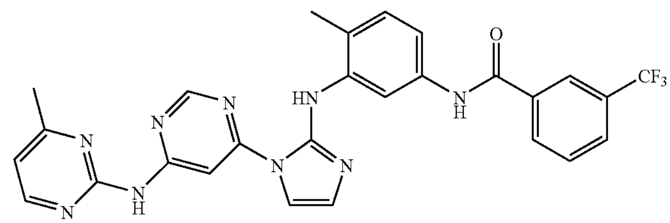 | MS m/z 546.3 (M + 1) |
| 175 | 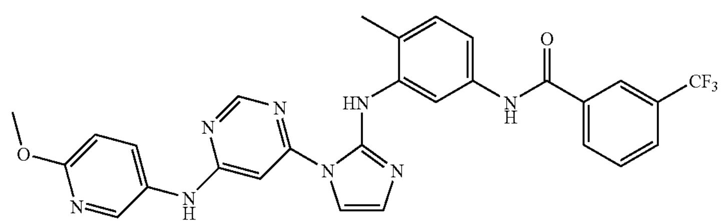 | MS m/z 561.3 (M + 1) |
| 176 | 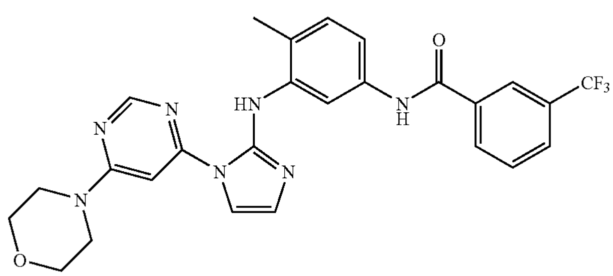 | MS m/z 524.3 (M + 1) |
| 177 | 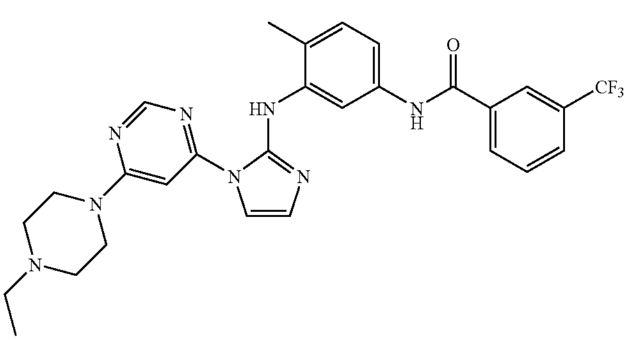 | MS m/z 551.3 (M + 1) |
| 178 | 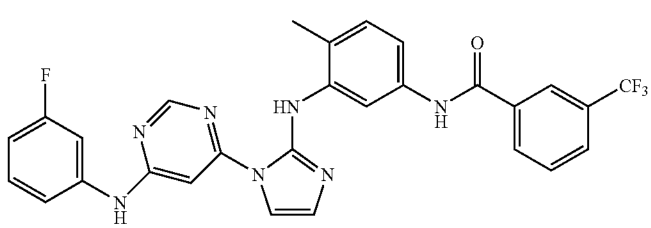 | MS m/z 548.3 (M + 1) |

TABLE 1-continued

| Compound Number | Structure | Physical Data<br>¹H NMR 400 MHz (DMSO-$d_6$) and/or MS (m/z) |
| --- | --- | --- |
| 179 | 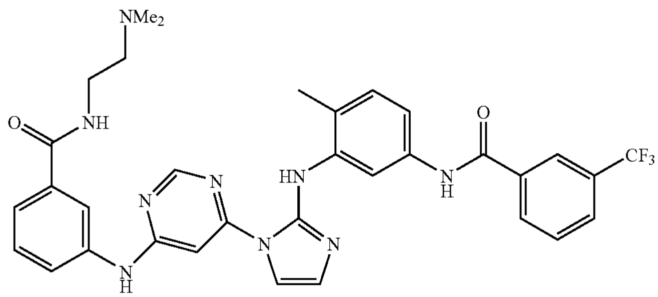 | MS m/z 644.3 (M + 1) |
| 180 | 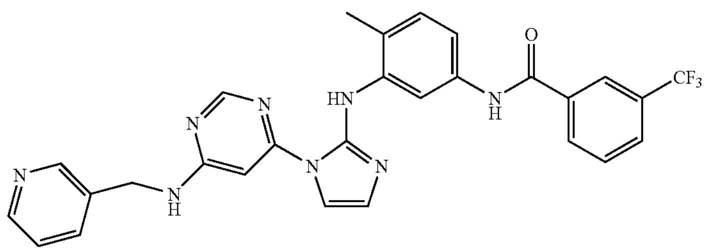 | MS m/z 545.3 (M + 1) |
| 181 | 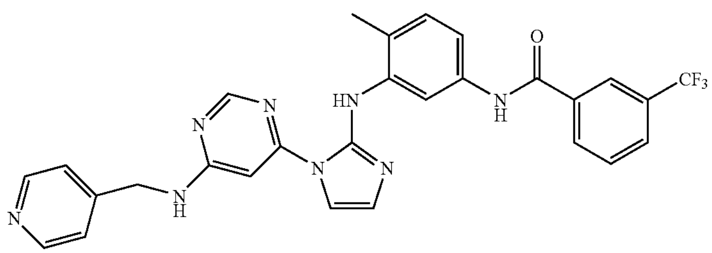 | MS m/z 545.3 (M + 1) |
| 182 | 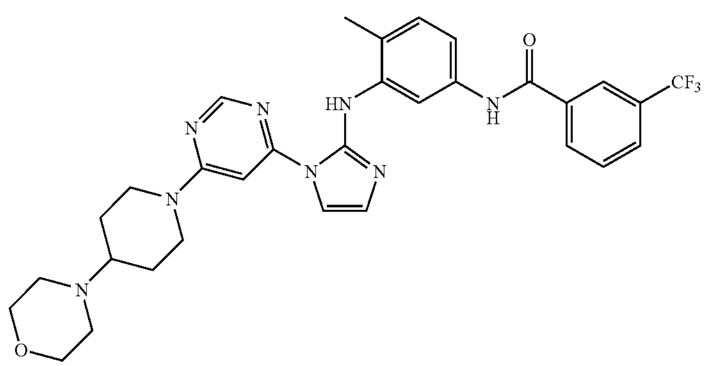 | MS m/z 607.3 (M + 1) |
| 183 | 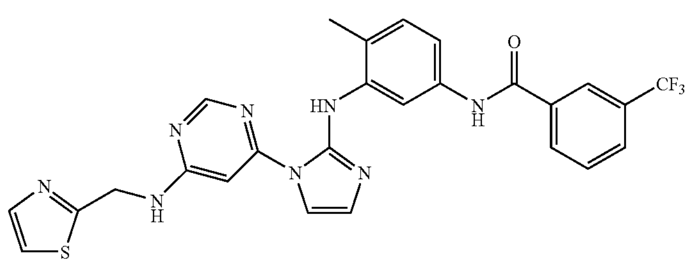 | MS m/z 551.3 (M + 1) |

TABLE 1-continued

| Compound Number | Structure | Physical Data $^1$H NMR 400 MHz (DMSO-$d_6$) and/or MS (m/z) |
| --- | --- | --- |
| 184 | 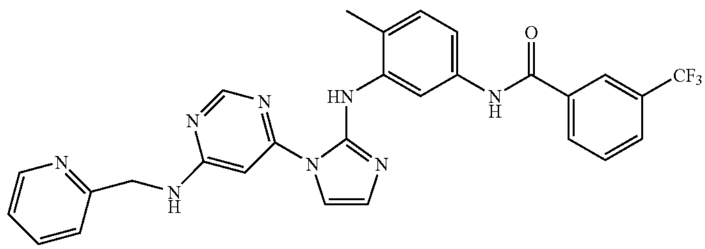 | MS m/z 545.3 (M + 1) |
| 185 | 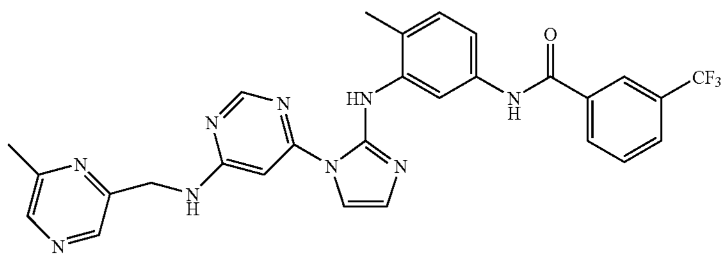 | MS m/z 560.3 (M + 1) |
| 186 | 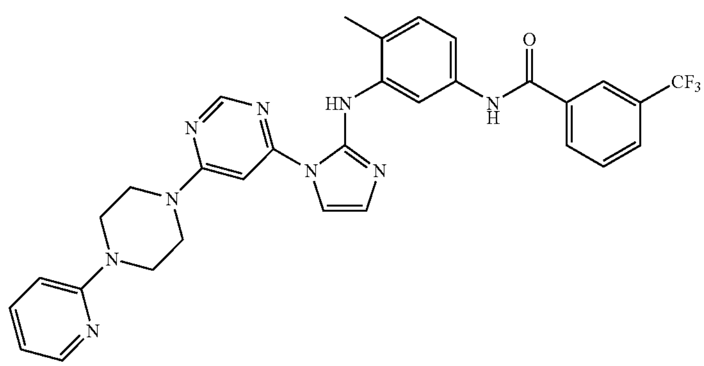 | MS m/z 600.3 (M + 1) |
| 187 | 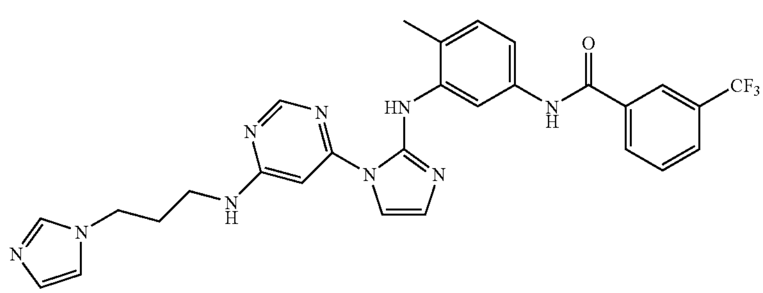 | MS m/z 562.3 (M + 1) |
| 188 | 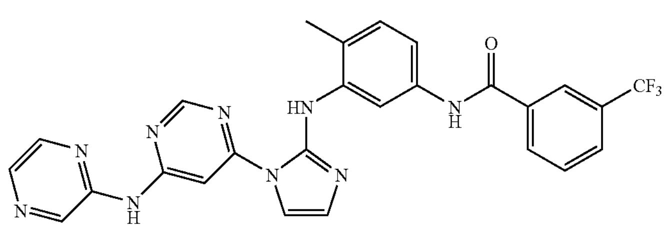 | MS m/z 532.3 (M + 1) |

TABLE 1-continued

| Compound Number | Structure | Physical Data $^1$H NMR 400 MHz (DMSO-$d_6$) and/or MS (m/z) |
|---|---|---|
| 189 | 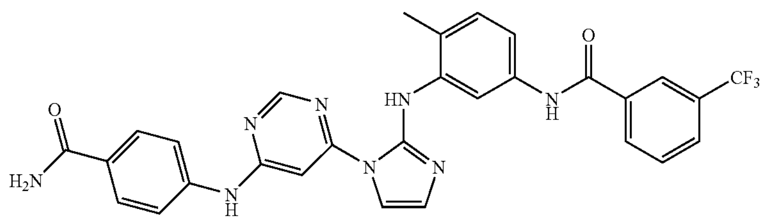 | MS m/z 573.3 (M + 1) |
| 190 | 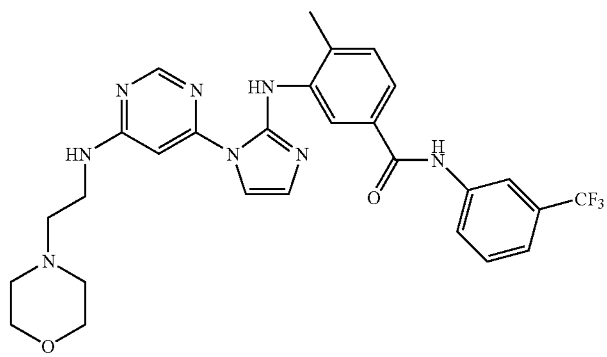 | MS m/z 567.2 (M + 1) |
| 191 | 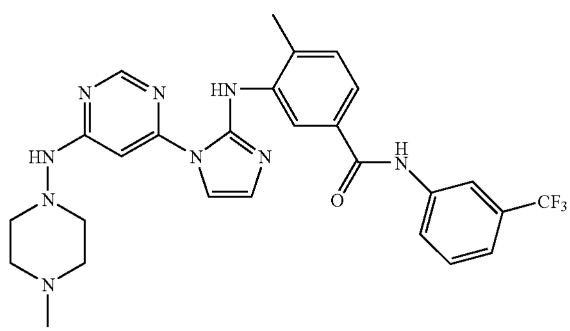 | MS m/z 552.2 (M + 1) |
| 192 | 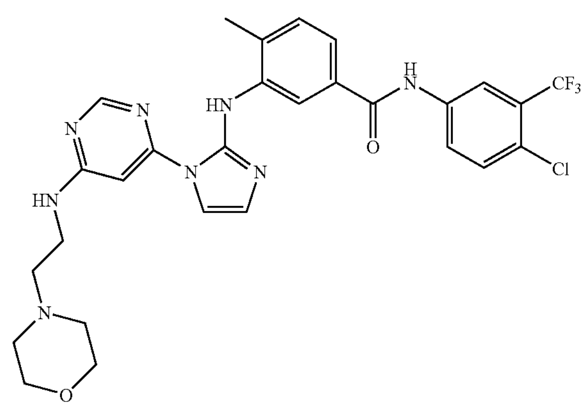 | MS m/z 601.2 (M + 1) |

TABLE 1-continued

| Compound Number | Structure | Physical Data <sup>1</sup>H NMR 400 MHz (DMSO-d<sub>6</sub>) and/or MS (m/z) |
| --- | --- | --- |
| 193 | 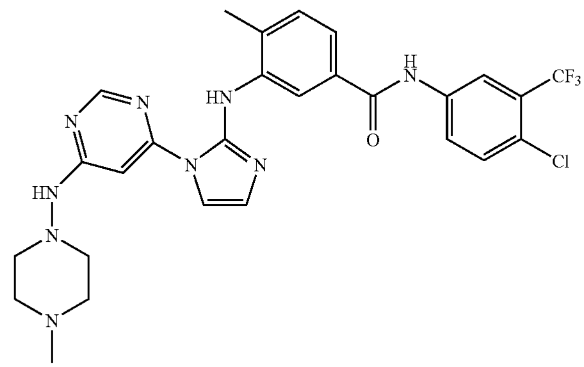 | MS m/z 586.2 (M + 1) |
| 194 | 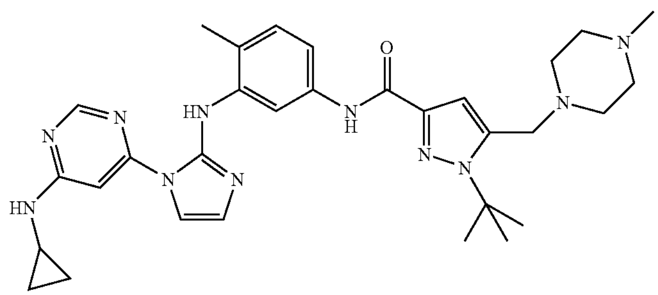 | MS m/z 584.4 (M + 1) |
| 195 | 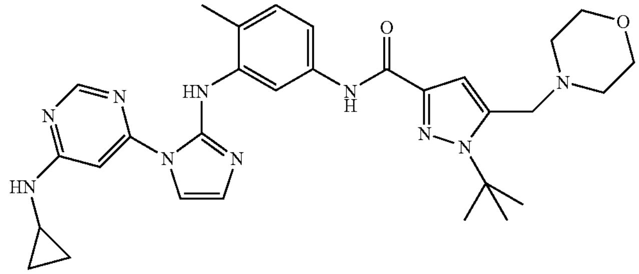 | MS m/z 571.3 (M + 1) |
| 196 | 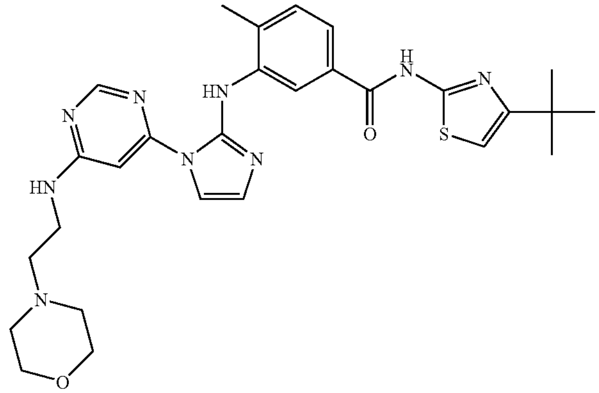 | MS m/z 562.3 (M + 1) |

TABLE 1-continued
| Compound Number | Structure | Physical Data $^1$H NMR 400 MHz (DMSO-$d_6$) and/or MS (m/z) |
|---|---|---|
| 197 | 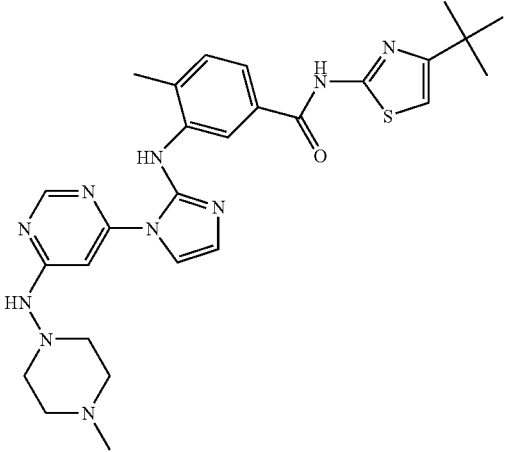 | MS m/z 547.3 (M + 1) |
| 198 | 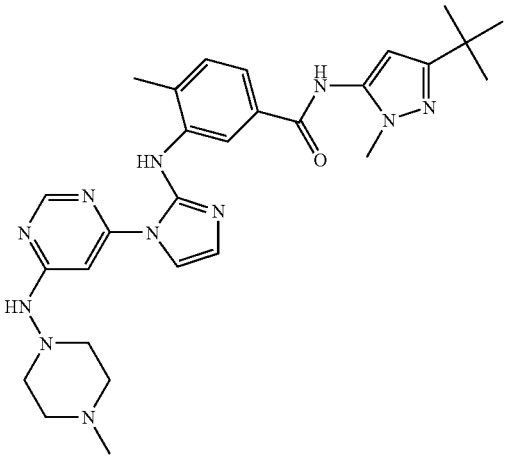 | MS m/z 544.3 (M + 1) |
| 199 | 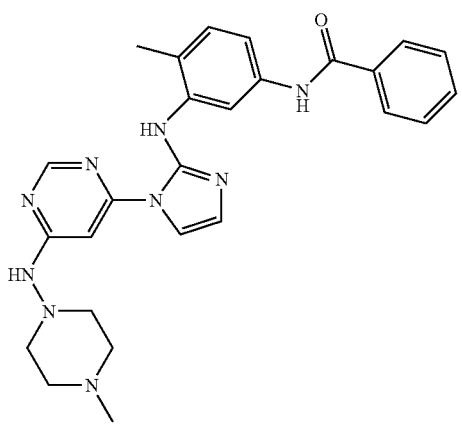 | MS m/z 484.3 (M + 1) |

TABLE 1-continued

| Compound Number | Structure | Physical Data <br> $^1$H NMR 400 MHz (DMSO-$d_6$) and/or MS (m/z) |
|---|---|---|
| 200 | 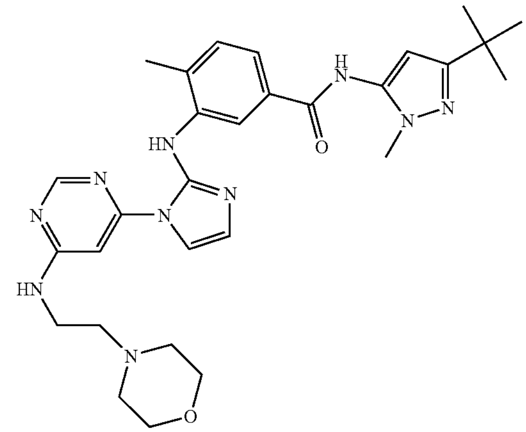 | MS m/z 559.3 (M + 1) |
| 201 | 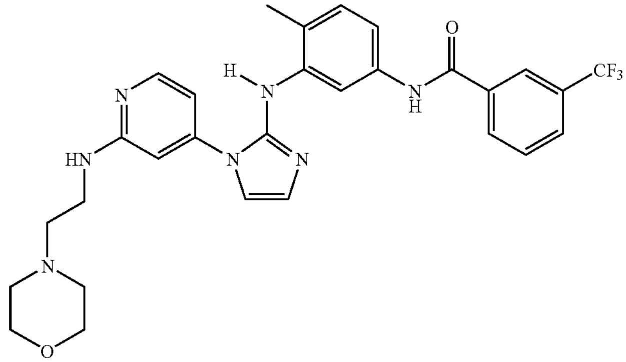 | MS m/z 566.2 (M + 1) |
| 202 | 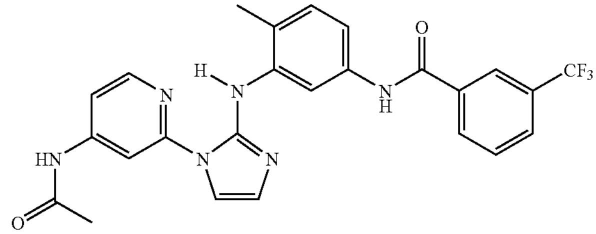 | MS m/z 495.2 (M + 1) |
| 203 | 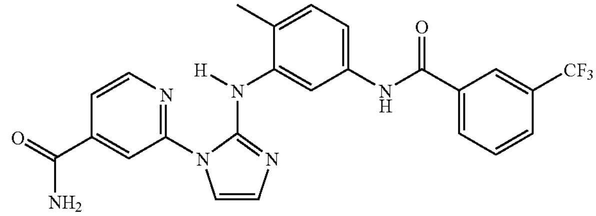 | MS m/z 481.2 (M + 1) |

Assays

Compounds of the present invention are assayed to measure their capacity selectively inhibit cell proliferation of 32D cells expressing BCR-Abl (32D-p210) compared with parental 32D cells. Compounds selectively inhibiting the proliferation of these BCR-Abl transformed cells are tested for antiproliferative activity on Ba/F3 cells expressing either wild type or the mutant forms of Bcr-abl. In addition, compounds are assayed to measure their capacity to inhibit FGFR3, b-RAF, Abl, BMX, BTK, CHK2, c-RAF, CSK, c-SRC, Fes, Flt3, IKKα, IKKβ, JNK2α2, Lck, Met, MKK4, MKK6, MST2, NEK2, p70S6K, PDGFRα, PKA, PKBα, PKD2, Rsk1, SAPK2α, SAPK2β, SAPK3, SGK, Tie2 and trkB kinases.

Inhibition of Cellular BCR-Abl Dependent Proliferation (High Throughput Method)

The murine cell line used is the 32D hemopoietic progenitor cell line transformed with BCR-Abl cDNA (32D-p210). These cells are maintained in RPMI/10% fetal calf serum (RPMI/FCS) supplemented with penicillin 50 μg/mL, streptomycin 50 μg/mL and L-glutamine 200 mM. Untransformed 32D cells are similarly maintained with the addition of 15% of WEHI conditioned medium as a source of IL3.

50 μl of a 32D or 32D-p210 cells suspension are plated in Greiner 384 well microplates (black) at a density of 5000 cells per well. 50 nl of test compound (1 mM in DMSO stock solution) is added to each well (STI571 is included as a positive control). The cells are incubated for 72 hours at 37° C., 5% $CO_2$. 10 μl of a 60% Alamar Blue solution (Tek diagnostics) is added to each well and the cells are incubated for an additional 24 hours. The fluorescence intensity (Excitation at 530 nm, Emission at 580 nm) is quantified using the Acquest™ system (Molecular Devices).

Inhibition of Cellular BCR-Abl Dependent Proliferation 32D-p210 cells are plated into 96 well TC plates at a density of 15,000 cells per well. 50 μL of two fold serial dilutions of the test compound ($C_{max}$ is 40 μM) are added to each well (STI571 is included as a positive control). After incubating the cells for 48 hours at 37° C., 5% $CO_2$, 15 μL of MTT (Promega) is added to each well and the cells are incubated for an additional 5 hours. The optical density at 570 nm is quantified spectrophotometrically and $IC_{50}$ values, the concentration of compound required for 50% inhibition, determined from a dose response curve.

Effect on Cell Cycle Distribution 32D and 32D-p210 cells are plated into 6 well TC plates at 2.5×10⁶ cells per well in 5 ml of medium and test compound at 1 or 10 μM is added (STI571 is included as a control). The cells are then incubated for 24 or 48 hours at 37° C., 5% $CO_2$. 2 ml of cell suspension is washed with PBS, fixed in 70% EtOH for 1 hour and treated with PBS/EDTA/RNase A for 30 minutes. Propidium iodide (Cf=10 μg/ml) is added and the fluorescence intensity is quantified by flow cytometry on the FACScalibur™ system (BD Biosciences). Test compounds of the present invention demonstrate an apoptotic effect on the 32D-p210 cells but do not induce apoptosis in the 32D parental cells.

Effect on Cellular BCR-Abl Autophosphorylation

BCR-Abl autophosphorylation is quantified with capture Elisa using a c-abl specific capture antibody and an antiphosphotyrosine antibody. 32D-p210 cells are plated in 96 well TC plates at 2×10⁵ cells per well in 50 μL of medium. 50 μL of two fold serial dilutions of test compounds ($C_{max}$ is 10 μM) are added to each well (STI571 is included as a positive control). The cells are incubated for 90 minutes at 37° C., 5% $CO_2$. The cells are then treated for 1 hour on ice with 150 μL of lysis buffer (50 mM Tris-HCl, pH 7.4, 150 mM NaCl, 5 mM EDTA, 1 mM EGTA and 1% NP-40) containing protease and phosphatase inhibitors. 50 μL of cell lysate is added to 96 well optiplates previously coated with anti-abl specific antibody and blocked. The plates are incubated for 4 hours at 4° C. After washing with TBS-Tween 20 buffer, 50 μL of alkaline-phosphatase conjugated anti-phosphotyrosine antibody is added and the plate is further incubated overnight at 4° C. After washing with TBS-Tween 20 buffer, 90 μL of a luminescent substrate are added and the luminescence is quantified using the Acquest™ system (Molecular Devices). Test compounds of the invention that inhibit the proliferation of the BCR-Abl expressing cells, inhibit the cellular BCR-Abl autophosphorylation in a dose-dependent manner.

Effect on Proliferation of Cells Expressing Mutant Forms of Bcr-abl

Compounds of the invention are tested for their antiproliferative effect on Ba/F3 cells expressing either wild type or the mutant forms of BCR-Abl (G250E, E255V, T315I, F317L, M351T) that confers resistance or diminished sensitivity to STI571. The antiproliferative effect of these compounds on the mutant-BCR-Abl expressing cells and on the non transformed cells were tested at 10, 3.3, 1.1 and 0.37 μM as described above (in media lacking IL3). The $IC_{50}$ values of the compounds lacking toxicity on the untransformed cells were determined from the dose response curves obtained as describe above.

FGFR3 (Enzymatic Assay)

Kinase activity assay with purified FGFR3 (Upstate) is carried out in a final volume of 10 μL containing 0.25 μg/mL of enzyme in kinase buffer (30 mM Tris-HCl pH7.5, 15 mM $MgCl_2$, 4.5 mM $MnCl_2$, 15 μM $Na_3VO_4$ and 50 μg/mL BSA), and substrates (5 μg/mL biotin-poly-EY (Glu, Tyr) (CIS-US, Inc.) and 3 μM ATP). Two solutions are made: the first solution of 5 μl contains the FGFR3 enzyme in kinase buffer was first dispensed into 384-format ProxiPlate® (Perkin-Elmer) followed by adding 50 nL of compounds dissolved in DMSO, then 5 μl of second solution contains the substrate (poly-EY) and ATP in kinase buffer was added to each wells. The reactions are incubated at room temperature for one hour, stopped by adding 10 μL of HTRF detection mixture, which contains 30 mM Tris-HCl pH7.5, 0.5 M KF, 50 mM ETDA, 0.2 mg/mL BSA, 15 μg/mL streptavidin-XL665 (CIS-US, Inc.) and 150 ng/mL cryptate conjugated anti-phosphotyrosine antibody (CIS-US, Inc.). After one hour of room temperature incubation to allow for streptavidin-biotin interaction, time resolved florescent signals are read on Analyst GT (Molecular Devices Corp.). $IC_{50}$ values are calculated by linear regression analysis of the percentage inhibition of each compound at 12 concentrations (1:3 dilution from 50 μM to 0.28 nM). In this assay, compounds of the invention have an $IC_{50}$ in the range of 10 nM to 2 μM.

FGFR3 (Cellular Assay)

Compounds of the invention are tested for their ability to inhibit transformed Ba/F3-TEL-FGFR3 cells proliferation, which is depended on FGFR3 cellular kinase activity. Ba/F3-TEL-FGFR3 are cultured up to 800,000 cells/mL in suspension, with RPMI 1640 supplemented with 10% fetal bovine serum as the culture medium. Cells are dispensed into 384-well format plate at 5000 cell/well in 50 μL culture medium. Compounds of the invention are dissolved and diluted in dimethylsufoxide (DMSO). Twelve points 1:3 serial dilutions are made into DMSO to create concentrations gradient ranging typically from 10 mM to 0.05 μM. Cells are added with 50 nL of diluted compounds and incubated for 48 hours in cell culture incubator. AlamarBlue® (TREK Diagnostic Systems), which can be used to monitor the reducing environment created by proliferating cells, are added to cells at final concentration of 10%. After additional four hours of incubation in a 37° C. cell culture incubator, fluorescence signals from reduced AlamarBlue® (Excitation at 530 nm, Emission at 580 nm) are quantified on Analyst GT (Molecular Devices Corp.). $IC_{50}$ values are calculated by linear regression analysis of the percentage inhibition of each compound at 12 concentrations.

FLT3 and PDGFRβ (Cellular Assay)

The effects of compounds of the invention on the cellular activity of FLT3 and PDGFRβ are conducted using identical methods as described above for FGFR3 cellular activity, except that instead of using Ba/F3-TEL-FGFR3, Ba/F3-FLT3-ITD and Ba/F3-Tel-PDGFRβ are used, respectively.

b-Raf—Enzymatic Assay

Compounds of the invention are tested for their ability to inhibit the activity of b-Raf. The assay is carried out in 384-well MaxiSorp plates (NUNC) with black walls and clear bottom. The substrate, IκBα is diluted in DPBS (1:750) and 15 μl is added to each well. The plates are incubated at 4° C. overnight and washed 3 times with TBST (25 mM Tris, pH 8.0, 150 mM NaCl and 0.05% Tween-20) using the EMBLA plate washer. Plates are blocked by Superblock (15 μl/well) for 3 hours at room temperature, washed 3 times with TBST and pat-dried. Assay buffer containing 20 μM ATP (10 μl) is added to each well followed by 100 nl or 500 nl of compound. B-Raf is diluted in the assay buffer (1 μl into 25 μl) and 10 μl of diluted b-Raf is added to each well (0.4 μg/well). The plates are incubated at room temperature for 2.5 hours. The kinase reaction is stopped by washing the plates 6 times with TBST. Phosph-IκBα (Ser32/36) antibody is diluted in Superblock (1:10,000) and 15 μl is added to each well. The plates are incubated at 4° C. overnight and washed 6 times with TBST. AP-conjugated goat-anti-mouse IgG is diluted in Superblock (1:1,500) and 15 μl is added to each well. Plates are incubated at room temperature for 1 hour and washed 6 times with TBST. 15 μl of fluorescent Attophos AP substrate (Promega) is added to each well and plates are incubated at room temperature for 15 minutes. Plates are read on Acquest or Analyst GT using a Fluorescence Intensity Program (Excitation 455 nm, Emission 580 nm).

b-Raf—Cellular Assay

Compounds of the invention are tested in A375 cells for their ability to inhibit phosphorylation of MEK. A375 cell line (ATCC) is derived from a human melanoma patient and it has a V599E mutation on the B-Raf gene. The levels of phosphorylated MEK are elevated due to the mutation of B-Raf. Sub-confluent to confluent A375 cells are incubated with compounds for 2 hours at 37° C. in serum free medium. Cells are then washed once with cold PBS and lysed with the lysis buffer containing 1% Triton X100. After centrifugation, the supernatants are subjected to SDS-PAGE, and then transferred to nitrocellulose membranes. The membranes are then subjected to western blotting with anti-phospho-MEK antibody (ser217/221) (Cell Signaling). The amount of phosphorylated MEK is monitored by the density of phospho-MEK bands on the nitrocellulose membranes.

Upstate KinaseProfiler™—Radio-Enzymatic Filter Binding Assay

Compounds of the invention are assessed for their ability to inhibit individual members of the kinase panel. The compounds are tested in duplicates at a final concentration of 10 μM following this generic protocol. Note that the kinase buffer composition and the substrates vary for the different kinases included in the "Upstate KinaseProfiler™" panel. Kinase buffer (2.5 μL, 10×—containing MnCl$_2$ when required), active kinase (0.001-0.01 Units; 2.5 μL), specific or Poly(Glu4-Tyr) peptide (5-500 μM or 0.01 mg/ml) in kinase buffer and kinase buffer (50 μM; 5 μL) are mixed in an eppendorf on ice, A Mg/ATP mix (10 μL; 67.5 (or 33.75) mM MgCl$_2$, 450 (or 225) μM ATP and 1 μCi/μl [γ-$^{32}$P]-ATP (3000 Ci/mmol)) is added and the reaction is incubated at about 30° C. for about 10 minutes. The reaction mixture is spotted (20 μL) onto a 2 cm×2 cm P81 (phosphocellulose, for positively charged peptide substrates) or Whatman No. 1 (for Poly (Glu4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction.

Compounds of Formula I, in free form or in pharmaceutically acceptable salt form, exhibit valuable pharmacological properties, for example, as indicated by the in vitro tests described in this application. For example, compounds of Formula I preferably show an IC$_{50}$ in the range of $1\times10^{-10}$ to $1\times10^5$ M, preferably less than 50 nM for wild type BCR-Abl and G250E, E255V, T315I, F317L and M351T BCR-Abl mutants. Compounds of Formula I preferably, at a concentration of 10 mM, preferably show a percentage inhibition of greater than 50%, preferably greater than about 70%, against Abl, Bcr-abl, c-RAF, c-SRC, JNK2α2, lck, MKK6, PDGFRα, SAPK2α, SAPK2β, Tie2 and TrkB kinases. For example:

a). N-{3-[1-(6-cyclopropylamino-pyrimidin-4-yl)-1H-imidazol-2-ylamino]-4-methyl-phenyl}-3-(4-methyl-imidazol-1-yl)-5-trifluoromethyl-benzamide (Compound 27) has an IC$_{50}$ of <0.5 nM, 20 nM, 36 nM, 59 nM <0.5 nM and <0.5 nM for wild type, G250E, E255V, T315I, F317L and M351T Bcr-abl, respectively;

b). N-{3-[1-(6-Cyclopropylamino-pyrimidin-4-yl)-1H-imidazol-2-ylamino]-4-methyl-phenyl}-4-(4-ethyl-piperazin-1-ylmethyl)-3-trifluoromethyl-benzamide (Compound 25) has an IC50 of 130 nM and 34 nM for the FGFR3 enzyme and cellular assays, respectively, and 149 nM and 2 nM for FLT3 and PDGFRβ, respectively;

c). N-{3-[1-(6-Cyclopropylamino-pyrimidin-4-yl)-1H-imidazol-2-ylamino]-4-methyl-phenyl}-4-(4-methyl-piperazin-1-ylmethyl)-3-trifluoromethyl-benzamide (Compound 26) has an IC50 of 65 nM and 37 nM for the FGFR3 enzyme and cellular assays, respectively, and 89 nM and 2 nM for FLT3 and PDGFRβ, respectively;

d). N-(4-Methyl-3-{1-[6-(2-morpholin-4-yl-ethylamino)-pyrimidin-4-yl]-1H-imidazol-2-ylamino}-phenyl)-3-trifluoromethyl-benzamide (Compound 3), at a concentration of 10 μM, inhibits the following kinases by the percentage shown in brackets (for example, 100% means complete inhibition, 0% means no inhibition): wild-type Abl (97%), c-RAF (100%), c-SRC (99%), JNK2α2, (97%), lck (100%), MKK6 (100%), PDGFRα (97%), SAPK2α (100%), SAPK2β (100%), Tie2 (99%) and TrkB (97%).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of Formula I:

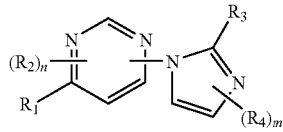

in which:

m and n are independently selected from 0, 1 and 2;

$R_1$ is selected from —$XNR_5R_6$, —$XOR_5$, —$XC(O)R_5$, —$XR_5$ and —$XS(O)_{0-2}R_5$; wherein X is a bond or $C_{1-4}$alkylene optionally substituted by 1 to 2 $C_{1-6}$alkyl radicals; $R_5$ is selected from hydrogen, $C_{1-6}$alkyl, $C_{1-10}$aryl-$C_{0-4}$alkyl, $C_{5-10}$heteroaryl-$C_{0-4}$alkyl, $C_{3-10}$cycloalkyl-$C_{0-4}$alkyl and $C_{3-10}$heterocycloalkyl-$C_{0-4}$alkyl; and $R_6$ is selected from hydrogen and $C_{1-6}$alkyl; or $R_5$ and $R_6$ together with the nitrogen to which $R_5$ and $R_6$ are both attached form heteroaryl or heterocycloalkyl; wherein any aryl, heteroaryl, cycloalkyl and heterocycloalkyl of $R_5$ or the combination of $R_5$ and $R_6$ can be optionally substituted with 1 to 3 radicals independently selected from halo, nitro, cyano, hydroxy, $C_{1-6}$alkyl, $C_{1-6}$alkoxy, halo-substituted-alkyl, halo-substituted-alkoxy, —$XNR_7R_8$, —$XOR_7$, —$XNR_7S(O)_2R_8$, —$XNR_7S(O)R_8$, —$XNR_7SR_8$, —$XC(O)NR_7R_8$, —$XC(O)NR_7XNR_7R_8$, —$XNR_7C(O)NR_7R_8$, —$XNR_7XNR_7R_8$, —$XNR_7XOR_7$, —$XNR_7C(=NR_7)NR_7R_8$, —$XS(O)_2R_9$, —$XNR_7C(O)R_8$, —$XNR_7C(O)R_9$, —$XR_9$, —$XC(O)OR_8$, —$XS(O)_2NR_7R_8$, —$XS(O)NR_7R_8$ and —$XSNR_7R_8$; wherein X is a bond or $C_{1-4}$alkylene; $R_7$ and $R_8$ are independently selected from the group consisting of hydrogen and $C_{1-4}$alkyl; and $R_9$ is selected from $C_{3-10}$heterocycloalkyl and $C_{5-10}$heteroaryl; wherein said heterocycloalkyl or heteroaryl of $R_9$ is optionally substituted with a radical selected from the group consisting of $C_{1-4}$alkyl, —$XNR_7XNR_7R_7$, $XNR_7XOR_7$ and —$XOR_7$;

$R_2$ and $R_4$ are independently selected from halo, hydroxy, $C_{1-4}$alkyl, $C_{1-4}$alkoxy, halo-substituted-$C_{1-4}$alkyl and halo-substituted-$C_{1-4}$alkoxy;

$R_3$ is selected from —$NR_{10}R_{11}$, —$NR_{10}C(O)R_{11}$, —$NR_{10}S(O)_{0-2}R_{11}$ and —$NR_{10}C(O)NR_{10}R_{11}$; wherein $R_{10}$ is selected from hydrogen and $C_{1-6}$alkyl; $R_{11}$ is selected from $C_{6-10}$aryl, $C_{5-10}$heteroaryl, $C_{3-10}$cycloalkyl and $C_{3-10}$heterocycloalkyl; wherein any aryl, heteroaryl, cycloalkyl or heterocycloalkyl of $R_{11}$ is optionally substituted by 1 to 3 radicals selected from halo, nitro, cyano, hydroxy, $C_{1-6}$alkyl, $C_{1-6}$alkoxy, halo-substituted-alkyl, halo-substituted-alkoxy, —$NR_{12}C(O)R_{13}$, —$NR_{12}C(O)NR_{12}R_{13}$, —$C(O)NR_{12}R_{13}$, —$NR_{12}S(O)_{0-2}R_{13}$ and —$S(O)_{0-2}NR_{12}R_{13}$; wherein $R_{12}$ is selected from hydrogen and $C_{1-6}$alkyl; $R_{13}$ is selected from $C_{6-10}$aryl, $C_{5-10}$heteroaryl, $C_{3-10}$cycloalkyl and $C_{3-10}$heterocycloalkyl; wherein any aryl, heteroaryl, cycloalkyl or heterocycloalkyl of $R_{13}$ is optionally substituted with 1 to 3 radicals independently selected from halo, $C_{1-6}$alkyl, halo-substituted-$C_{1-6}$alkyl, $C_{1-6}$alkoxy, halo-substituted-$C_{1-6}$alkoxy, —$XNR_7R_8$, $C_{6-10}$aryl-$C_{0-4}$alkyl, $C_{5-10}$heteroaryl-$C_{0-4}$alkyl, $C_{3-10}$cycloalkyl-$C_{0-4}$alkyl, $C_{3-10}$heterocycloalkyl-$C_{0-4}$alkyl and $C_{3-10}$heterocycloalkyl-$C_{0-4}$alkyl; wherein X, $R_7$ and $R_8$ are as described above and wherein any aryl, heteroaryl, cycloalkyl or heterocycloalkyl substituent of $R_{13}$ is further optionally substituted by 1 to 3 radicals independently selected from halo, $C_{1-6}$alkyl, halo-substituted-$C_{1-6}$alkyl, hydroxy-substituted-$C_{1-6}$alkyl, $C_{1-6}$alkoxy, $C_{3-10}$heterocycloalkyl and halo-substituted-$C_{1-6}$alkoxy; and the pharmaceutically acceptable salts and stereoisomers thereof.

2. The compound of claim 1 of Formula Ia:

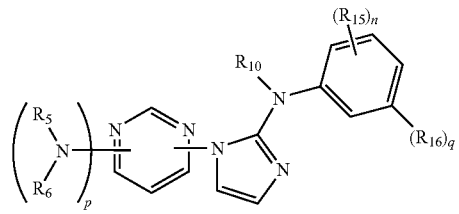

in which:

p is selected from 0 and 1;

n is selected from 0, 1, 2 and 3;

q is selected from 0 and 1;

$R_5$ is selected from hydrogen, $C_{1-6}$alkyl, $C_{6-10}$aryl-$C_{0-4}$alkyl, $C_{5-10}$heteroaryl-$C_{0-4}$alkyl, $C_{3-10}$cycloalkyl-$C_{0-4}$alkyl and $C_{3-10}$heterocycloalkyl-$C_{0-4}$alkyl; and $R_6$ is selected from hydrogen and $C_{1-6}$alkyl; or $R_5$ and $R_6$ together with the nitrogen to which $R_5$ and $R_6$ are both attached form heteroaryl or heterocycloalkyl;

wherein any aryl, heteroaryl, cycloalkyl and heterocycloalkyl of $R_5$ or the combination of $R_5$ and $R_6$ can be optionally substituted with 1 to 3 radicals independently selected from halo, nitro, cyano, hydroxy, $C_{1-6}$alkyl, $C_{1-6}$alkoxy, halo-substituted-alkyl, halo-substituted-alkoxy, —$XNR_7R_8$, —$XOR_7$, —$XNR_7S(O)_2R_8$, —$XNR_7S(O)R_8$, —$XNR_7SR_8$, —$XC(O)NR_7R_8$, —$XC(O)NR_7XNR_7R_8$, —$XNR_7C(O)NR_7R_8$, —$XNR_7XNR_7R_8$, —$XNR_7XOR_7$, —$XNR_7C(=NR_7)NR_7R_8$, —$XS(O)_2R_9$, —$XNR_7C(O)R_8$, —$XNR_7C(O)R_9$, —$XR_9$, —$XC(O)OR_8$, —$XS(O)_2NR_7R_8$, —$XS(O)NR_7R_8$ and —$XSNR_7R_8$; wherein X is a bond or $C_{1-4}$alkylene; $R_7$ and $R_8$ are independently selected from the group consisting of hydrogen and $C_{1-4}$alkyl; and $R_9$ is selected from $C_{3-10}$heterocycloalkyl and $C_{5-10}$heteroaryl; wherein said heterocycloalkyl or heteroaryl of $R_9$ is optionally substituted with a radical selected from the group consisting of $C_{1-4}$alkyl, —$XNR_7XNR_7R_7$, $XNR_7XOR_7$ and —$XOR_7$; wherein X and $R_7$ are as described above;

$R_{10}$ is selected from hydrogen and $C_{1-6}$alkyl;

$R_{15}$ is selected from halo, nitro, cyano, hydroxy, $C_{1-6}$alkyl, $C_{1-6}$alkoxy, halo-substituted-alkyl and halo-substituted-alkoxy; and $R_{16}$ is selected from —$NR_{12}C(O)R_{13}$, —$NR_{12}C(O)NR_{12}R_{13}$, —$C(O)NR_{12}R_{13}$, —$NR_{12}S(O)_{0-2}R_{13}$ and —$S(O)_{0-2}NR_{12}R_{13}$; wherein $R_{12}$ is selected from hydrogen and $C_{1-6}$alkyl; $R_{13}$ is selected from $C_{6-10}$aryl, $C_{5-10}$heteroaryl, $C_{3-10}$cycloalkyl and $C_{3-10}$heterocycloalkyl; wherein any aryl, heteroaryl, cycloalkyl or heterocycloalkyl of $R_{13}$ is optionally substituted with 1 to 3 radicals independently selected from halo, $C_{1-6}$alkyl, halo-substituted-$C_{1-6}$alkyl, $C_{1-6}$alkoxy, halo-substituted-$C_{1-6}$alkoxy, —$XNR_7R_8$, $C_{1-10}$aryl-$C_{0-4}$alkyl, $C_{5-10}$heteroaryl-$C_{0-4}$alkyl, $C_{3-10}$cycloalkyl-$C_{0-4}$alkyl, $C_{3-10}$heterocycloalkyl-$C_{0-4}$alkoxy and $C_{3-10}$heterocycloalkyl-$C_{0-4}$alkyl; wherein X, $R_7$ and $R_8$ are as described above and wherein any aryl, heteroaryl, cycloalkyl or heterocycloalkyl substituent of $R_{13}$ is further optionally substituted by 1 to 3 radicals independently selected from halo, $C_{1-6}$alkyl, halo-substituted-$C_{1-6}$alkyl, hydroxy-substituted-$C_{1-6}$alkyl, $C_{1-6}$alkoxy, $C_{3-10}$heterocycloalkyl and halo-substituted-$C_{1-6}$alkoxy.

3. The compound of claim 2 in which $R_5$ is selected from hydrogen, morpholino-ethyl, cyclopropyl, methyl, 3-(2-oxo-pyrrolidin-1-yl)-propyl, benzo[1,3]dioxol-5-yl, 3-(4-methyl-piperazin-1-yl)-propyl, hydroxymethyl-phenyl, (1-hydroxy-ethyl)-phenyl, morpholino, pyridinyl, methyl-carbonyl, methyl-sulfonyl, methyl-pyridinyl, amino-cyclohexyl, piperidinyl, methyl-piperazinyl-ethyl, dimethyl-pyrazolyl, methyl-pyrazolyl, dimethyl-pyridinyl, methyl-pyridinyl, ethyl-piperazinyl-pyridinyl, amino-carbonyl-pyridinyl, cyano-pyridinyl, dimethyl-amino-ethyl, methoxy-ethyl, methyl-pyrrolidinyl-ethyl, ethyl-pyrazolyl, dimethyl-amino-propyl, isopropyl, furanyl-methyl, methyl-piperazinyl-propyl, benzo[1,3]dioxol-5-ylmethyl, 2-methyl-6-morpholin-4-yl-pyridin-3-yl, methyl-pyrimidinyl, methoxy-pyridinyl, fluoro-phenyl, dimethyl-amino-ethyl-aminocarbonyl, pyridinyl-methyl, thiazolyl-methyl, methyl-pyrazinyl-methyl, imidazolyl-propyl, amino-carbonyl-phenyl, or $R_5$ and $R_6$ together with the nitrogen atom to which they are both attached form a group selected from morpholino, piperidinyl and piperazinyl optionally substituted with a group selected from ethyl, pyridinyl and morpholino.

4. The compound of claim 3 in which $R_{16}$ is selected from —NHC(O)$R_{13}$, —NHC(O)NH$R_{13}$, —C(O)NH$R_{13}$, —NHS(O)$_2R_{13}$ and —S(O)$_2$NH$R_{13}$; wherein $R_{13}$ is selected from phenyl, pyridazinyl, pyridinyl, furanyl, pyrrolyl, imidazolyl, pyrazolyl, quinoxalinyl, thienyl and thiazolyl; wherein $R_{13}$ is optionally substituted with 1 to 3 radicals independently selected from methyl, t-butyl, halo, trifluoromethyl, diethyl-amino, dimethyl-amino, benzyl, piperidinyl-amino, pyrrolidinyl-methoxy, ethyl-piperazinyl-methyl, morpholino, methyl-piperazinyl, methyl-piperazinyl-methyl, ethyl-piperazinyl, methyl-imidazolyl, morpholino-methyl, pyrrolidinyl-piperidinyl, piperazinyl-methyl, hydroxy-piperidinyl, 1-methyl-piperidin-4-yloxy, piperidinyl-oxy, methyl-pyrazinyl, pyrazinyl and hydroxyethyl-piperazinyl.

5. The compound of claim 1 selected from N-[4-methyl-3-(1-{6-[4-(2-morpholin-4-yl-ethyl)-phenylamino]-pyrimidin-4-yl}-1H-imidazol-2-ylamino)-phenyl]-3-trifluoromethyl-benzamide, N-{3-[1-(6-cyclopropylamino-pyrimidin-4-yl)-1H-imidazol-2-ylamino]-4-methyl-phenyl}-3-(4-ethyl-piperazin-1-yl)-5-trifluoromethyl-benzamide, N-(4-methyl-3-{1-[6-(2-morpholin-4-yl-ethylamino)-pyrimidin-4-yl]-1H-imidazol-2-ylamino}-phenyl)-3-trifluoromethyl-benzamide, N-{3-[1-(6-cyclopropylamino-pyrimidin-4-yl)-1H-imidazol-2-ylamino]-4-methyl-phenyl}-3-trifluoromethyl-benzamide, N-{4-methyl-3-[1-(6-methylamino-pyrimidin-4-yl)-1H-imidazol-2-ylamino]-phenyl}-3-trifluoromethyl-benzamide, N-[4-methyl-3-(1-{6-[3-(2-oxo-pyrrolidin-1-yl)-propylamino]-pyrimidin-4-yl}-1H-imidazol-2-ylamino)-phenyl]-3-trifluoromethyl-benzamide, N-(3-{1-[6-(benzo[1,3]dioxol-5-ylamino)-pyrimidin-4-yl]-1H-imidazol-2-ylamino}-4-methyl-phenyl)-3-trifluoromethyl-benzamide, N-[4-methyl-3-(1-{6-[3-(4-methyl-piperazin-1-yl)-propylamino]-pyrimidin-4-yl}-1H-imidazol-2-ylamino)-phenyl]-3-trifluoromethyl-benzamide, {6-[2-(2-chloro-phenylamino)-imidazol-1-yl]-pyrimidin-4-yl}-cyclopropyl-amine, (3-{6-[2-(2-chloro-phenylamino)-imidazol-1-yl]-pyrimidin-4-ylamino}-phenyl)-methanol, 1-(3-{6-[2-(2-chloro-phenylamino)-imidazol-1-yl]-pyrimidin-4-ylamino}-phenyl)-ethanol, {6-[2-(2-chloro-phenylamino)-imidazol-1-yl]-pyrimidin-4-yl}-[4-(2-morpholin-4-yl-ethyl)-phenyl]-amine, {6-[2-(2-chloro-phenylamino)-imidazol-1-yl]-pyrimidin-4-yl}-(4-morpholin-4-yl-phenyl)-amine, N-(3-{6-[2-(2-chloro-phenylamino)-imidazol-1-yl]-pyrimidin-4-ylamino}-phenyl)-acetamide, 1-(3-{6-[2-(2-chloro-phenylamino)-imidazol-1-yl]-pyrimidin-4-ylamino}-propyl)-pyrrolidin-2-one, benzo[1,3]dioxol-5-yl-{6-[2-(2-chloro-phenylamino)-imidazol-1-yl]-pyrimidin-4-yl}-amine, {6-[2-(2-chloro-phenylamino)-imidazol-1-yl]-pyrimidin-4-yl}-pyridin-3-yl-amine, N-(4-methyl-3-{1-[6-(pyridin-3-ylamino)-pyrimidin-4-yl]-1H-imidazol-2-ylamino}-phenyl)-3-trifluoromethyl-benzamide, {6-[2-(2-chloro-phenylamino)-imidazol-1-yl]-pyrimidin-4-yl}-(6-methyl-pyridin-3-yl)-amine, N-(4-methyl-3-{1-[6-(6-methyl-pyridin-3-ylamino)-pyrimidin-4-yl]-1H-imidazol-2-ylamino}-phenyl)-3-trifluoromethyl-benzamide, N-{3-[1-(6-cyclopropylamino-pyrimidin-4-yl)-1H-imidazol-2-ylamino]-4-methyl-phenyl}-3-morpholin-4-yl-5-trifluoromethyl-benzamide, N-{3-[1-(6-cyclopropylamino-pyrimidin-4-yl)-1H-imidazol-2-ylamino]-4-methyl-phenyl}-3-(4-methyl-piperazin-1-yl)-5-trifluoromethyl-benzamide, N-{3-[1-(6-cyclopropylamino-pyrimidin-4-yl)-1H-imidazol-2-ylamino]-4-methyl-phenyl}-3-(4-ethyl-piperazin-1-yl)-5-trifluoromethyl-benzamide, N-{3-[1-(6-cyclopropylamino-pyrimidin-4-yl)-1H-imidazol-2-ylamino]-4-methyl-phenyl}-4-morpholin-4-yl-3-trifluoromethyl-benzamide, N-{3-[1-(6-cyclopropylamino-pyrimidin-4-yl)-1H-imidazol-2-ylamino]-4-methyl-phenyl}-4-(4-ethyl-piperazin-1-ylmethyl)-3-trifluoromethyl-benzamide, N-{3-[1-(6-cyclopropylamino-pyrimidin-4-yl)-1H-imidazol-2-ylamino]-4-methyl-phenyl}-4-(4-methyl-piperazin-1-ylmethyl)-3-trifluoromethyl-benzamide, N-{3-[1-(6-cyclopropylamino-pyrimidin-4-yl)-1H-imidazol-2-ylamino]-4-methyl-phenyl}-3-(4-methyl-imidazol-1-yl)-5-trifluoromethyl-benzamide, 3-(4-methyl-imidazol-1-yl)-N-{4-methyl-3-[1-(6-methylamino-pyrimidin-4-yl)-1H-imidazol-2-ylamino]-phenyl}-5-trifluoromethyl-benzamide, N-{4-methyl-3-[1-(6-methylamino-pyrimidin-4-yl)-1H-imidazol-2-ylamino]-phenyl}-4-morpholin-4-yl-3-trifluoromethyl-benzamide, 3-(4-ethyl-piperazin-1-yl)-N-{4-methyl-3-[1-(6-methylamino-pyrimidin-4-yl)-1H-imidazol-2-ylamino]-phenyl}-5-trifluoromethyl-benzamide, N-{4-methyl-3-[1-(6-methylamino-pyrimidin-4-yl)-1H-imidazol-2-ylamino]-phenyl}-3-(4-methyl-piperazin-1-yl)-5-trifluoromethyl-benzamide, N-{3-[1-(6-methylamino-pyrimidin-4-yl)-1H-imidazol-2-ylamino]-phenyl}-4-(4-methyl-piperazin-1-ylmethyl)-3-trifluoromethyl-benzamide, 3-(4-ethyl-piperazin-1-ylmethyl)-N-{4-methyl-3-[1-(6-methylamino-pyrimidin-4-yl)-1H-imidazol-2-ylamino]-phenyl}-5-trifluoromethyl-benzamide, N-{3-[1-(6-cyclopropylamino-pyrimidin-4-yl)-1H-imidazol-2-ylamino]-4-methyl-phenyl}-4-morpholin-4-ylmethyl-3-trifluoromethyl-benzamide, N-{4-methyl-3-[1-(6-methylamino-pyrimidin-4-yl)-1H-imidazol-2-ylamino]-phenyl}-4-morpholin-4-ylmethyl-3-trifluoromethyl-benzamide, N-{3-[1-(6-amino-pyrimidin-4-yl)-1H-imidazol-2-ylamino]-4-methyl-phenyl}-4-(4-ethyl-piperazin-1-ylmethyl)-3-trifluoromethyl-benzamide, N-{3-[1-(6-amino-pyrimidin-4-yl)-1H-imidazol-2-ylamino]-4-methyl-phenyl}-4-(4-methyl-piperazin-1-ylmethyl)-3-trifluoromethyl-benzamide, N-{3-[1-(6-amino-pyrimidin-4-yl)-1H-imidazol-2-ylamino]-phenyl}-3-(4-methyl-imidazol-1-yl)-5-trifluoromethyl-benzamide, N-{3-[1-(6-amino-pyrimidin-4-yl)-1H-imidazol-2-ylamino]-4-methyl-phenyl}-4-morpholin-4-yl-3-trifluoromethyl-benzamide, N-{3-[1-(6-amino-pyrimidin-4-yl)-1H-imidazol-2-ylamino]-4-methyl-phenyl}-3-(4-ethyl-piperazin-1-yl)-5-trifluoromethyl-benzamide, N-{3-[1-(6-amino-pyrimidin-4- yl)-1H-imidazol-2-ylamino]-4-methyl-phenyl}-3-(4-methyl-piperazin-1-yl)-5-trifluoromethyl-benzamide, N-{3-[1-(6-amino-pyrimidin-4-yl)-1H-imidazol-2-ylamino]-4-methyl-phenyl}-3-morpholin-4-ylmethyl-5-trifluoromethyl-benzamide, 3-[1-(6-cyclopropylamino-pyrimidin-4-yl)-1H-imidazol-2-ylamino]-5-methoxy-N-[4-(2-methyl-imidazol-1-yl)-3-trifluoromethyl-phenyl]-benzamide, N-{3-[1-(6-acetylamino-pyrimidin-4-yl)-1H-imidazol-2-ylamino]-4-methyl-phenyl}-3-trifluoromethyl-benzamide, N-{3-[1-(6-methanesulfonylamino-pyrimidin-4-yl)-1H-imidazol-2-ylamino]-4-methyl-phenyl}-3-trifluoromethyl-benzamide, N-{3-[1-(2-cyclopropylamino-pyrimidin-4-yl)-1H-imidazol-2-ylamino]-4-methyl-phenyl}-3-trifluoromethyl-benzamide, 3-[1-(2-cyclopropylamino-pyrimidin-4-yl)-1H-imidazol-2-ylamino]-4-methyl-N-[4-(2-methyl-imidazol-1-yl)-3-trifluoromethyl-phenyl]-benzamide, N-{3-[1-(6-cyclopropylamino-pyrimidin-4-yl)-1H-imidazol-2-ylamino]-4-methyl-phenyl}-3-piperazin-1-ylmethyl-5-trifluoromethyl-benzamide, N-{3-[1-(6-amino-pyrimidin-4-yl)-1H-imidazol-2-ylamino]-4-methyl-phenyl}-3-piperazin-1-ylmethyl-5-trifluoromethyl-benzamide, N-{3-[1-(6-cyclopropylamino-pyrimidin-4-yl)-1H-imidazol-2-ylamino]-5-methoxy-phenyl}-4-(4-methyl-piperazin-1-ylmethyl)-3-trifluoromethyl-benzamide, N-{3-[1-(6-cyclopropylamino-pyrimidin-4-yl)-1H-imidazol-2-ylamino]-5-methoxy-phenyl}-3-(4-ethyl-piperazin-1-ylmethyl)-5-trifluoromethyl-benzamide, N-{3-[1-(6-cyclopropylamino-pyrimidin-4-yl)-1H-imidazol-2-ylamino]-4-methyl-phenyl}-3-(piperidin-4-yloxy)-5-trifluoromethyl-benzamide, N-{3-[1-(6-amino-pyrimidin-4-yl)-1H-imidazol-2-ylamino]-4-methyl-phenyl}-3-(piperidin-4-yloxy)-5-trifluoromethyl-benzamide, N-{3-[1-(6-cyclopropylamino-pyrimidin-4-yl)-1H-imidazol-2-ylamino]-5-methoxy-phenyl}-3-(4-pyrrolidin-1-yl-piperidin-1-yl)-5-trifluoromethyl-benzamide, 1-{3-[1-(6-cyclopropylamino-pyrimidin-4-yl)-1H-imidazol-2-ylamino]-4-methyl-phenyl}-3-[4-(2-methyl-imidazol-1-yl)-3-trifluoromethyl-phenyl]-urea, 1-{3-[1-(6-cyclopropylamino-pyrimidin-4-yl)-1H-imidazol-2-ylamino]-4-methyl-phenyl}-3-[4-(4-ethyl-piperazin-1-ylmethyl)-3-trifluoromethyl-phenyl]-urea, pyridazine-4-carboxylic acid {3-[1-(6-cyclopropylamino-pyrimidin-4-yl)-1H-imidazol-2-ylamino]-4-methyl-phenyl}-amide, 2-chloro-N-{3-[1-(6-cyclopropylamino-pyrimidin-4-yl)-1H-imidazol-2-ylamino]-4-methyl-phenyl}-isonicotinamide, furan-2-carboxylic acid {3-[1-(6-cyclopropylamino-pyrimidin-4-yl)-1H-imidazol-2-ylamino]-4-methyl-phenyl}-amide, 1-methyl-1H-pyrrole-2-carboxylic acid {3-[1-(6-cyclopropylamino-pyrimidin-4-yl)-1H-imidazol-2-ylamino]-4-methyl-phenyl}-amide, 1H-imidazole-2-carboxylic acid {3-[1-(6-cyclopropylamino-pyrimidin-4-yl)-1H-imidazol-2-ylamino]-4-methyl-phenyl}-amide, N-{3-[1-(6-cyclopropylamino-pyrimidin-4-yl)-1H-imidazol-2-ylamino]-4-methyl-phenyl}-4-trifluoromethyl-benzamide, N-{3-[1-(6-cyclopropylamino-pyrimidin-4-yl)-1H-imidazol-2-ylamino]-4-methyl-phenyl}-6-methyl-nicotinamide, 1-tert-butyl-5-methyl-1H-pyrazole-3-carboxylic acid {3-[1-(6-cyclopropylamino-pyrimidin-4-yl)-1H-imidazol-2-ylamino]-4-methyl-phenyl}-amide, N-[4-(4-ethyl-piperazin-1-ylmethyl)-3-trifluoromethyl-phenyl]-4-methyl-3-{1-[6-(2-morpholin-4-yl-ethylamino)-pyrimidin-4-yl]-1H-imidazol-2-ylamino}-benzamide, 3-(4-methyl-imidazol-1-yl)-N-(4-methyl-3-{1-[6-(2-morpholin-4-yl-ethylamino)-pyrimidin-4-yl]-1H-imidazol-2-ylamino}-phenyl)-trifluoromethyl-benzamide, 4-methyl-N-[4-(2-methyl-imidazol-1-yl)-3-trifluoromethyl-phenyl]-3-{1-[6-(2-morpholin-4-yl-ethylamino)-pyrimidin-4-yl]-1H-imidazol-2-ylamino}-benzamide, N-(4-methyl-3-{1-[6-(2-morpholin-4-yl-ethylamino)-pyrimidin-4-yl]-1H-imidazol-2-ylamino}-phenyl)-3-(1-methyl-piperidin-4-yloxy)-5-trifluoromethyl-benzamide, pyrazine-2-carboxylic acid {3-[1-(6-cyclopropylamino-pyrimidin-4-yl)-1H-imidazol-2-ylamino]-4-methyl-phenyl}-amide, 5-methyl-pyrazine-2-carboxylic acid {3-[1-(6-cyclopropylamino-pyrimidin-4-yl)-1H-imidazol-2-ylamino]-4-methyl-phenyl}-amide, quinoxaline-6-carboxylic acid {3-[1-(6-cyclopropylamino-pyrimidin-4-yl)-1H-imidazol-2-ylamino]-4-methyl-phenyl}-amide, 5-tert-butyl-2-methyl-4-morpholin-4-ylmethyl-furan-3-carboxylic acid {3-[1-(6-cyclopropylamino-pyrimidin-4-yl)-1H-imidazol-2-ylamino]-4-methyl-phenyl}-amide, 5-tert-butyl-2-methyl-2H-pyrazole-3-carboxylic acid {3-[1-(6-cyclopropylamino-pyrimidin-4-yl)-1H-imidazol-2-ylamino]-4-methyl-phenyl}-amide, 2-benzyl-5-tert-butyl-2H-pyrazole-3-carboxylic acid {3-[1-(6-cyclopropylamino-pyrimidin-4-yl)-1H-imidazol-2-ylamino]-4-methyl-phenyl}-amide, N-{3-[1-(6-cyclopropylamino-pyrimidin-4-yl)-1H-imidazol-2-ylamino]-4-methyl-phenyl}-3-(piperidin-4-ylamino)-5-trifluoromethyl-benzamide, N-{3-[1-(6-cyclopropylamino-pyrimidin-4-yl)-1H-imidazol-2-ylamino]-4-methyl-phenyl}-3-(pyrrolidin-2-ylmethoxy)-5-trifluoromethyl-benzamide, 5-tert-butyl-2-methyl-furan-3-carboxylic acid {3-[1-(6-cyclopropylamino-pyrimidin-4-yl)-1H-imidazol-2-ylamino]-4-methyl-phenyl}-amide, 5-tert-butyl-3-methyl-furan-2-carboxylic acid {3-[1-(6-cyclopropylamino-pyrimidin-4-yl)-1H-imidazol-2-ylamino]-4-methyl-phenyl}-amide, 5-tert-butyl-2-diethylamino-furan-3-carboxylic acid {3-[1-(6-cyclopropylamino-pyrimidin-4-yl)-1H-imidazol-2-ylamino]-4-methyl-phenyl}-amide, 5-tert-butyl-4-diethylamino-2-methyl-furan-3-carboxylic acid {3-[1-(6-cyclopropylamino-pyrimidin-4-yl)-1H-imidazol-2-ylamino]-4-methyl-phenyl}-amide, 5-tert-butyl-thiophene-2-carboxylic acid {3-[1-(6-cyclopropylamino-pyrimidin-4-yl)-1H-imidazol-2-ylamino]-4-methyl-phenyl}-amide, 5-tert-butyl-3-methyl-furan-2-carboxylic acid (4-methyl-3-{1-[6-(2-morpholin-4-yl-ethylamino)-pyrimidin-4-yl]-1H-imidazol-2-ylamino}-phenyl)-amide, 5-tert-butyl-thiophene-2-carboxylic acid (4-methyl-3-{1-[6-(2-morpholin-4-yl-ethylamino)-pyrimidin-4-yl]-1H-imidazol-2-ylamino}-phenyl)-amide, 5-tert-butyl-2-methyl-furan-3-carboxylic acid (4-methyl-3-{1-[6-(2-morpholin-4-yl-ethylamino)-pyrimidin-4-yl]-1H-imidazol-2-ylamino}-phenyl)-amide, N-(3-{1-[6-(4-amino-cyclohexylamino)-pyrimidin-4-yl]-1H-imidazol-2-ylamino}-4-methyl-phenyl)-3-trifluoromethyl-benzamide, N-(4-methyl-3-{1-[6-(piperidin-4-ylamino)-pyrimidin-4-yl]-1H-imidazol-2-ylamino}-phenyl)-3-trifluoromethyl-benzamide, N-[4-methyl-3-(1-{6-[2-(4-methyl-piperazin-1-yl)-ethylamino]-pyrimidin-4-yl}-1H-imidazol-2-ylamino)-phenyl]-3-trifluoromethyl-benzamide, N-(3-{1-[6-(2,5-dimethyl-2H-pyrazol-3-ylamino)-pyrimidin-4-yl]-1H-imidazol-2-ylamino}-4-methyl-phenyl)-3-trifluoromethyl-benzamide, N-(4-methyl-3-{1-[6-(4-methyl-piperazin-1-ylamino)-pyrimidin-4-yl]-1H-imidazol-2-ylamino}-phenyl)-3-trifluoromethyl-benzamide, N-(4-methyl-3-{1-[6-(2-methyl-2H-pyrazol-3-ylamino)-pyrimidin-4-yl]-1H-imidazol-2-ylamino}-phenyl)-3-trifluoromethyl-benzamide, N-(3-{1-[6-(2,6-dimethyl-pyridin-3-ylamino)-pyrimidin-4-yl]-1H-imidazol-2-ylamino}-4-methyl-phenyl)-3-trifluoromethyl-benzamide, N-(4-methyl-3-{1-[6-(2-methyl-pyridin-3-ylamino)-pyrimidin-4-yl]-1H-imidazol-2-ylamino}-phenyl)-3-trifluoromethyl-benzamide, N-{3-[1-(6-cyclopropylamino-pyrimidin-4-yl)-1H-imidazol-2-ylamino]-4-methyl-phenyl}-3-(4-methyl-piperazin-1-yl)-5-trifluoromethyl-benzamide, N-{3-[1-(6-cyclopropylaminopyrimidin-4-yl)-1H-imidazol-2-ylamino]-4-methyl-phenyl}-3-[4-(2-hydroxy-ethyl)-piperazin-1-yl]-5-trifluoromethyl-benzamide, N-{3-[1-(6-cyclopropylamino-pyrimidin-4-yl)-1H-imidazol-2-ylamino]-4-methyl-phenyl}-3-piperazin-1-yl-5-trifluoromethyl-benzamide, N-{4-chloro-3-[1-(6-cyclopropylamino-pyrimidin-4-yl)-1H-imidazol-2-ylamino]-phenyl}-benzamide, N-{3-[1-(6-cyclopropylamino-pyrimidin-4-yl)-1H-imidazol-2-ylamino]-4-fluoro-phenyl}-benzamide, N-{3-[1-(6-cyclopropylamino-pyrimidin-4-yl)-1H-imidazol-2-ylamino]-2-methyl-phenyl}-benzamide, N-{5-[1-(6-cyclopropylamino-pyrimidin-4-yl)-1H-imidazol-2-ylamino]-2-fluoro-phenyl}-benzamide, N-{5-[1-(6-cyclopropylamino-pyrimidin-4-yl)-1H-imidazol-2-ylamino]-2-methyl-phenyl}-benzamide, N-{4-chloro-3-[1-(6-cyclopropylamino-pyrimidin-4-yl)-1H-imidazol-2-ylamino]-phenyl}-4-morpholin-4-ylmethyl-3-trifluoromethyl-benzamide, N-{3-[1-(6-cyclopropylamino-pyrimidin-4-yl)-1H-imidazol-2-ylamino]-4-fluoro-phenyl}-4-morpholin-4-ylmethyl-3-trifluoromethyl-benzamide, N-{3-[1-(6-cyclopropylamino-pyrimidin-4-yl)-1H-imidazol-2-ylamino]-2-methyl-phenyl}-4-morpholin-4-ylmethyl-3-trifluoromethyl-benzamide, N-{4-chloro-3-[1-(6-cyclopropylamino-pyrimidin-4-yl)-1H-imidazol-2-ylamino]-phenyl}-3-(4-methyl-imidazol-1-yl)-5-trifluoromethyl-benzamide, N-{3-[1-(6-cyclopropylamino-pyrimidin-4-yl)-1H-imidazol-2-ylamino]-4-fluoro-phenyl}-3-(4-methyl-imidazol-1-yl)-5-trifluoromethyl-benzamide, N-{3-[1-(6-cyclopropylamino-pyrimidin-4-yl)-1H-imidazol-2-ylamino]-2-methyl-phenyl}-3-(4-methyl-imidazol-1-yl)-5-trifluoromethyl-benzamide, N-{5-[1-(6-cyclopropylamino-pyrimidin-4-yl)-1H-imidazol-2-ylamino]-2-fluoro-phenyl}-3-(4-methyl-imidazol-1-yl)-5-trifluoromethyl-benzamide, N-{5-[1-(6-cyclopropylamino-pyrimidin-4-yl)-1H-imidazol-2-ylamino]-2-methyl-phenyl}-3-(4-methyl-imidazol-1-yl)-5-trifluoromethyl-benzamide, N-{3-[1-(6-cyclopropylamino-pyrimidin-4-yl)-1H-imidazol-2-ylamino]-4-methoxy-phenyl}-benzamide, N-{3-[1-(6-cyclopropylamino-pyrimidin-4-yl)-1H-imidazol-2-ylamino]-4-methyl-phenyl}-3-trifluoromethyl-benzenesulfonamide, 3-[1-(6-cyclopropylamino-pyrimidin-4-yl)-1H-imidazol-2-ylamino]-4-methyl-N-(3-trifluoromethyl-phenyl)-benzenesulfonamide, N-{3-[1-(6-cyclopropylamino-pyrimidin-4-yl)-1H-imidazol-2-ylamino]-4-fluoro-phenyl}-3-dimethylamino-5-trifluoromethyl-benzamide, N-{5-[1-(6-cyclopropylamino-pyrimidin-4-yl)-1H-imidazol-2-ylamino]-2-methyl-phenyl}-3-dimethylamino-5-trifluoromethyl-benzamide, N-{4-chloro-3-[1-(6-cyclopropylamino-pyrimidin-4-yl)-1H-imidazol-2-ylamino]-phenyl}-3-dimethylamino-5-trifluoromethyl-benzamide, 3-(4-methyl-imidazol-1-yl)-N-(4-methyl-3-{1-[6-(pyridin-2-ylamino)-pyrimidin-4-yl]-1H-imidazol-2-ylamino}-phenyl)-5-trifluoromethyl-benzamide, 4-(4-ethyl-piperazin-1-ylmethyl)-N-(4-methyl-3-{1-[6-(pyridin-2-ylamino)-pyrimidin-4-yl]-1H-imidazol-2-ylamino}-phenyl)-3-trifluoromethyl-benzamide, 3-(4-ethyl-piperazin-1-yl)-N-(4-methyl-3-{1-[6-(pyridin-2-ylamino)-pyrimidin-4-yl]-1H-imidazol-2-ylamino}-phenyl)-5-trifluoromethyl-benzamide, 4-chloro-N-(4-methyl-3-{1-[6-(pyridin-2-ylamino)-pyrimidin-4-yl]-1H-imidazol-2-ylamino}-phenyl)-3-trifluoromethyl-benzamide, N-[3-(1-{6-[5-(4-ethyl-piperazin-1-yl)-pyridin-2-ylamino]-pyrimidin-4-yl}-1H-imidazol-2-ylamino)-4-methyl-phenyl]-3-trifluoromethyl-benzamide, N-(4-methyl-3-{1-[6-(4-methyl-pyridin-2-ylamino)-pyrimidin-4-yl]-1H-imidazol-2-ylamino}-phenyl)-3-trifluoromethyl-benzamide, N-(3-{1-[6-(4,6-dimethyl-pyridin-2-ylamino)-pyrimidin-4-yl]-1H-imidazol-2-ylamino}-4-methyl-phenyl)-3-trifluoromethyl-benzamide, 6-(6-{2-[2-methyl-5-(3-trifluoromethyl-benzoylamino)-phenylamino]-imidazol-1-yl}-pyrimidin-4-ylamino)-nicotinamide, N-(4-methyl-3-{1-[6-(5-methyl-pyridin-2-ylamino)-pyrimidin-4-yl]-1H-imidazol-2-ylamino}-phenyl)-3-trifluoromethyl-benzamide, N-(3-{1-[6-(5-cyano-pyridin-2-ylamino)-pyrimidin-4-yl]-1H-imidazol-2-ylamino}-4-methyl-phenyl)-3-trifluoromethyl-benzamide, 4-chloro-N-{3-[1-(6-cyclopropylamino-pyrimidin-4-yl)-1H-imidazol-2-ylamino]-4-methyl-phenyl}-3-trifluoromethyl-benzamide, 4-chloro-N-(4-methyl-3-{1-[6-(2-morpholin-4-yl-ethylamino)-pyrimidin-4-yl]-1H-imidazol-2-ylamino}-phenyl)-3-trifluoromethyl-benzamide, 5-tert-butyl-2-methyl-2H-pyrazole-3-carboxylic acid (4-methyl-3-{1-[6-(2-morpholin-4-yl-ethylamino)-pyrimidin-4-yl]-1H-imidazol-2-ylamino}-phenyl)-amide, N-(3-{1-[6-(2-dimethylamino-ethylamino)-pyrimidin-4-yl]-1H-imidazol-2-ylamino}-4-methyl-phenyl)-3-trifluoromethyl-benzamide, N-(4-methyl-3-{1-[6-(3-morpholin-4-yl-propylamino)-pyrimidin-4-yl]-1H-imidazol-2-ylamino}-phenyl)-3-trifluoromethyl-benzamide, N-(3-{1-[6-(2-methoxy-ethylamino)-pyrimidin-4-yl]-1H-imidazol-2-ylamino}-4-methyl-phenyl)-3-trifluoromethyl-benzamide, N-[4-methyl-3-(1-{6-[2-(1-methyl-pyrrolidin-2-yl)-ethylamino]-pyrimidin-4-yl}-1H-imidazol-2-ylamino)-phenyl]-3-trifluoromethyl-benzamide, N-(4-methyl-3-{1-[6-(pyridin-2-ylamino)-pyrimidin-4-yl]-1H-imidazol-2-ylamino}-phenyl)-3-trifluoromethyl-benzamide, N-[4-methyl-3-(1-pyrimidin-4-yl-1H-imidazol-2-ylamino)-phenyl]-3-trifluoromethyl-benzamide, N-[4-methyl-3-(1-pyrimidin-2-yl-1H-imidazol-2-ylamino)-phenyl]-3-trifluoromethyl-benzamide, N-{4-methyl-3-[1-(4-methylamino-pyrimidin-2-yl)-1H-imidazol-2-ylamino]-phenyl}-3-trifluoromethyl-benzamide, N-{4-methyl-3-[1-(2-methylamino-pyrimidin-4-yl)-1H-imidazol-2-ylamino]-phenyl}-3-trifluoromethyl-benzamide, N-(4-methyl-3-{1-[4-(2-morpholin-4-yl-ethylamino)-pyrimidin-2-yl]-1H-imidazol-2-ylamino}-phenyl)-3-trifluoromethyl-benzamide, N-(4-methyl-3-{1-[2-(2-morpholin-4-yl-ethylamino)-pyrimidin-4-yl]-1H-imidazol-2-ylamino}-phenyl)-3-trifluoromethyl-benzamide, N-(3-{1-[6-(2-ethyl-2H-pyrazol-3-ylamino)-pyrimidin-4-yl]-1H-imidazol-2-ylamino}-4-methyl-phenyl)-3-trifluoromethyl-benzamide, N-(3-{1-[6-(3-dimethylamino-propylamino)-pyrimidin-4-yl]-1H-imidazol-2-ylamino}-4-methyl-phenyl)-3-trifluoromethyl-benzamide, N-{3-[1-(6-isopropylamino-pyrimidin-4-yl)-1H-imidazol-2-ylamino]-4-methyl-phenyl}-3-trifluoromethyl-benzamide, N-[3-(1-{6-[(furan-3-ylmethyl)-amino]-pyrimidin-4-yl}-1H-imidazol-2-ylamino)-4-methyl-phenyl]-3-trifluoromethyl-benzamide, N-[4-methyl-3-(1-{6-[3-(4-methyl-piperazin-1-yl)-propylamino]-pyrimidin-4-yl}-1H-imidazol-2-ylamino)-phenyl]-3-trifluoromethyl-benzamide, N-[3-(1-{6-[(benzo[1,3]dioxol-5-ylmethyl)-amino]-pyrimidin-4-yl}-1H-imidazol-2-ylamino)-4-methyl-phenyl]-3-trifluoromethyl-benzamide, N-(4-methyl-3-{1-[6-(2-methyl-6-morpholin-4-yl-pyridin-3-ylamino)-pyrimidin-4-yl]-1H-imidazol-2-ylamino}-phenyl)-3-trifluoromethyl-benzamide, N-(4-methyl-3-{1-[6-(4-methyl-pyrimidin-2-ylamino)-pyrimidin-4-yl]-1H-imidazol-2-ylamino}-phenyl)-3-trifluoromethyl-benzamide, N-(3-{1-[6-(6-methoxy-pyridin-3-ylamino)-pyrimidin-4-yl]-1H-imidazol-2-ylamino}-4-methyl-phenyl)-3-trifluoromethyl-benzamide, N-{4-methyl-3-[1-(6-morpholin-4-yl-pyrimidin-4-yl)-1H-imidazol-2-ylamino]-phenyl}-3-trifluoromethyl-benzamide, N-(3-{1-[6-(4-ethyl-piperazin-1-yl)-pyrimidin-4-yl]-1H-imidazol-2-ylamino}-4-methyl-phenyl)-3-trifluoromethyl-benzamide, N-(3-{1-[6-(3-fluorophenylamino)-pyrimidin-4-yl]-1H-imidazol-2-ylamino}-4-methyl-phenyl)-3-trifluoromethyl-benzamide, N-(3-{1-[6-(3-dimethylamino-ethyl-formamide-phenylamino)-pyrimidin-4-yl]-1H-imidazol-2-ylamino}-4-methyl-phenyl)-3-trifluoromethyl-benzamide, N-[4-methyl-3-(1-{6-[(pyridin-3-ylmethyl)-amino]-pyrimidin-4-yl}-1H-imidazol-2-ylamino)-phenyl]-3-trifluoromethyl-benzamide, N-[4-methyl-3-(1-{6-[(pyridin-4-ylmethyl)-amino]-pyrimidin-4-yl}-1H-imidazol-2-ylamino)-phenyl]-3-trifluoromethyl-benzamide, N-(4-methyl-3-{1-[6-(4-morpholin-4-yl-piperidin-1-yl)-pyrimidin-4-yl]-1H-imidazol-2-ylamino}-phenyl)-3-trifluoromethyl-benzamide, N-[4-methyl-3-(1-{6-[(thiazol-2-ylmethyl)-amino]-pyrimidin-4-yl}-1H-imidazol-2-ylamino)-phenyl]-3-trifluoromethyl-benzamide, N-[4-methyl-3-(1-{6-[(pyridin-2-ylmethyl)-amino]-pyrimidin-4-yl}-1H-imidazol-2-ylamino)-phenyl]-3-trifluoromethyl-benzamide, N-[4-methyl-3-(1-{6-[(6-methyl-pyrazin-2-ylmethyl)-amino]-pyrimidin-4-yl}-1H-imidazol-2-ylamino)-phenyl]-3-trifluoromethyl-benzamide, N-(4-methyl-3-{1-[6-(4-pyridin-2-yl-piperazin-1-yl)-pyrimidin-4-yl]-1H-imidazol-2-ylamino}-phenyl)-3-trifluoromethyl-benzamide, N-(3-{1-[6-(3-imidazol-1-yl-propylamino)-pyrimidin-4-yl]-1H-imidazol-2-ylamino}-4-methyl-phenyl)-3-trifluoromethyl-benzamide, N-(4-methyl-3-{1-[6-(pyrazin-2-ylamino)-pyrimidin-4-yl]-1H-imidazol-2-ylamino}-phenyl)-3-trifluoromethyl-benzamide, N-(3-{1-[6-(3-formamide-phenylamino)-pyrimidin-4-yl]-1H-imidazol-2-ylamino}-4-methyl-phenyl)-3-trifluoromethyl-benzamide, 4-methyl-3-{1-[6-(2-morpholin-4-yl-ethylamino)-pyrimidin-4-yl]-1H-imidazol-2-ylamino}-N-(3-trifluoromethyl-phenyl)-benzamide, 4-methyl-3-{1-[6-(4-methyl-piperazin-1-ylamino)-pyrimidin-4-yl]-1H-imidazol-2-ylamino}-N-(3-trifluoromethyl-phenyl)-benzamide, N-(4-chloro-3-trifluoromethyl-phenyl)-4-methyl-3-{1-[6-(2-morpholin-4-yl-ethylamino)-pyrimidin-4-yl]-1H-imidazol-2-ylamino}-benzamide, N-(4-chloro-3-trifluoromethyl-phenyl)-4-methyl-3-{1-[6-(4-methyl-piperazin-1-ylamino)-pyrimidin-4-yl]-1H-imidazol-2-ylamino}-benzamide, 1-tert-butyl-5-(4-methyl-piperazin-1-ylmethyl)-1H-pyrazole-3-carboxylic acid {3-[1-(6-cyclopropylamino-pyrimidin-4-yl)-1H-imidazol-2-ylamino]-4-methyl-phenyl}-amide, 1-tert butyl-5-morpholin-4-ylmethyl-1H-pyrazole-3-carboxylic acid {3-[1-(6-cyclopropylamino-pyrimidin-4-yl)-1H-imidazol-2-ylamino]-4-methyl-phenyl}-amide, N-(4-tert-butyl-thiazol-2-yl)-4-methyl-3-{1-[6-(2-morpholin-4-yl-ethylamino)-pyrimidin-4-yl]-1H-imidazol-2-ylamino}-benzamide, N-(4-tert-butyl-thiazol-2-yl)-4-methyl-3-{1-[6-(4-methyl-piperazin-1-ylamino)-pyrimidin-4-yl]-1H-imidazol-2-ylamino}-benzamide, N-(5-tert-butyl-2-methyl-2H-pyrazol-3-yl)-4-methyl-3-{1-[6-(4-methyl-piperazin-1-ylamino)-pyrimidin-4-yl]-1H-imidazol-2-ylamino}-benzamide, N-(4-methyl-3-{1-[6-(4-methyl-piperazin-1-ylamino)-pyrimidin-4-yl]-1H-imidazol-2-ylamino}-phenyl)-benzamide, N-(5-tert-butyl-2-methyl-2H-pyrazol-3-yl)-4-methyl-3-{1-[6-(2-morpholin-4-yl-ethylamino)-pyrimidin-4-yl]-1H-imidazol-2-ylamino}-benzamide, N-(4-methyl-3-{1-[2-(2-morpholin-4-yl-ethylamino)-pyridin-4-yl]-1H-imidazol-2-ylamino}-phenyl)-3-trifluoromethyl-benzamide, N-{3-[1-(4-acetylamino-pyridin-2-yl)-1H-imidazol-2-ylamino]-4-methyl-phenyl}-3-trifluoromethyl-benzamide and 2-{2-[2-Methyl-5-(3-trifluoromethyl-benzoylamino)-phenylamino]-imidazol-1-yl}-isonicotinamide.

6. A pharmaceutical composition comprising a therapeutically effective amount of a compound of claim 1 in combination with a pharmaceutically acceptable excipient.

7. A method for treating leukemia in an animal in which inhibition of kinase activity can inhibit or ameliorate the pathology and/or symptomology of the kinase mediated disease, which method comprises administering to the animal a therapeutically effective amount of a compound of claim 1.

8. The method of claim 7 in which the kinase is selected from the group consisting of Abl, BCR-Abl, PDGF-R, trkB, c-SRC, BMX, FGFR3, b-RAF, SGK, Tie2, Lck, JNK2α2, MKK4, c-RAF, MKK6, SAPK2α and SAPK2β.

\* \* \* \* \*